United States Patent [19]
Brown et al.

[11] Patent Number: 6,096,895
[45] Date of Patent: Aug. 1, 2000

[54] HETEROCYCLIC DIHYDRAZOLE COMPOUNDS AND THEIR USE FOR CONTROLLING FUNGAL PLANT DISEASES

[75] Inventors: Richard James Brown, Newark; Dilon Jancey Daniel, Bear, both of Del.; Deborah Ann Frasier, Martinez, Calif.; Michael Henry Howard, Jr., Rockland, Del.; Gerard Michael Koether, Bear, Del.; Morris Padgett Rorer, Newark, Del.

[73] Assignee: E. I. du Pont de Nemours and Company, Wilmington, Del.

[21] Appl. No.: 08/952,384

[22] PCT Filed: May 8, 1996

[86] PCT No.: PCT/US96/06533

§ 371 Date: Nov. 13, 1997

§ 102(e) Date: Nov. 13, 1997

[87] PCT Pub. No.: WO96/36633

PCT Pub. Date: Nov. 21, 1996

Related U.S. Application Data

[63] Continuation-in-part of application No. 08/443,295, May 17, 1995, abandoned.

[51] Int. Cl.$^7$ ...... A01N 43/647; C07D 405/04; C07D 409/04; C07D 249/12; C07D 417/14
[52] U.S. Cl. ...... 548/110; 514/247; 514/256; 514/340; 514/342; 514/361; 514/380; 514/383; 544/238; 544/333; 544/335; 546/14; 546/256; 546/272.1; 546/272.4; 548/129; 548/203; 548/205; 548/243; 548/263.4; 548/263.6; 548/266.2
[58] Field of Search ...... 548/263.4, 263.6, 548/266.2, 243, 110, 203, 205, 129; 514/384, 380, 383, 256, 247, 340, 342, 238, 333, 335; 546/14, 256, 272.1, 272.4

[56] References Cited

U.S. PATENT DOCUMENTS

| | | | |
|---|---|---|---|
| 3,953,006 | 4/1976 | Tahara et al. | 548/266.2 X |
| 5,089,627 | 2/1992 | Muller et al. | 548/263.6 |
| 5,145,982 | 9/1992 | Lai et al. | 548/266.6 |
| 5,206,256 | 4/1993 | Lang | 514/383 |
| 5,212,197 | 5/1993 | Dolman et al. | 514/397 |
| 5,244,865 | 9/1993 | Seltz et al. | 504/239 |
| 5,350,861 | 9/1994 | Fischer et al. | 548/544 |
| 5,463,072 | 10/1995 | Bergthaller | 548/255 |
| 5,747,516 | 5/1998 | Brown et al. | 514/359 |

FOREIGN PATENT DOCUMENTS

| | | |
|---|---|---|
| 0011693 | 6/1980 | European Pat. Off. |
| 0517357 | 12/1992 | European Pat. Off. |
| 0554956 | 8/1993 | European Pat. Off. |
| A 0 554 956 | 8/1993 | European Pat. Off. |
| 0 625 520 | 11/1994 | European Pat. Off. |
| 4102339 | 7/1992 | Germany |
| 4118720 | 12/1992 | Germany |
| 92-16510 | 10/1992 | WIPO |
| WO 95/01973 | 1/1995 | WIPO |
| 95-14009 | 5/1995 | WIPO |
| WO96/17851 | 6/1996 | WIPO |
| WO96/26191 | 8/1996 | WIPO |
| WO 96/36616 | 11/1996 | WIPO |
| WO96/36229 | 11/1996 | WIPO |

OTHER PUBLICATIONS

Zvilichovsky, G., *J. Heterocyclic Chem.*, 24, 465–470 (1987).
Zvilichovsky, G. et al., *J. Heterocyclic Chem.*, 25, 1307–1310 (1988).
Davis, M. et al., *Australian J. Chem.*, 30(8), 1815–1818 (1977).

*Primary Examiner*—Floyd D. Higel

[57] ABSTRACT

Compounds of Formula I, and their N-oxides and agriculturally suitable salts, are disclosed which are useful as fungicides

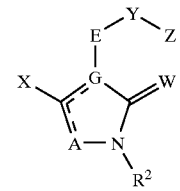

I

In said formula, E is a ring system selected from certain 5- to 12-membered monocyclic and fused bicyclic aromatic heterocyclic ring systems, or an optionally substituted naphthalene ring as defined in the disclosure;

A is O; S; N; NR$^5$; or CR$^{14}$;

G is C or N; provided that when G is C, then A is O, S or NR$^5$ and the floating double bond is attached to G; and when G is N, then A is N or CR$^{14}$ and the floating double bond is attached to A;

W is O; S; NH; N(C$_1$–C$_6$ alkyl); or NO(C$_1$–C$_6$ alkyl);

X is OR$^1$; S(O)$_m$R$^1$; or halogen;

R$^1$ is C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; or C$_2$–C$_4$ alkoxycarbonyl;

R$^2$ is H; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; C$_2$–C$_4$ alkoxycarbonyl; hydroxy; C$_1$–C$_2$ alkoxy; or acetyloxy;

R$^5$ is H; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; or C$_2$–C$_4$ alkoxycarbonyl; and Y, Z, R$^{14}$ and m are as defined in the disclosure.

Also disclosed are compositions containing the compounds of Formula I and a method for controlling plant diseases caused by fungal plant pathogens which involves applying an effective amount of a compound of Formula I.

18 Claims, No Drawings

HETEROCYCLIC DIHYDRAZOLE COMPOUNDS AND THEIR USE FOR CONTROLLING FUNGAL PLANT DISEASES

This application is a national filing under 35 USC 371 of International Application No. PCT/US96/06533 filed May 8, 1996 which is a continuation-in-part of U.S. patent application Ser. No. 08/443,295 filed May 17, 1995 (now abandoned).

BACKGROUND OF THE INVENTION

This invention relates to certain cyclic amides, their N-oxides, agriculturally suitable salts and compositions, and methods of their use as fungicides.

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different modes of action.

WO 95/01973 discloses certain heterocyclic amides and esters of Formula i as fungicides

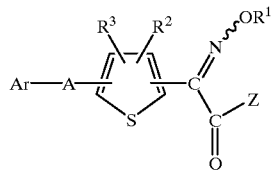

i wherein

Ar is substituted aryl or heteroaryl;

$R^1$ is alkyl or haloalkyl;

$R^2$ and $R^3$ are independently, among others, hydrogen, halogen, cyano, nitro, alkyl, alkoxy, alkylthio, alkenyl, alkenyloxy, alkynyl, alkynyloxy, haloallyl, haloalkoxy, haloalkenyl, haloalkynyl, alkoxycarbonyl, or substituted phenyl;

A is —O—; —CH=CH—; —C≡C—; —CH$_2$O—; —OCH$_2$—; —CH$_2$S(O)$_n$—; —S(O)$_n$CH$_2$—; —S(O)$_n$—; —C(R$^4$)=N—O—; —C(R$^4$)=N—OCH$_2$—; or —NR$^6$—;

Z is OR$^5$ or NR$^6$R$^7$;

$R^4$ is H, alkyl, haloalkyl, cycloalkyl or cyano;

$R^5$ is alkyl or haloalkyl;

$R^6$ and $R^7$ are independently H, alkyl, haloalkyl or alkoxy; and n is 0, 1 or 2.

The cyclic amides of the present invention are not disclosed therein.

J. Heterocyclic Chem., (1987), 24, 465, J. Heterocyclic Chem., (1988), 25, 1307, and Australian J. Chem., (1977), 30 (8), 1815 disclose 4-nitrophenyl isoxazoles (ii), phenyl pyrazolones (iii), and aryl isothiazolinones (iv) respectively.

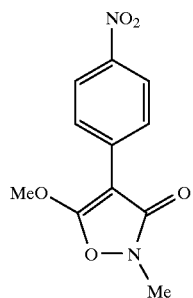

ii

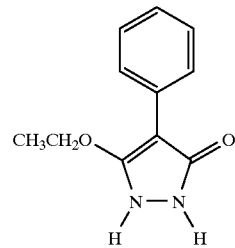

iii

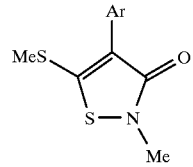

iv

However, no utility as fungicides is alleged and the cyclic amides of the present invention are not disclosed therein.

SUMMARY OF THE INVENTION

This invention is directed to compounds of Formula I including all geometric and stereoisomers, N-oxides, and agriculturally suitable salts thereof, agricultural compositions containing them and their use as fungicides:

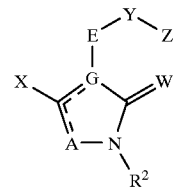

I wherein

E is a ring system selected from:

i) 5 to 12-membered monocyclic and fused bicyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each fused bicyclic ring system optionally containing one non-aromatic ring that optionally includes one or two Q as ring members and optionally includes one or two ring members independently selected from C(=O) and S(O)$_2$, provided that G is attached to an aromatic ring, and when G and Y are attached to the same ring, then G and Y are attached to adjacent ring members, each aromatic heterocyclic ring system optionally substituted with one of $R^3$, $R^4$, or both $R^3$ and $R^4$; and ii) a naphthalene ring, provided that when G and Y are attached to the same ring, then G and Y are attached to adjacent ring members, the naphthalene ring optionally substituted with one of $R^3$, $R^4$, or both $R^3$ and $R^4$, provided that when G is attached to the 1, 4, 5, or 8 position of the naphthalene ring and Z is $C_1$–$C_{10}$ alkyl, $C_2$–$C_{10}$ alkenyl, $C_2$–$C_{10}$ alkynyl or phenyl each substituted with $R^9$ and optionally substituted with one or more $R^{10}$, then Y is other than —O—, —S(O)$_n$—, —C(=O)—, —CHR$^6$—, —CHR$^6$CHR$^6$—, —CR$^6$=CR$^6$—, —C≡C—, —OCHR$^{15}$—, —S(O)$_n$CHR$^{15}$— or a direct bond;

A is O; S; N; NR$^5$; or CR$^{14}$;

G is C or N; provided that when G is C, then A is O, S or NR$^5$ and the floating double bond is attached to G; and when G is N, then A is N or CR$^{14}$ and the floating double bond is attached to A;

W is O; S; NH; N(C$_1$–C$_6$ alkyl); or NO(C$_1$–C$_6$ alkyl);

X is OR$^1$; S(O)$_m$R$^1$; or halogen;

$R^1$ is $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

$R^2$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; hydroxy; $C_1$–$C_2$ alkoxy; or acetyloxy;

$R^3$ and $R^4$ are each independently halogen; cyano; nitro; hydroxy; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1$–$C_6$ alkoxy; $C_1$–$C_6$ haloalkoxy; $C_2$–$C_6$ alkenyloxy; $C_2$–$C_6$ alkynyloxy; $C_1$–$C_6$ alkylthio; $C_1$–$C_6$ alkylsulfinyl; $C_1$–$C_6$ alkylsulfonyl; formyl; $C_2$–$C_6$ alkylcarbonyl; $C_2$–$C_6$ alkoxycarbonyl; NH$_2$C(O); (C$_1$–C$_4$ alkyl)NHC(O); (C$_1$–C$_4$ alkyl)$_2$NC(O); Si(R$^{25}$)$_3$; Ge(R$^{25}$)$_3$; (R$^{25}$)$_3$Si—C≡C—; or phenyl, phenylethynyl, benzoyl, or phenylsulfonyl each substituted with $R^8$ and optionally substituted with one or more $R^{10}$;

$R^5$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

Y is —O—; —S(O)$_n$—; —NR$^{15}$—; —C(=O)—; —CH(OR$^{15}$)—; —CHR$^6$—; —CHR$^6$CHR$^6$—; —CR$^6$=CR$^6$—; —C≡C—; —CHR$^{15}$O—; —OCHR$^{15}$—; —CHR$^{15}$S(O)$_n$—; —S(O)$_n$CHR$^{15}$—; —CHR$^{15}$O—N=C(R$^7$)—; —(R$^7$)C=N—OCH(R$^{15}$)—; —C(R$^7$)=N—O—; —O—N=C(R$^7$)—; —CHR$^{15}$OC(=O)N(R$^{15}$)—; —CHR$^{15}$OC(=S)N(R$^{15}$)—; —CHR$^{15}$OC(=O)O—; —CHR$^{15}$OC(=S)O—; —CHR$^{15}$OC(=O)S—; —CHR$^{15}$OC(=S)S—; —CHR$^{15}$SC(=O)N(R$^{15}$)—; —CHR$^{15}$SC(=S)N(R$^{15}$)—; —CHR$^{15}$SC(=O)O—; —CHR$^{15}$SC(=S)O—; —CHR$^{15}$SC(=O)S—; —CHR$^{15}$SC(=S)S—; —CHR$^{15}$SC(=NR$^{15}$)S—; —CHR$^{15}$N(R$^{15}$)C(=O)N(R$^{15}$)—; —CHR$^{15}$O—N(R$^{15}$)C(=O)N(R$^{15}$)—; —CHR$^{15}$O—N(R$^{15}$)C(=S)N(R$^{15}$)—; —CHR$^{15}$O—N=C(R$^7$)NR$^{15}$—; —CHR$^{15}$O—N=C(R$^7$)OCH$_2$—; —CHR$^{15}$O—N=C(R$^7$)—N=N—; —CHR$^{15}$O—N=C(R$^7$)—C(=O)—; —CHR$^{15}$O—N=C(R$^7$)—C(=N—A$^2$—Z$^1$)—A$^1$—; —CHR$^{15}$O—N=C(R$^7$)—C(R$^7$)=N—A$^2$—A$^3$—; —CHR$^{15}$O—N=C(—C(R$^7$)=N—A$^2$—Z$^1$)—; —CHR$^{15}$O—N=C(R$^7$)—CH$_2$O—; —CHR$^{15}$O—N=C(R$^7$)—CH$_2$S—; —O—CH$_2$CH$_2$O—N=C(R$^7$)—; —CHR$^{15}$O—C(R$^{15}$)=C(R$^7$)—; —CHR$^{15}$O—C(R$^7$)=N—; —CHR$^{15}$S—C(R$^7$)=N—; —C(R$^7$)=N—NR$^{15}$—; —CH=N—N=C(R$^7$)—; —CHR$^{15}$N(R$^{15}$)—N=C(R$^7$)—; —CHR$^{15}$N(COCH$_3$)—N=C(R$^7$)—; —OC(=S)NR$^{15}$C(=O)—; —CHR$^6$—C(=W$^1$)—A$^1$—; —CHR$^6$CHR$^6$—C(=W$^1$)—A$^1$—; —CR$^6$=CR$^6$—C(=W$^1$)—A$^1$—; —C≡C—C(=W$^1$)—A$^1$—; —N=CR$^6$—C(=W$^1$)—A$^1$—; or a direct bond; and the directionality of the Y linkage is defined such that the moiety depicted on the left side of the linkage is bonded to E and the moiety on the right side of the linkage is bonded to Z;

$Z^1$ is H or —A$^3$—Z;

$W^1$ is O or S;

$A^1$ is O; S; NR$^{15}$; or a direct bond;

$A^2$ is O; NR$^{15}$; or a direct bond;

$A^3$ is —C(=O)—; —S(O)$_2$—; or a direct bond;

each $R^6$ is independently H; 1–2 CH$_3$; $C_2$–$C_3$ alkyl; $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; NH$_2$C(O)NH; (C$_1$–C$_3$ alkyl)NHC(O)NH; (C$_1$–C$_3$ alkyl)$_2$NC(O)NH; N(C$_1$–C$_3$ alkyl)$_2$; piperidinyl; morpholinyl; 1–2 halogen; cyano; or nitro;

each $R^7$ is independently H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; halogen; cyano; nitro; hydroxy; amino; NH(C$_1$–C$_6$ alkyl); N(C$_1$–C$_6$ alkyl)$_2$; or morpholinyl;

each Z is independently selected from:

i) $C_1$–$C_{10}$ alkyl, $C_2$–$C_{10}$ alkenyl, and $C_2$–$C_{10}$ alkynyl each substituted with $R^9$ and optionally substituted with one or more $R^{10}$;

ii) $C_3$–$C_8$ cycloalkyl, $C_3$–$C_8$ cycloalkenyl and phenyl each substituted with $R^9$ and optionally substituted with one or more $R^{10}$;

iii) a ring system selected from 3 to 14-membered monocyclic, fused bicyclic and fused tricyclic nonaromatic heterocyclic ring systems and 5 to 14-membered monocyclic, fused bicyclic and fused tricyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each nonaromatic or aromatic heterocyclic ring system substituted with $R^9$ and optionally substituted with one or more $R^{10}$;

iv) a multicyclic ring system selected from 8 to 14membered fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$, and any remaining rings as aromatic carbocyclic rings, each multicyclic ring system substituted with $R^9$ and optionally substituted with one or more $R^{10}$; and v) adamantyl substituted with $R^9$ and optionally substituted with one or more $R^{10}$;

each Q is independently selected from the group —$CHR^{13}$—, —$NR^{13}$—, —O—, and —$S(O)_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); $NH(C_1$–$C_6$ alkyl); $N(C_1$–$C_6$ alkyl)$_2$; cyano; nitro; $SiR^{19}R^{20}R^{21}$; or $GeR^{19}R^{20}R^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2$ ($C_1$–$C_6$ alkyl); $NH(C_1$–$C_6$ alkyl); $N(C_1$–$C_6$ alkyl)$_2$; —$C(R^{18})$=$NOR^{17}$; cyano; nitro; $SF_5$; $SiR^{22}R^{23}R^{24}$; or $GeR^{22}R^{23}R^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ can be taken together as —$OCH_2O$— or —$OCH_2CH_2O$—; each $CH_2$ group of said taken together $R^9$ and $R^{10}$ optionally substituted with 1–2 halogen; or when Y and an $R^{10}$ are attached to adjacent atoms on Z and Y is —$CHR^{15}O$—N=$C(R^7)$—, —O—N=C($R^7$)—, —O—$CH_2CH_2O$—N=$C(R^7)$—, —$CHR^{15}O$—$C(R^{15})$=$C(R^7)$—, —CH=N—N=C($R^7$)—, —$CHR^{15}N(R^{15})$—N=$C(R^7)$— or —$CHR^{15}N(COCH_3)$—N=$C(R^7)$—, $R^7$ and said adjacently attached $R^{10}$ can be taken together as —$(CH_2)_r$-J- such that J is attached to Z;

J is —$CH_2$—; —$CH_2CH_2$—; —$OCH_2$—; —$CH_2O$—; —$SCH_2$—; —$CH_2S$—; —$N(R^{16})CH_2$—; or —$CH_2N(R^{16})$—; each $CH_2$ group of said J optionally substituted with 1 to 2 $CH_3$;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; $Si(R^{25})_3$; or $Ge(R^{25})_3$;

each $R^{13}$ is independently H; $C_1$–$C_6$ alkyl; $C_1$–$C_6$ haloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl;

each $R^{15}$ is independently H; $C_1$–$C_3$ alkyl; $C_3$–$C_6$ cycloalkyl; or phenyl or benzyl, each optionally substituted on the phenyl ring with halogen, $C_1$–$C_4$ alkyl, $C_1$–$C_4$ haloalkyl, $C_1$–$C_4$ alkoxy, $C_1$–$C_4$ haloalkoxy, nitro or cyano; or when Y is —$CHR^{15}N(R^{15})C$(=O)$N(R^{15})$—, the two $R^{15}$ attached to nitrogen atoms on said group can be taken together as —$(CH_2)_s$—; or when Y is —$CHR^{15}O$—N=$C(R^7)NR^{15}$—, $R^7$ and the adjacently attached $R^{15}$ can be taken together as —$CH_2$—$(CH_2)_s$—; —O—$(CH_2)_s$—; —S—$(CH_2)_s$—; or —$N(C_1$–$C_3$ alkyl)—$(CH_2)_s$—; with the directionality of said linkage defined such that the moiety depicted on the left side of the linkage is bonded to the carbon and the moiety on the right side of the linkage is bonded to the nitrogen;

$R^{16}$, $R^{17}$, and $R^{18}$ are each independently H; $C_1$–$C_3$ alkyl; $C_3$–$C_6$ cycloalkyl; or phenyl optionally substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{19}$, $R^{20}$, $R^{21}$, $R^{22}$, $R^{23}$, and $R^{24}$ are each independently $C_1$–$C_6$ alkyl; $C_2$–$C_6$ alkenyl; $C_1$–$C_4$ alkoxy; or phenyl;

each $R^{25}$ is independently $C_1$–$C_4$ alkyl; $C_1$–$C_4$ haloalkyl; $C_2$–$C_4$ alkenyl; $C_1$–$C_4$ alkoxy; or phenyl;

m, n and p are each independently 0, 1 or 2;

r is 0 or 1; and s is 2 or 3.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 $CH_3$" indicates that the substituent can be methyl or, when there is a hydrogen attached to the same atom, the substituent and said hydrogen can both be methyl. "Alkenyl" includes straight-chain or branched alkenes such as vinyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy" includes straight-chain or branched alkenyloxy moieties. Examples of "alkenyloxy" include $H_2C$=$CHCH_2O$, ($CH_3$)$_2C$=$CHCH_2O$, ($CH_3$)$CH$=$CHCH_2O$, ($CH_3$)$CH$=$C(CH_3)CH_2O$ and $CH_2$=$CHCH_2CH_2O$. "Alkynyloxy" includes straight-chain or branched alkynyloxy moieties. Examples of "alkynyloxy" include $HC$≡$CCH_2O$, $CH_3C$≡$CCH_2O$ and $CH_3C$≡$CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, ($CH_3$)$_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, ($CH_3$)$_2CHS(O)_2$ and the different butylsulfonyl, pentylsulfonyl and hexylsulfonyl isomers. "Cycloalkyl" includes, for example, cyclopropyl, cyclobutyl, cyclopentyl, and cyclohexyl. "Cycloalkenyl" includes groups such as cyclopentenyl and cyclohexenyl as well as groups with more than one double bond such as 1,3- and 1,4-cyclohexadienyl. The term "aromatic carbocyclic ring system" includes fully aromatic carbocycles and carbocycles in which at least one ring of a polycyclic ring system is aromatic (where aromatic indicates that the Hückel rule is satisfied). The term "nonaromatic carbocyclic ring system" denotes fully saturated carbocycles as well as partially or fully unsaturated carbocycles where the Hückel rule is not satisfied by any of the rings in the ring system. The term "aromatic heterocyclic ring system" includes fully aromatic heterocycles and heterocycles in which at least one ring of a polycyclic ring system is aromatic (where aromatic indicates that the Hückel rule is satisfied). The term "nonaromatic heterocyclic ring system" denotes fully saturated heterocycles as well as partially or fully unsaturated heterocycles where the Hückel rule is not satisfied by any of the rings in the ring system. The heterocyclic ring systems can be attached through any available carbon or nitrogen by replacement of a hydrogen on said carbon or nitrogen. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides.

The term "halogen", either alone or in compound words such as "haloalkyl", includes fluorine, chlorine, bromine or iodine. The term "1–2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$–$C_j$" prefix where i and j are numbers from 1 to 10. For example, $C_1$–$C_3$ alkylsulfonyl designates methylsulfonyl through propylsulfonyl. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a group contains a substituent which can be hydrogen, for example $R^9$ or $R^{13}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a phenol.

Preferred compounds for reasons of better activity and/or ease of synthesis are:

Preferred 1. Compounds of Formula I above, and N-oxides and agriculturally suitable salts thereof, wherein:

E is selected from the group 1H-pyrrole-1,2-, 2,3- and 3,4-diyl; 2,3- and 3,4-furandiyl; 2,3- and 3,4-thiophenediyl; 1H-pyrazole-1,5-, 3,4- and 4,5-diyl; 1H-imidazole-1,2-, 4,5- and 1,5-diyl; 3,4- and 4,5-isoxazolediyl; 4,5-oxazolediyl; 3,4- and 4,5-isothiazolediyl; 4,5-thiazolediyl; 1H-1,2,3-triazole-1,5- and 4,5-diyl; 2H-1,2,3-triazole-4,5-diyl; 1H-1,2,4-triazole-1,5-diyl; 4H-1,2,4-triazole-3,4-diyl; 1,2,3-oxadiazole-4,5-diyl; 1,2,5-oxadiazole-3,4-diyl; 1,2,3-thiadiazole-4,5-diyl; 1,2,5-thiadiazole-3,4-diyl; 1H-tetrazole-1,5-diyl; 2,3- and 3,4-pyridinediyl; 3,4- and 4,5-pyridazinediyl; 4,5-pyrimidinediyl; 2,3-pyrazinediyl; 1,2,3-triazine-4,5-diyl; 1,2,4-triazine-5,6-diyl; 1H-indole-1,4-, 1,5-, 1,6-, 1,7-, 2,4-, 2,5-, 2,6-, 2,7-, 3,4-, 3,5-, 3,6-, 3,7-, 1,2-, 2,3-, 4,5-, 5,6- and 6,7-diyl; 2,4-, 2,5-, 2,6-, 2,7-, 3,4-, 3,5-, 3,6-, 3,7-, 2,3-, 4,5-, 5,6- and 6,7-benzofurandiyl; benzo[b]thiophene-2,4-, 2,5-, 2,6-, 2,7-, 3,4-, 3,5-, 3,6-, 3,7-, 2,3-, 4,5-, 5,6- and 6,7-diyl; 1H-indazole-1,4-, 1,5-, 1,6-, 1,7-, 3,4-, 3,5-, 3,6-, 3,7-, 4,5-, 5,6- and 6,7-diyl; 1H-benzimidazole-1,4-, 1,5-, 1,6-, 1,7-, 2,4-, 2,5-, 2,6-, 2,7-, 4,5-, 5,6- and 6,7-diyl; 1,2-benzisoxazole-3,4-, 3,5-, 3,6-, 3,7-, 4,5-, 5,6- and 6,7-diyl; 2,4-, 2,5-, 2,6-, 2,7-, 4,5-, 5,6- and 6,7-benzoxazolediyl; 1,2-benzisothiazole-3,4-, 3,5-, 3,6-, 3,7-, 4,5-, 5,6- and 6,7-diyl; 2,4-, 2,5-, 2,6-, 2,7-, 4,5-, 5,6- and 6,7-benzothiazolediyl; 2,5-, 2,6-, 2,7-, 2,8-, 3,5-, 3,6-, 3,7-, 3,8-, 4,5-, 4,6-, 4,7-, 4,8-, 2,3-, 3,4-, 5,6-, 6,7- and 7,8-quinolinediyl; 1,5-, 1,6-, 1,7-, 1,8-, 3,5-, 3,6-, 3,7-, 3,8-, 4,5-, 4,6-, 4,7-, 4,8-, 3,4-, 5,6-, 6,7- and 7,8-isoquinolinediyl; 3,5-, 3,6-, 3,7-, 3,8-, 4,5-, 4,6-, 4,7-, 4,8-, 3,4-, 5,6-, 6,7- and 7,8-cinnolinediyl; 1,5-, 1,6-, 1,7-, 1,8-, 5,6-, 6,7- and 7,8-phthalazinediyl; 2,5-, 2,6-, 2,7-, 2,8-, 4,5-, 4,6-, 4,7-, 4,8-, 5,6-, 6,7- and 7,8-quinazolinediyl; 2,5-, 2,6-, 2,7-, 2,8-, 2,3-, 5,6-, 6,7- and 7,8-quinoxalinediyl; 1,8,-naphthyridine-2,5-, 2,6-, 2,7-, 3,5-, 3,6-, 4,5-, 2,3- and 3,4-diyl; 2,6-, 2,7-, 4,6-, 4,7-, 6,7-pteridinediyl; pyrazolo[5,1-b]thiazole-2,6-, 2,7-, 3,6-, 3,7-, 2,3- and 6,7-diyl; thiazolo[2,3-c]-1,2,4-triazole-2,5-, 2,6-, 5,6-diyl; 2-oxo-1,3-benzodioxole-4,5- and 5,6-diyl; 1,3-dioxo-1H-isoindole-2,4-, 2,5-, 4,5- and 5,6-diyl; 2-oxo-2H-1-benzopyran-3,5-, 3,6-, 3,7-, 3,8-, 4,5-, 4,6-, 4,7-, 4,8-, 5,6-, 6,7- and 7,8-diyl; [1,2,4]triazolo[1,5-a]pyridine-2,5-, 2,6-, 2,7-, 2,8-, 5,6-, 6,7- and 7,8-diyl; 3,4-dihydro-2,4-dioxo-2H-1,3-benzoxazine-3,5-, 3,6-, 3,7-, 3,8-, 5,6-, 6,7- and 7,8-diyl; 2,3-dihydro-2-oxo-3,4-, 3,5-, 3,6-, 3,7-, 4,5-, 5,6- and 6,7-benzofurandiyl; thieno[3,2-d]thiazole-2,5-, 2,6-, and 5,6-diyl; 5,6,7,8-tetrahydro-2,5-, 2,6-, 2,7-, 2,8-, 3,5-, 3,6-, 3,7-, 3,8-, 4,5-, 4,6-, 4,7-, 4,8-, 2,3- and 3,4quinolinediyl; 2,3-dihydro-1,1,3-trioxo-1,2-benzisothiazole-2,4-, 2,5-, 2,6-, 2,7-, 4,5-, 5,6- and 6,7-diyl; 1,3-benzodioxole-2,4-, 2,5-, 4,5- and 5,6-diyl; 2,3-dihydro-2,4-, 2,5-, 2,6-, 2,7-, 3,4-, 3,5-, 3,6-, 3,7-, 4,5-, 5,6- and 6,7-benzofurandiyl; 2,3-dihydro-1,4-benzodioxin-2,5-, 2,6-, 2,7-, 2,8-, 5,6- and 6,7-diyl; 5,6,7,8-tetrahydro-4H-cyclohepta[b]thiophene-2,4-, 2,5-, 2,6-, 2,7-, 2,8-, 3,4-, 3,5-, 3,6-, 3,7-, 3,8-, and 2,3-diyl; and 1,5-, 1,6-, 1,7-, 1,8-, 2,6-, 2,7-, 1,2-, and 2,3-naphthalenediyl; each aromatic ring system optionally substituted with one of $R^3$, $R^4$, or both $R^3$ and $R^4$;

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently halogen; cyano; nitro; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfonyl; $C_2$–$C_6$ alkylcarbonyl; $C_2$–$C_6$ alkoxycarbonyl; ($C_1$–$C_4$ alkyl)NHC(O); ($C_1$–$C_4$ alkyl)$_2$NC(O); benzoyl; or phenylsulfonyl;

Y is —O—; —CH=CH—; —C≡C—; —CH$_2$O—; —OCH$_2$—; —CH$_2$S(O)$_n$—; —CH$_2$O—N=C($R^7$)—; —($R^7$)C=N—OCH($R^{15}$)—; —C($R^7$)=N—O—; —CH$_2$OC(O)NH—; —CH$_2$S—C($R^7$)=N—; —CH=C$R^6$—C(=$W^1$)—$A^1$—; or a direct bond;

$R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; $C_3$–$C_6$ cycloalkyl; halogen; or cyano; or when Y and an $R^{10}$ are attached to adjacent atoms on Z and Y is —CH$_2$O—N=C($R^7$)—, $R^7$ and said adjacently attached $R^{10}$ can be taken together as —(CH$_2$)$_r$-J- such that J is attached to Z;

Z is selected from the group $C_1$–$C_{10}$ alkyl; $C_3$–$C_8$ cycloalkyl; phenyl; naphthalenyl; anthracenyl; phenanthrenyl; 1H-pyrrolyl; furanyl; thienyl; 1H-pyrazolyl; 1H-imidazolyl; isoxazolyl; oxazolyl; isothiazolyl; thiazolyl; 1H-1,2,3-triazolyl; 2H-1,2,3-triazolyl; 1H-1,2,4-triazolyl; 4H-1,2,4-triazolyl; 1,2,3-oxadiazolyl; 1,2,4-oxadiazolyl; 1,2,5-oxadiazolyl; 1,3,4-oxadiazolyl; 1,2,3-thiadiazolyl; 1,2,4-thiadiazolyl; 1,2,5-thiadiazolyl; 1,3,4-thiadiazolyl; 1H-tetrazolyl; 2H-tetrazolyl; pyridinyl; pyridazinyl; pyrimidinyl; pyrazinyl; 1,3,5-triazinyl; 1,2,4-triazinyl; 1,2,4,5-tetrazinyl; 1H-indolyl; benzofuranyl; benzo[b]thiophenyl; 1H-indazolyl; 1H-benzimidazolyl; benzoxazolyl; benzothiazolyl; quinolinyl; isoquinolinyl; cinnolinyl; phthalazinyl; quinazolinyl; quinoxalinyl; 1,8-naphthyridinyl; pteridinyl; 2,3-dihydro-1H-indenyl; 1,2,3,4-tetrahydronaphthalenyl; 6,7,8,9-tetrahydro-5H-benzocycloheptenyl; 5,6,7,8,9,10-hexahydrobenzocyclooctenyl; 2,3-dihydro-3-oxobenzofuranyl; 1,3-dihydro-1-oxoisobenzofiranyl; 2,3-dihydro-2-oxobenzofuranyl; 3,4-dihydro-4-oxo-2H-1-benzopyranyl; 3,4-dihydro-1-oxo-1H-2-benzopyranyl; 3,4dihydro-3-oxo-1H-2-benzopyranyl; 3,4-dihydro-2-oxo-2H-1-benzopyranyl; 4-oxo-4H-1-benzopyranyl; 2-oxo-2H-1-benzopyranyl; 2,3,4,5-tetrahydro-5-oxo-1-benzoxepinyl; 2,3,4,5-tetrahydro-2-oxo-1-benzoxepinyl; 2,3-dihydro-1,3-dioxo-1H-isoindolyl; 1,2,3,4-tetrahydro-1,3dioxoisoquinolinyl; 3,4-dhydro-2,4-dioxo-2H-1,3-benzoxazinyl; 2-oxo-1,3-benzodioxyl; 2,3-dihydro-1,1,3-trioxo-1,2-benzisothiazolyl; 9H-fluorenyl; azulenyl; and thiazolo[2,3-c]-1,2,4-triazolyl; each group substituted with $R^9$ and optionally substituted with one or more $R^{10}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; CO$_2$($C_1$–$C_6$ alkyl); NH($C_1$–$C_6$ alkyl); N($C_1$–$C_6$ alkyl)$_2$; Si$R^{22}R^{23}R^{24}$; or Ge$R^{22}R^{23}R^{24}$; or $R^9$ is $C_3$–$C_6$ cycloalkyl, phenyl, phenoxy, pyridinyl, pyridinyloxy, pyrimidinyl, or pyrinidinyloxy, each optionally substituted with one of $R^{11}$, $R^{12}$, or both $R^{11}$ and $R^{12}$; and each $R^{15}$ is independently H; $C_1$–$C_3$ alkyl; or $C_3$–$C_6$ cycloalkyl.

Preferred 2. Compounds of Preferred 1 wherein:

E is selected from the group 2,3- and 3,4-furandiyl; 2,3- and 3,4-thiophenediyl; 2,3- and 3,4-pyridinediyl; 4,5-pyrimidinediyl; 2,4-, 2,7-, 3,5-, 2,3-, 4,5-, 5,6- and 6,7-benzofurandiyl; benzo[b]thiophene-2,4-, 2,7-, 3,5-, 2,3-, 4,5-, 5,6- and 6,7-diyl; and 1,6-, 1,7-, 1,2-, and 2,3-naphthalenediyl; each aromatic ring system optionally substituted with one of $R^3$, $R^4$, or both $R^3$ and $R^4$;

Z is selected from the group phenyl; 1,2,4-thiadiazolyl; pyridinyl; pyrimidinyl; and naphthalenyl; each group substituted with $R^9$ and optionally substituted with one or more $R^{10}$;

$R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; cyclopropyl; halogen; or cyano; or when Y and an $R^{10}$ are attached to adjacent atoms on Z and Y is —CH$_2$O—N=C($R^7$)—, $R^7$ and said adjacently attached $R^{10}$ can be taken together as —(CH$_2$)$_r$-J- such that J is attached to Z;

J is —CH$_2$— or —CH$_2$CH$_2$—; and r is 1.

Preferred 3. Compounds of Preferred 2 wherein:

A is O; N; N$R^5$; or C$R^{14}$;

X is O$R^1$;

$R^1$ is $C_1$–$C_3$ alkyl;

$R^2$ is H or $C_1$–$C_2$ alkyl;

Y is —O—; —CH=CH—; —CH$_2$O—; —CH$_2$O—N=C($R^7$)—; —($R^7$)C=N—OCH($R^{15}$)—; —CH$_2$OC(=O)NH—; —CH$_2$S—C($R^7$)=N—; or —CH=C$R^6$—C(=$W^1$)—$A^1$—;

$R^7$ is H; $C_1$–$C_3$ alkyl; $C_1$–$C_3$ haloalkyl; $C_1$–$C_3$ alkoxy; $C_1$–$C_3$ alkylthio; or cyclopropyl; and each $R^{15}$ is independently H; $C_1$–$C_3$ alkyl; or cyclopropyl.

Preferred 4. Compounds of Preferred 3 wherein:

A is O or N$R^5$;

G is C; and

Y is —O—; —CH$_2$O—; or —CH$_2$O—N=C($^7$)—.

Preferred 5. Compounds of Preferred 4 wherein:

$R^1$ is methyl; and $R^2$ is methyl.

Preferred 6. Compounds of Preferred 3 wherein:

A is N or C$R^{14}$;

G is N; and

Y is —O—; —CH$_2$O—; or —CH$_2$O—N=C$R^7$)—.

Preferred 7. Compounds of Preferred 6 wherein:

$R^1$ is methyl; and $R^2$ is methyl.

Most preferred are compounds of Preferred 3 selected from the group:

2,4-dihydro-5-methoxy-2-methyl-4-[2-[[[[1-[3-(trimethylsilyl)phenyl]ethylidene]amino]oxy]methyl]-3-thienyl]-3H-1,2,4-triazol-3-one;

2,4-dihydro-5-methoxy-2-methyl-4-[2-[[[[ 1-[3-(trifluoromethyl)phenyl]ethylidene]amino]oxy]methyl]-3-thienyl]-3H-1,2,4-triazol-3-one;

4-[2-[(2,5-dimethylphenoxy)methyl]-3-thienyl]-2,4-dihydro-5-methoxy-2-methyl-3H-1,2,4-triazol-3-one;

(1,1-dimethylethyl) 2-chloro-3-[3-(1,5-dihydro-3-methoxy-1-methyl-5-oxo-4H-1,2,4-triazol-4-yl)-2-thienyl]-2-propenoate;

4-[2-[[[3-(4-chlorophenyl)-1,2,4-thiadiazol-5-yl]oxy]methyl]-3-thienyl]-2,4-dihydro-5-methoxy-2-methyl-3H-1,2,4-triazol-3-one; and 2,4-dihydro-5-methoxy-2-methyl-4-[2-[[[3-[4-(trifluoromethyl)phenyl]-1,2,4-thiadiazol-5-yl]oxy]methyl]-3-thienyl]-3H-1,2,4-triazol-3-one.

This invention also relates to fungicidal compositions comprising fungicidally effective amounts of the compounds of the invention and at least one of a surfactant, a solid diluent or a liquid diluent. The preferred compositions of the present invention are those which comprise the above preferred compounds.

This invention also relates to a method for controlling plant diseases caused by fungal plant pathogens comprising applying to the plant or portion thereof, or to the plant seed or seedling, a fungicidally effective amount of the compounds of the invention (e.g., as a composition described herein). The preferred methods of use are those involving the above preferred compounds.

Of note are embodiments where E is a naphthalene ring, provided that when G and Y are attached to the same ring, then G and Y are attached to adjacent ring members, the naphthalene ring optionally substituted with one of $R^3$, $R^4$, or both $R^3$ and $R^4$, provided that when G is attached to the 1, 4, 5, or 8 position of the naphthalene ring, then Y is other than —O—, —S(O)$_n$—, —C(=O)—, —CHR$^6$—, —CHR$^6$CHR$^6$—, —CR$^6$=CR$^6$—, —C≡C—, —OCHR$^{15}$—, —S(O)$_n$CHR$^{15}$— or a direct bond; embodiments where $R^2$ is H, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_2$–$C_4$ alkylcarbonyl or $C_2$–$C_4$ alkoxycarbonyl; embodiments where Y is —O—, —S(O)$_n$—, —NR$^{15}$—, —C(=O)—, —CH(OR$^{15}$)—, —CHR$^6$—, —CHR$^6$CHR$^6$—, —CR$^6$=CR$^6$—, —C≡C—, —CHR$^{15}$O—, —OCHR$^{15}$—, —CHR$^{15}$S(O)$_n$—, —S(O)$_n$CHR$^{15}$—, —CHR$^{15}$O—N=C(R$^7$)—, —(R$^7$)C=N—OCH(R$^{15}$)—, —C(R$^7$)=N—O—, —O—N=C(R$^7$)—, —CHR$^{15}$OC(=O)N(R$^{15}$)—, —CHR$^{15}$OC(=S)N(R$^{15}$)—, —CHR$^{15}$O—N(R$^{15}$)C(=O)N(R$^{15}$)—, —CHR$^{15}$O—N(R$^{15}$)C(=S)N(R$^{15}$)—, —CHR$^{15}$O—N=C(R$^7$)NR$^{15}$—, —CHR$^{15}$O—N=C(R$^7$)OCH$_2$—, —CHR$^{15}$O—N=C(R$^7$)—N=N—, —CHR$^{15}$O—N=C(R$^7$)—C(=O)—, —CHR$^{15}$S—C(R$^7$)=N—, —C(R$^7$)=N—NR$^{15}$—, —CH=N—N=C(R$^7$)—, —CHR$^{15}$N(COCH$_3$)—N=C(R$^7$)—, —OC(=S)NR$^{15}$C(=O)—, —CHR$^6$—C(=W$^1$)—A$^1$—, —CHR$^6$CHR$^6$—C(=W$^1$)—A$^1$—, —CR$^6$CR$^6$—C(=W$^1$)—A$^1$—, —C≡C—C(=W$^1$)—A$^1$—, —N=CR$^6$—C(=W$^1$)—A$^1$— or a direct bond; embodiments where $R^7$ is H, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, $C_1$–$C_6$ haloalkylthio, $C_1$–$C_6$ haloalkylsulfinyl, $C_1$–$C_6$ haloalkylsulfonyl, $C_2$–$C_6$ alkenyl, $C_2$–$C_6$ haloalkenyl, $C_2$–$C_6$ alkynyl, $C_2$–$C_6$ haloalkynyl, $C_3$–$C_6$ cycloalkyl, $C_2$–$C_4$ alkylcarbonyl, $C_2$–$C_4$ alkoxycarbonyl, halogen, cyano or morpholinyl; embodiments where Z is other than $C_3$–$C_8$ cycloalkenyl and adamantyl each substituted with $R^9$ and optionally substituted with one or more $R^{10}$; embodiments where, when Y and an $R^{10}$ are attached to adjacent atoms on Z and Y is —CHR$^{15}$O—N=C(R$^7$)—, —O—N=C(R$^7$)—, —CH=N—N=C(R$^7$)— or —CHR$^{15}$N(COCH$_3$)—N=C(R$^7$)—, $R^7$ and said adjacently attached $R^{10}$ are taken together as —(CH$_2$)$_r$—J— such that J is attached to Z; embodiments where $R^{19}$, $R^{20}$, $R^{21}$, $R^{22}$, $R^{23}$, and $R^{24}$ are each independently $C_1$–$C_6$ alkyl, $C_1$–$C_4$ alkoxy or phenyl; embodiments where each $R^{25}$ is independently $C_1$–$C_4$ alkyl or phenyl; embodiments where $R^3$ and $R^4$ are each independently halogen, cyano, nitro, $C_1$–$C_6$ alkyl, $C_1$–$C_6$ haloalkyl, $C_1$–$C_6$ alkoxy, $C_1$–$C_6$ haloalkoxy, $C_1$–$C_6$ alkylsulfonyl, $C_2$–$C_6$ alkylcarbonyl, $C_2$–$C_6$ alkoxycarbonyl, ($C_1$–$C_4$ alkyl)NHC(O), ($C_1$–$C_4$ alkyl)$_2$NC(O), benzoyl or phenylsulfonyl; and embodiments where Z is selected from the group phenyl, pyridinyl, pyrimidinyl and naphthalenyl, each group substituted with $R^9$ and optionally substituted with one or more $R^{10}$.

The compounds of Formula I can be prepared by one or more of the following methods and variations as described in Schemes 1–33. The definitions of E, A, G, W, X, $R^1$–$R^{25}$, Y, $Z^1$, $W^1$, $A^1$–$A^3$, Z, Q, J, m, n, p, r and s in the compounds of Formulae 1–58 below are as defined above in the Summary of the Invention. Compounds of Formulae Ia–Io are various subsets of the compounds of Formula I, and all substituents for Formulae Ia–Io are as defined above for Formula I.

One skilled in the art will recognize that some compounds of Formula I can exist in one or more tautomeric forms. For example, a compound of Formula I wherein $R^2$ is H may exist as tautomer Ia or Ib, or both Ia and Ib. The present invention comprises all tautomeric forms of compounds of Formula I.

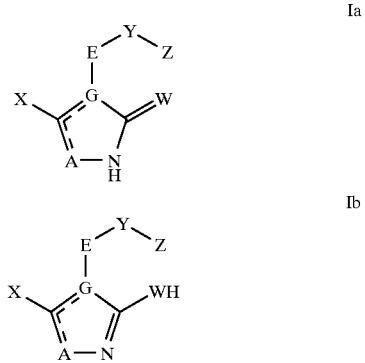

The compounds of Formula I can be prepared as described below in Procedures 1) to 5). Procedures 1) to 4) describe syntheses involving construction of the amide ring after the formation of the aryl moiety (E-Y-Z). Procedure 5) describes syntheses of the aryl moiety (E-Y-Z) with the amide ring already in place.

1) Alkylation Procedures

The compounds of Formula I are prepared by treating compounds of Formula 1 with an appropriate alkyl transfer reagent in an inert solvent with or without additional acidic or basic reagents or other reagents (Scheme 1). Suitable solvents are selected from the group consisting of polar aprotic solvents such as acetonitrile, dimethylformamide or dimethyl sulfoxide; ethers such as tetrahydrofuran, dimethoxyethane, or diethyl ether; ketones such as acetone or 2-butanone; hydrocarbons such as toluene or benzene; and halocarbons such as dichloromethane or chloroform.

Scheme 1

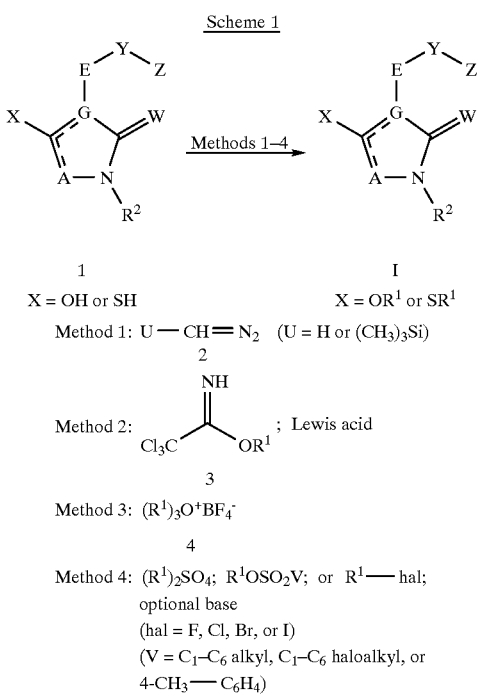

For example, compounds of Formula I can be prepared by the action of diazoalkane reagents of Formula 2 such as diazomethane (U=H) or trimethylsilyldiazomethane (U=(CH$_3$)$_3$Si) on dicarbonyl compounds of Formula 1 (Method 1). Use of trimethylsilyldiazomethane requires a protic cosolvent such as methanol. For examples of these procedures, see *Chem. Pharm. Bull.*, (1984), 32, 3759.

As indicated in Method 2, compounds of Formula I can also be prepared by contacting carbonyl compounds of Formula 1 with alkyl trichloroacetimidates of Formula 3 and a Lewis acid catalyst. Suitable Lewis acids include trimethylsilyl triflate and tetrafluoroboric acid. The alkyl trichloroacetimidates can be prepared from the appropriate alcohol and trichloroacetonitrile as described in the literature (J. Danklmaier and H. Hönig, *Synth. Commun.*, (1990), 20, 203).

Compounds of Formula I can also be prepared from compounds of Formula 1 by treatment with a trialkyloxonium tetrafluoroborate (i.e., Meerwein's salt) of Formula 4 (Method 3). The use of trialkyloxonium salts as powerful alkylating agents is well known in the art (see U. Schöllkopf, U. Groth, C. Deng, *Angew. Chem., Int. Ed. Engl.*, (1981), 20, 798).

Other alkylating agents which can convert carbonyl compounds of Formula 1 to compounds of Formula I are dialkyl sulfates such as dimethyl sulfate, haloalkyl sulfonates such as methyl trifluoromethanesulfonate, and alkyl halides such as iodomethane and propargyl bromide (Method 4). These alkylations can be conducted with or without additional base. Appropriate bases include alkali metal alkoxides such as potassium tert-butoxide, inorganic bases such as sodium hydride and potassium carbonate, or tertiary amines such as triethylamine, pyridine, 1,8-diazabicyclo[5.4.0]undec-7ene (DBU), and triethylenediamine. See R. E. Benson, T. L. Cairns, *J. Am. Chem. Soc.*, (1948), 70, 2115 for alkylation examples using agents of this type.

Compounds of Formula 1a (compounds of Formula 1 wherein G=C, W=O and X=OH) can be prepared by condensation of malonates or malonate derivatives of Formula 5 with an ambident nucleophile of Formula 6 (Scheme 2). The nucleophiles of Formula 6 are N-substituted hydroxylamines (HO—NHR$^2$) and substituted hydrazines (HN(R$^5$)—NHR$^2$). Examples of such nucleophiles are N-methylhydroxylamine and methylhydrazine. The malonate esters of Formula 5 can be prepared by methods described hereinafter. The esters of Formula 5 can also be activated by first hydrolyzing the ester to form the corresponding carboxylic acid, and then converting the acid into the acid chloride (T=Cl) using thionyl chloride or oxalyl chloride, or into the acyl imidazole (T=1-imidazolyl) by treating with 1,1'-carbonyldiimidazole. Compounds of Formula 1aa can be prepared by reaction of nitrile esters of Formula 5b with ambident nucleophiles of Formula 6. See M. Scobie and G. Tennant, *J. Chem. Soc., Chem. Comm.*, (1994), 2451. Alkylation of 1aa with alkyl halides in the presence of base provides compounds of Formula 1ab. Alternatively, treatment of 1aa with alkylamines or alkoxyamines provides compounds of Formula 1ab.

Scheme 2

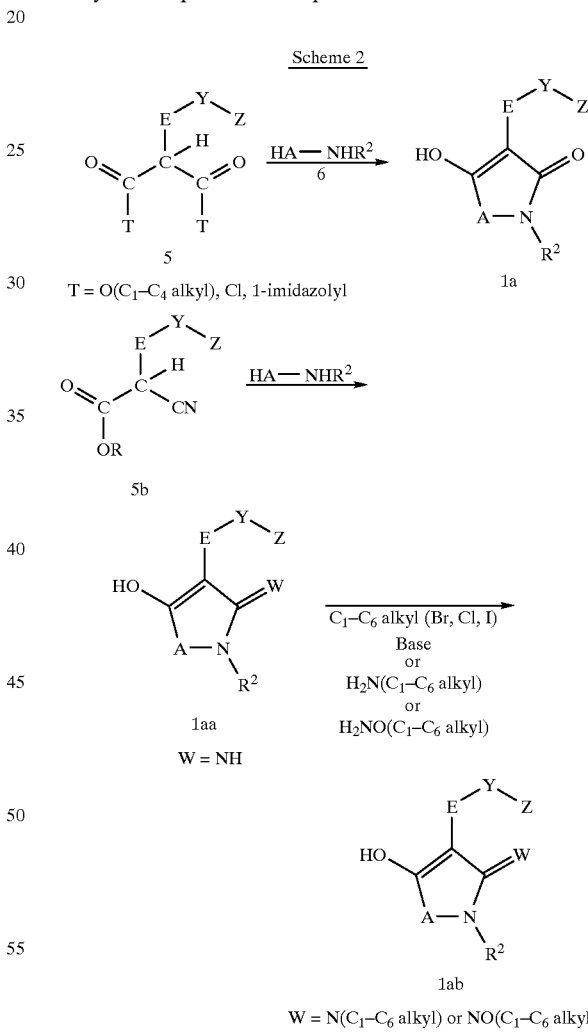

Esters of Formula 5a can be prepared from copper (I)-catalyzed reaction of malonate esters of Formula 7 with substituted aryl halides of Formula 8 according to methods adapted from A. Osuka, T. Kobayashi and H. Suzuki, *Synthesis*, (1983), 67 and M. S. Malamas, T. C. Hohman, and J. Millen, *J. Med. Chem.*, 1994, 37, 2043–2058, and illustrated in Scheme 3. Procedures to prepare compounds of Formula 8 are described below (see Scheme 32).

Malonate esters of Formula 5a can also be prepared from diester carboxylic acids of Formula 5c after modification of the carboxylic acid functional group to the appropriate Y and Z group. A copper (I)-catalyzed coupling of nialonates of Formula 7 with orthobromocarboxylic acids of Formula 8a (see A. Bruggink, A. McKillop, *Tetrahedron*, (1975), 31, 2607) can be used to prepare compounds of Formula 5c as shown in Scheme 3. Methods to prepare compounds of Formula 8a are common in the art (see P. Beak, V. Snieckus, *Acc. Chem. Res.*, (1982), 15, 306 and *Org. React.*, (1979), 26, 1 and references therein).

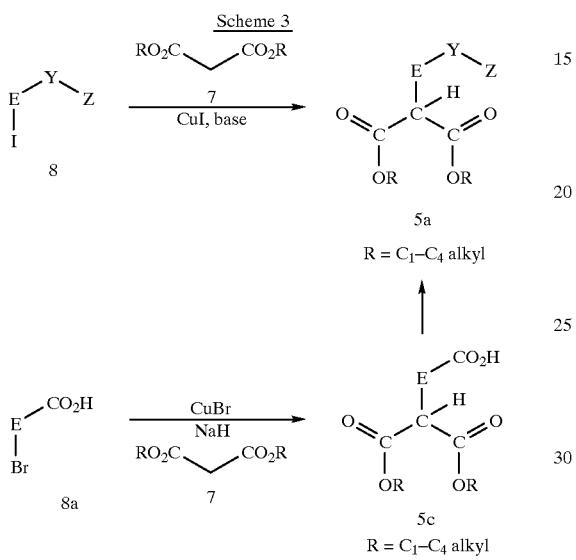

Additionally, the malonate esters of Formula 5a can be prepared by treating aryl acetic acid esters of Formula 9 with a dialkyl carbonate or alkyl chloroformate in the presence of a suitable base such as, but not limited to, sodium metal or sodium hydride (Scheme 4). For example, see *J. Am. Chem. Soc.*, (1928), 50, 2758. Nitrile esters of Formula 5b can be prepared similarly from compounds of Formula 10.

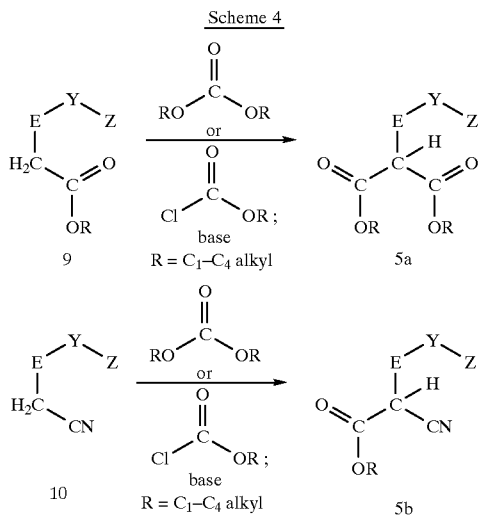

Esters of Formula 9 can be prepared from acid-catalyzed alcoholysis of aryl acetonitriles of Formula 10 or esterification of aryl acetic acids of Formula 11 as illustrated in Scheme 5 (see *Org. Synth.*, Coll. Vol. I, (1941), 270).

Additionally, esters of formula 9 can be prepared by palladium (0)-catalyzed cross coupling reaction of aryl iodides of Formula 8 with a Reformatsky reagent or an alkoxy(trialkylstannyl)acetylene followed by hydration (Scheme 5). For example, see T. Sakamnoto, A. Yasuhara, Y. Kondo, H. Yamanaka, *Synlett.*, (1992), 502, and J. F. Fauvarque, A. Jutard, *J. Organometal. Chem.*, (1977), 132, C17.

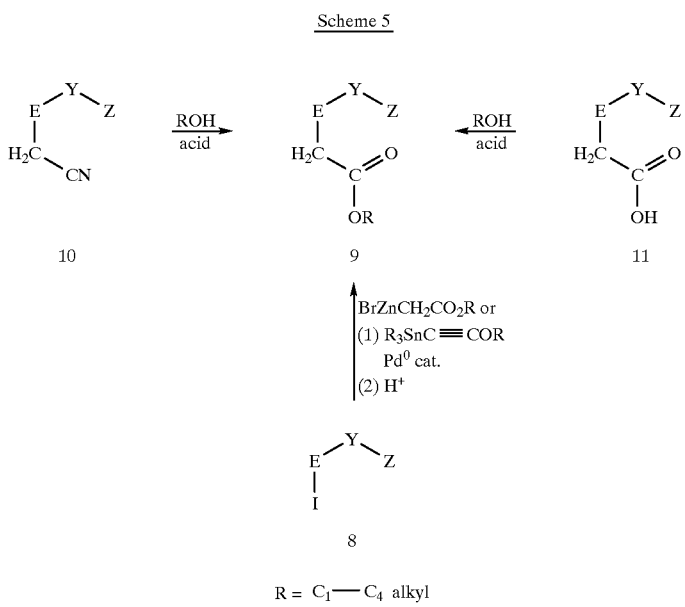

Aryl acetic acid esters of Formula 9a can also be prepared by copper (I)-catalyzed condensation of aryl halides of Formula 12 with compounds of Formula 13 as described in EP-A-307,103 and illustrated below in Scheme 6.

Scheme 6

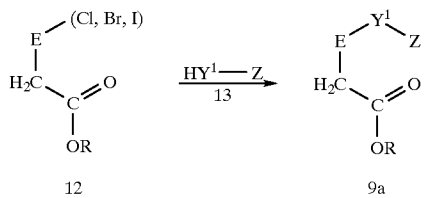

R = $C_1$—$C_4$ alkyl $Y^1$ = O, S, OCHR$^{15}$, SCHR$^{15}$ O—N=C(R$^7$), NR$^{15}$ Some esters of Formula 9 (Formula 9b) can also be prepared by forming the $Y^2$ bridge using conventional nucleophilic substitution chemistry (Scheme 7). Displacement of an appropriate leaving group (Lg) in electrophiles of Formula 15 or 16 with a nucleophilic ester of Formula 14 affords compounds of Formula 9b. A base, for example sodium hydride, is used to generate the corresponding alkoxide or thioalkoxide of the compound of Formula 14.

Scheme 7

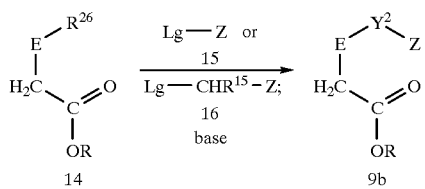

R = $C_1$-$C_6$ alkyl $R^{26}$ = OH, SH, CHR$^{15}$OH, CHR$^{15}$SH, NHR$^{15}$ $Y^2$ = O, S, OCHR$^{15}$, SCHR$^{15}$, CHR$^{15}$O, CHR$^{15}$S, NR$^{15}$ Lg = Br, Cl, I, OSO$_2$CH$_3$, OSO$_2$(4-Me-Ph)

Some esters of Formula 9 (Formula 9e) can also be prepared by forming the $Y^3$ bridge from substituted hydroxylamine 9d and carbonyl compounds 14a. The hydroxylamine 9d is in turn prepared from esters 9c. This method has been described in EP-A-600,835 and illustrated in Scheme 8.

Scheme 8

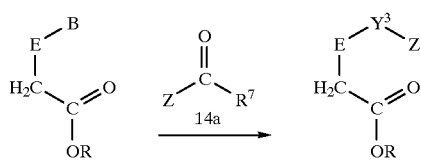

9c B = CHR$^{15}$Br          R = $C_1$-$C_6$ alkyl

9d B = CHR$^{15}$ONH$_2$•HCl    $Y^3$ = CHR$^{15}$ON=C(R$^7$)

2) Displacement and Conjugate Addition/Elimination Procedures

Compounds of Formula I can also be prepared by reaction of Formula 17 compounds with alkali metal alkoxides ($R^1O^-M^+$) or alkali metal thioalkoxides ($R^1S^-M^+$) in a suitable solvent (Scheme 9). The leaving group Lg$^1$ in the amides of Formula 17 are any group known in the art to undergo a displacement reaction of this type. Examples of suitable leaving groups include chlorine, bromine, and sulfonyl and sulfonate groups. Examples of suitable inert solvents are dimethylformamide or dimethyl sulfoxide.

Scheme 9

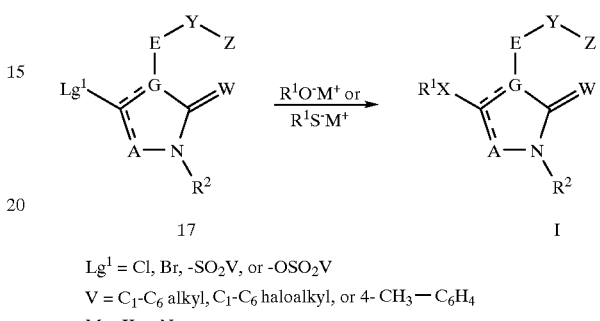

Lg$^1$ = Cl, Br, -SO$_2$V, or -OSO$_2$V

V = $C_1$-$C_6$ alkyl, $C_1$-$C_6$ haloalkyl, or 4- CH$_3$—C$_6$H$_4$

M = K or Na

Compounds of Formula 17a can be prepared from compounds of Formula 1b (compounds of Formula 1 wherein X is OH) by reaction with halogenating agents such as thionyl chloride or phosphorus oxybromide to form the corresponding β-halo-substituted derivatives (Scheme 10). Alternatively, compounds of Formula 1b can be treated with an alkylsulfonyl halide or haloalkylsulfonyl anhydride, such as methanesulfonyl chloride, p-toluenesulfonyl chloride, and trifluoromethanesulfonyl anhydride, to form the corresponding β-alkylsulfonate of Formula 17a. The reaction with the sulfonyl halides may be performed in the presence of a suitable base (e.g., triethylamine).

Scheme 10

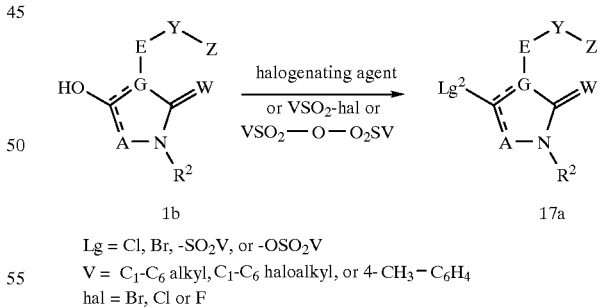

Lg = Cl, Br, -SO$_2$V, or -OSO$_2$V

V = $C_1$-$C_6$ alkyl, $C_1$-$C_6$ haloalkyl, or 4- CH$_3$—C$_6$H$_4$ hal = Br, Cl or F As illustrated in Scheme 11, sulfonyl compounds of Formula 17b can be prepared by oxidation of the corresponding thio compound of Formula 18 using well-known methods for the oxidation of sulfur (see Schrenk, K. In *The Chemistry of Sulphones and Sulphoxides*; Patai, S. et al., Eds.; Wiley: New York, 1988). Suitable oxidizing reagents include meta-chloro-peroxybenzoic acid, hydrogen peroxide and Oxone® (KHSO$_5$).

Scheme 11

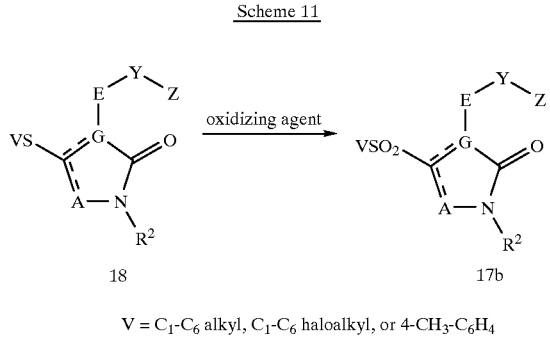

V = $C_1$-$C_6$ alkyl, $C_1$-$C_6$ haloalkyl, or 4-$CH_3$-$C_6H_4$

Alternatively, halo-compounds of Formula 17c (compounds of Formula 17a wherein A=N, G=N, and W=O) can be prepared from hydrazides of Formula 19 as illustrated in Scheme 12. When $R^{27}$=C(=S)S($C_1$–$C_4$ alkyl), the diacyl compound of Formula 19 is treated with excess thionyl halide, for example excess thionyl chloride. The product formed first is the ring-closed compound of Formula 20 which can be isolated or converted in situ to the compound of Formula 17c; see P. Molina, A. Tarraga, A. Espinosa, Synthesis, (1989), 923 for a description of this process.

Alternatively, when $R^{27}$=$R^2$ as defined above, the hydrazide of Formula 19 is cyclized with phosgene to form the cyclic urea of Formula 17c wherein hal=Cl. This procedure is described in detail in *J. Org. Chem.*, (1989), 54, 1048.

The hydrazides of Formula 19 can be prepared as illustrated in Scheme 13. Condensation of the isocyanate of Formula 21 with the hydrazine of Formula $H_2NNR^2R^{27}$ in an inert solvent such as tetrahydrofuran affords the hydrazide.

Scheme 13

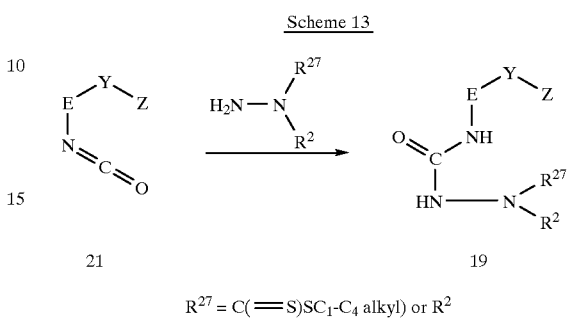

$R^{27}$ = C(=S)S$C_1$-$C_4$ alkyl) or $R^2$

3) Conjugate Addition/Cyclization Procedures

In addition to the methods disclosed above, compounds of Formula I wherein X=$SR^1$ and G=C (Formula Ic) can be prepared by treating a ketenedithioacetal of Formula 22 with an ambident nucleophile of Formula 6 (Scheme 14). The nucleophiles of Formula 6 are described above.

Scheme 12

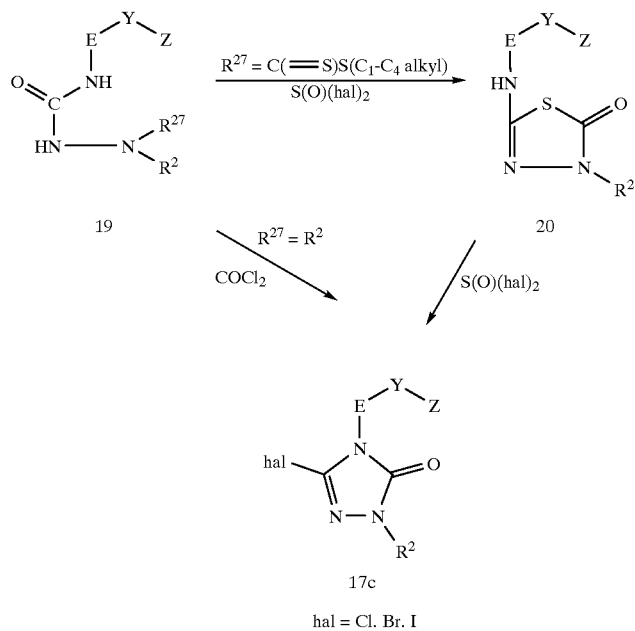

hal = Cl. Br. I

Scheme 14

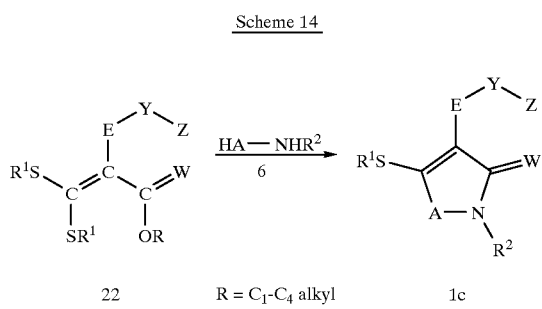

Ketene dithioacetals of Formula 22a or 22b can be prepared by condensing aryl acetic esters of Formula 9 or amides of Formula 9a, respectively, with carbon disulfide in the presence of a suitable base, followed by reaction with two equivalents of an $R^1$-halide, such as iodomethane or propargyl bromide (Scheme 15). Conversion of 22b to 22c can be accomplished by reaction with trialkyl tetrafluoroborates.

Scheme 15

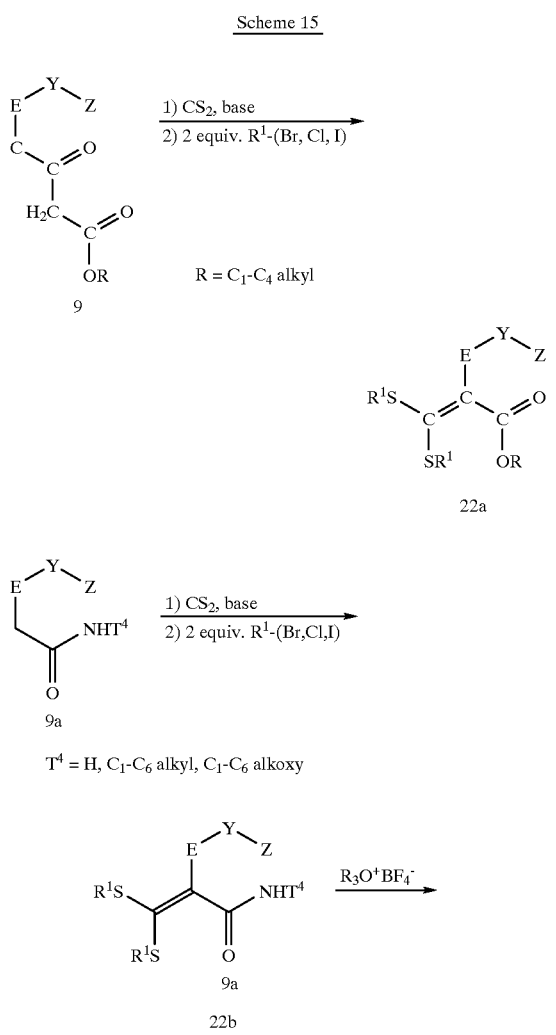

Compounds of Formula 1d (compounds of Formula 1 wherein A=N, G=N) can be prepared by condensation of N-amino-ureas of Formula 23 with a carbonylating agent of Formula 24 (Scheme 16). The carbonylating agents of Formula 24 are carbonyl or thiocarbonyl transfer reagents such as phosgene, thiophosgene, diphosgene (ClC(=O)OCCl$_3$), triphosgene (Cl$_3$COC(=O)OCCl$_3$), N,N'-carbonyldiimidazole, N,N'-thiocarbonyldiimidazole, and 1,1'-carbonyldi(1,2,4-triazole). Alternatively, the compounds of Formula 24 can be alkyl chloroformates or dialkyl carbonates. Some of these carbonylating reactions may require the addition of a base to effect reaction. Appropriate bases include alkali metal alkoxides such as potassium tert-butoxide, inorganic bases such as sodium hydride and potassium carbonate, tertiary amines such as triethylamine and triethylenediamine, pyridine, or 1,8-diazabicyclo[5.4.0]undec-7-ene (DBU). Suitable solvents include polar aprotic solvents such as acetonitrile, dimethylformamide, or dimethyl sulfoxide; ethers such as tetrahydrofuran, dimethoxyethane, or diethyl ether; ketones such as acetone or 2-butanone; hydrocarbons such as toluene or benzene; or halocarbons such as dichloromethane or chloroform. The reaction temperature can vary between 0° C. and 150° C. and the reaction time can be from 1 to 72 hours depending on the choice of base, solvent, temperature, and substrates.

Scheme 16

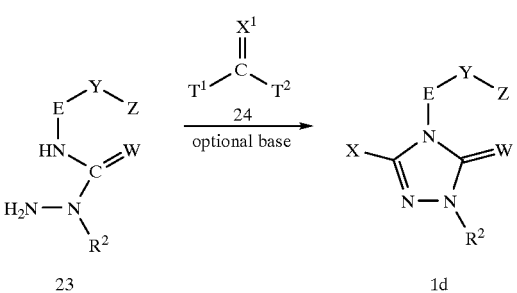

$T^1$ and $T^2$ are independently Cl, OCCl$_3$, O(C$_1$-C$_4$ alkyl), 1-imidazolyl, 1, 2, 4-triazolyl
X = OH or SH
$X^1$ = O or S N-Amino-ureas of Formula 23 can be prepared as illustrated in Scheme 17. Treatment of an arylamine of Formula 25 with phosgene, thiophosgene, N,N'-carbonyldiimidazole, or N,N'-thiocarbonyldimidazole produces the isocyanate or isothiocyanate of Formula 26. A base can be added for reactions with phosgene or thiophosgene. Isocyanates of Formula 26 can also be prepared by heating acylazides of Formula 25a in a solvent such as toluene or benzene (Curtius rearrangement). The corresponding acylazides can be prepared from well known methods in the art (see March, J., *Advanced Organic Chemistry*; 3rd Edition, John Wiley: New York, (1985), pp 428, 637 and also *Chem. Pharm. Bull* (1977), 25, 165, and references therein. Subsequent treatment of the iso(thio)cyanate with an $R^2$-substituted hydrazine produces the N-amino-urea of Formula 23.

Scheme 17

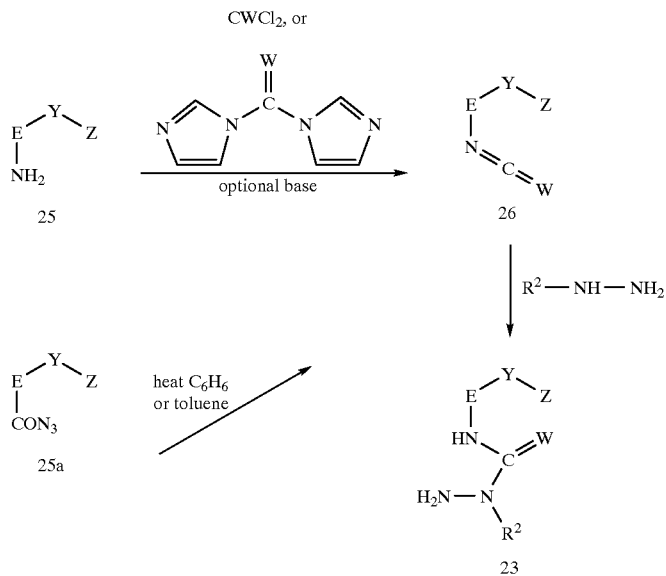

Compounds of Formula 1e (compounds of Formula 1 wherein $A=CR^5$, $G=N$. and $X=O$) can be prepared by either method illustrated in Scheme 18. Ureas of Formula 27 are reacted with activated 2-halocarboxylic acid derivatives such as 2-halocarboxylic acid chlorides, 2-halocarboxylic acid esters or 2-haloacyl imidazoles. The initial acylation on the arylamino nitrogen is followed by an intramolecular displacement of the 2-halo group to effect cyclization. Base may be added to accelerate the acylation and/or the subsequent cyclization. Suitable bases include triethylamine and sodium hydride. Alternatively, Formula 1e compounds can be prepared by reaction of Formula 26 iso(thio)cyanates or Formula 26a carbodiimides with Formula 28a esters. As described above, base may be added to accelerate the reaction and subsequent cyclization to Formula 1e compounds. Carbodiimides 26a can be prepared as shown in Scheme 18, starting with compounds of Formula 26.

Scheme 18

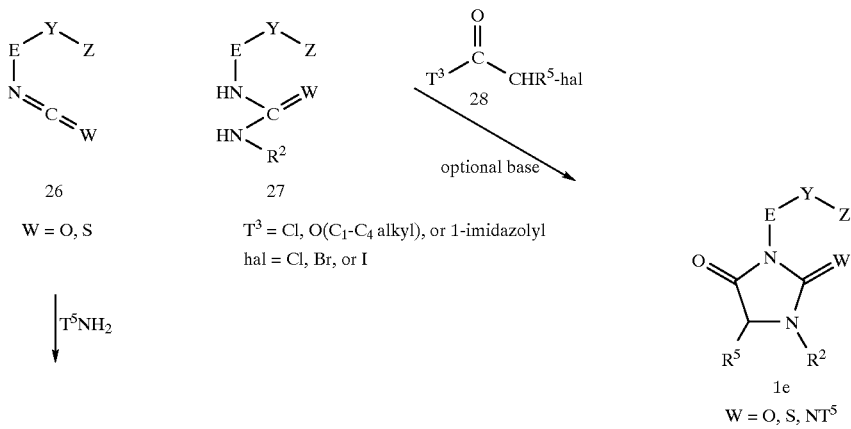

-continued

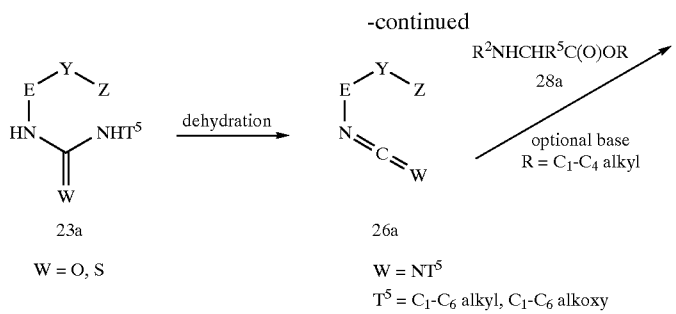

23a
W = O, S

26a
W = NT⁵
T⁵ = $C_1$-$C_6$ alkyl, $C_1$-$C_6$ alkoxy

The (thio)ureas or amidines of Formula 27 can be prepared by either of the methods illustrated in Scheme 19. The arylamine of Formula 25 can be contacted with an isocyanate or isothiocyanate of Formula $R^2N=C=W$ as described above. Alternatively, an iso(thio)cyanate of Formula 26 or carbodiimide of Formula 26a can be condensed with an amine of Formula $R^2$—$NH_2$ to form the urea or amidine. The arylamine and iso(thio)cyanates of Formulae 25 and 26, respectively, are commercially available or prepared by well-known methods. For example, isothiocyanates can be prepared by methods described in *J. Heterocycl Chem.*, (1990), 27, 407. Isocyanates can be prepared as described in March, J., *Advanced Organic Chemistry*; 3rd ed., John Wiley: New York, (1985), pp 944, 1166 and also in *Synthetic Communications*, (1993), 23 (3), 335 and references therein. For methods describing the preparation of arylamines of Formula 25 that are not commercially available, see M. S. Gibson, *In The Chemistry of the Amino Group*; Patai, S., Ed.; Interscience Publishers, 1968; p 37 and *Tetrahedron Lett.* (1982), 23 (7), 699 and references therein.

Scheme 19

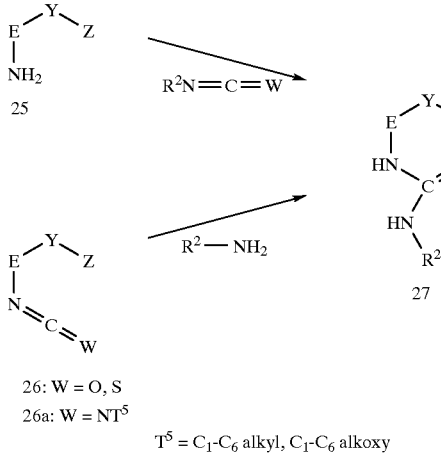

26: W = O, S
26a: W = NT⁵

T⁵ = $C_1$-$C_6$ alkyl, $C_1$-$C_6$ alkoxy

4) Thionation Procedures

Compounds of Formula Ie, compounds of Formula I wherein W=S, can be prepared by treating compounds of Formula Id (I wherein W=O) with thionating reagents such as $P_2S_5$ or Lawesson's reagent (2,4-bis(4-methoxyphenyl)-1,3-dithia-2,4-diphosphetane-2,4-disulfide) as illustrated in Scheme 20 (see *Bull. Soc. Chim. Belg.*, (1978), 87, 229; and *Tetrahedron Lett.*, (1983), 24, 3815).

Scheme 20

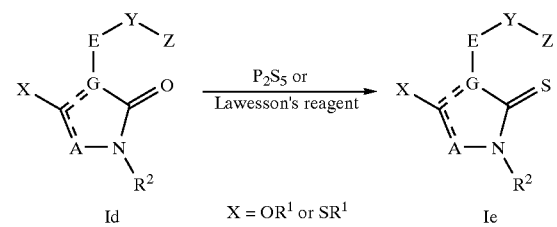

Id     X = $OR^1$ or $SR^1$     Ie

Reaction of compounds of Formula Iea with an alkyl halide in the presence of base provides compounds of Formula Ieb, which can be reacted with compounds of Formula $T^5NH_2$ and then alkylated with $R^2$—(Br, Cl, or I) to provide compounds of Formula Iec.

Scheme 20a

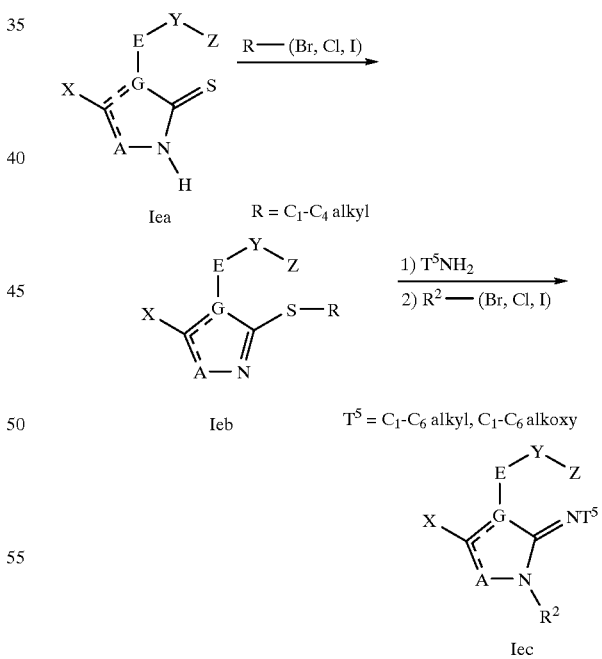

5) Aryl Moiety (E-Y-Z) Synthesis Procedures

Compounds of Formula If (compounds of Formula I wherein Y is $CHR^{15}O$, $CHR^{15}S$, or $CHR^{15}O$—$N=CR^7$) can be prepared by contacting halides of Formula 29 with various nucleophiles (Scheme 21). The appropriate alcohol or thiol is treated with a base, for example sodium hydride, to form the corresponding alkoxide or thioalkoxide which acts as the nucleophile.

Scheme 21

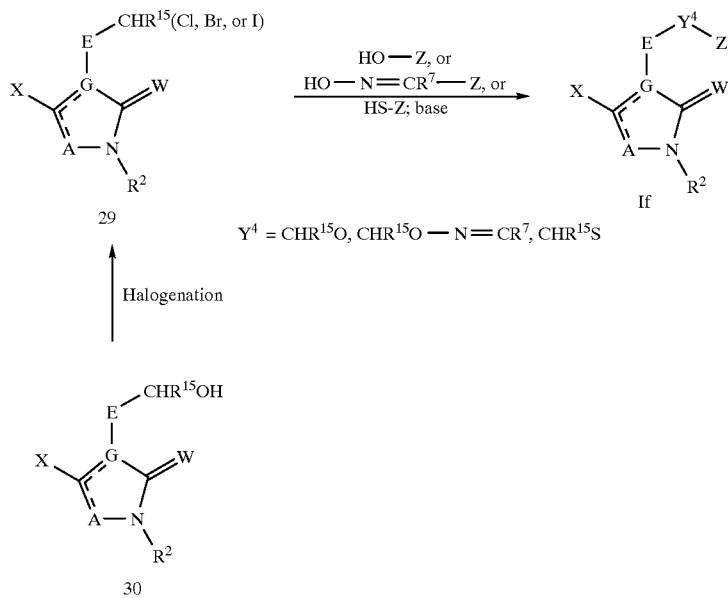

Some aryl halides of Formula 29 can be prepared by radical halogenation of the corresponding alkyl compound (i.e., H instead of halogen in Formula 29), or by acidic cleavage of the corresponding methyl ether (i.e., OMe instead of halogen in Formula 29). Other aryl halides of Formula 29 can be prepared from the appropriate alcohols of Formula 30 by well known halogenation methods in the art (see Carey, F. A.; Sundberg, R J *Advanced Organic Chemistry*; 3rd ed., Part B, Plenum: New York, (1990), p 122).

Compounds of Formula I wherein Y is $CR^6\!=\!R^6$ or $CHR^6\!-\!CHR^6$ (Formula Ig and Ih, respectively) can be prepared as illustrated in Scheme 22. Treatment of the halides of Formula 29 with triphenylphosphine or a triallylphosphite produces the corresponding phosphonium salt (Formula 31) or phosphonate (Formula 32), respectively. Condensation of the phosphorus compound with a base and a carbonyl compound of Formula $Z(R^6)C\!=\!O$ affords the olefin of Formula Ig.

Scheme 22

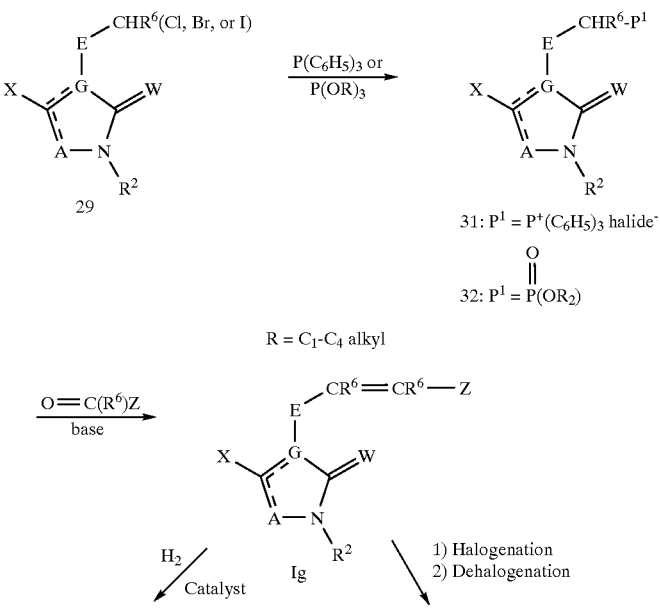

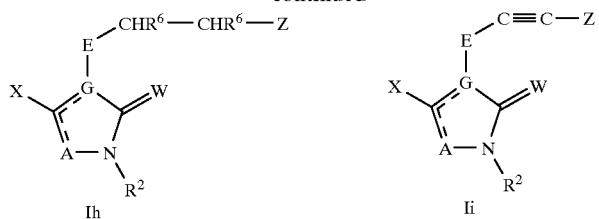

The olefins of Formula Ig can be converted to the saturated compounds of Formula Ih by hydrogenation over a metal catalyst such as palladium on carbon as is well-known in the art (Rylander, *Catalytic Hydrogenation in Organic Synthesis*; Academic: New York, 1979).

Formula Ii alkynes can be prepared by halogenation/dehalogenation of Formula Ig olefins using procedures well-known in the art (March, J. *Advanced Organic Chemistry*; 3rd ed., John Wiley: New York, (1985), p 924). Additionally, Formula Ii alkynes can be prepared by well-known reaction of aryl halides with alkyne derivatives in the presence of catalysts such as nickel or palladium (see *J. Organomet. Chem.*, (1975), 93 253–257).

The olefin of Formula Ig can also be prepared by reversing the reactivity of the reactants in the Wittig or Horner-Emmons condensation. For example, 2-alkylaryl derivatives of Formula 33 can be converted into the corresponding dibromo-compound of Formula 34 as illustrated in Scheme 23 (see *Synthesis*, (1988), 330). The dibromo-compound can be hydrolyzed to the carbonyl compound of Formula 35, which in turn can be condensed with a phosphorus-containing nucleophile of Formula 36 or 37 to afford the olefin of Formula Ig. Carbonyl compounds of Formula 35 can also be prepared by oxidation of halides of Formula 29 in Scheme 22 (see *Tetrahedron Lett.*, (1990), 31, 4825 and *Bull. Chem. Soc. Jpn.*, (1981), 54, 2221 and references therein). Additionally, compounds of Formula 35 can be prepared by oxidation of the corresponding alcohols of Formula 30.

Vinylhalides of Formula Ij can be prepared by reacting phosphorus reagents of Formulae 37a or 37b with carbonyl compounds of Formula 35 (Scheme 23). The preparations of halides of Formula 37a from the appropriate diethylphosphonoacetate are described by McKenna and Khawli in *J. Org. Chem.*, (1986), 51, 5467. The thiono esters of Formula 37b can be prepared from esters of Formula 37a by converting the carbonyl oxygen of the ester to a thiocarbonyl (see *Chem. Rev.*, (1984), 84, 17 and *Tetrahedron Lett.*, (1984), 25, 2639).

Scheme 23

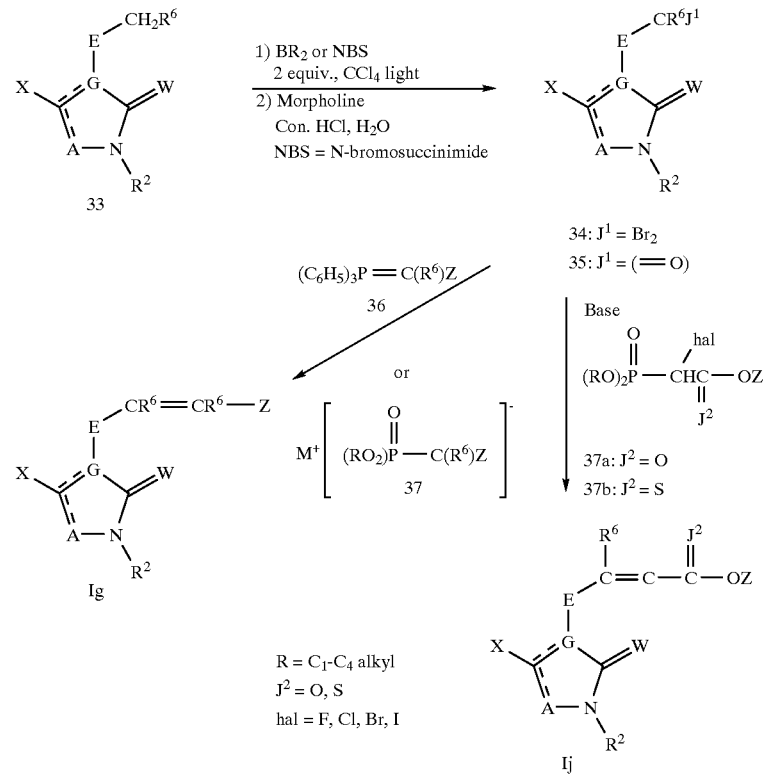

Oximes of Formula Ik (Formula I wherein Y is C(R⁷)=N—O) can be prepared from carbonyl compounds of Formula 38 by condensation with hydroxylamine, followed by O-alkylation with electrophiles of Formula Z—(Cl, Br, or I) (Scheme 24). Alternatively, the O-substituted hydroxylamine can be condensed with the carbonyl compound of Formula 38 to yield oximes of Formula Ik directly.

Scheme 24

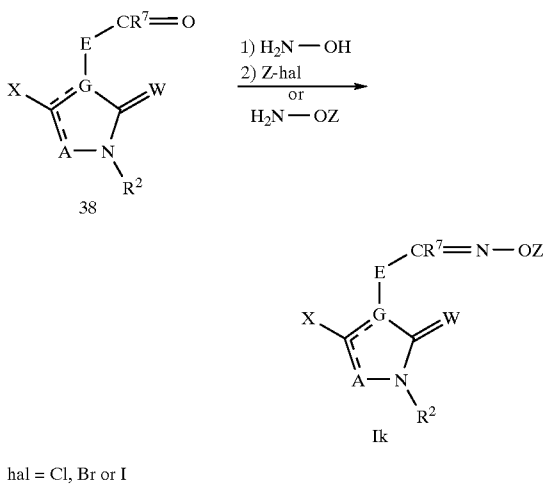

hal = Cl, Br or I

Carbamates of Formula II can be prepared by reacting aryl alcohols of Formula 30 with isocyanates of Formula 39 (Scheme 25). A base such as triethylamine can be added to catalyze the reaction. As shown, carbamates of Formula II can be further alkylated to provide the carbamates of Formula Im.

Scheme 25

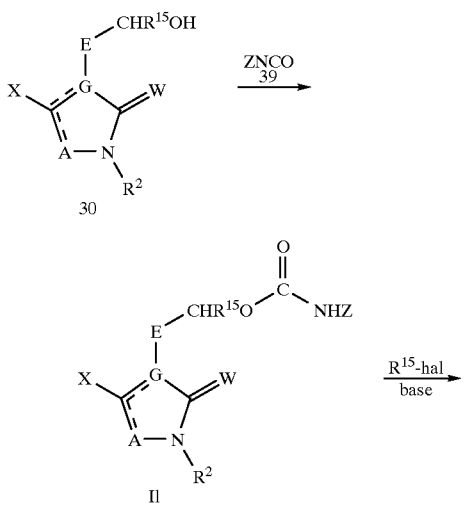

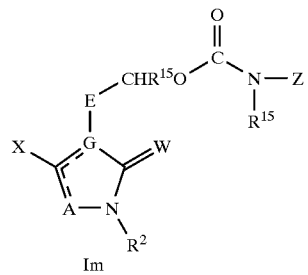

hal = Cl, Br or I

Compounds of Formula I wherein Y is —CHR¹⁵O—N=C(R⁷)—C(=N—A²—Z¹)—A¹—, —CHR¹⁵O—N=C(R⁷)—C(R⁷)=N—A²—A³— or —CHR15O—N=C(—C(R⁷)=N—A²—Z¹)— can be prepared by methods known in the art or obvious modifications (see, for example, WO 95/18789, WO 95/21153, and references therein) together with the methods disclosed herein.

Compounds of Formula I wherein Y is —CHR¹⁵OC(=O)O—, —CHR¹⁵OC(=S)O—, —CHR¹⁵OC(=O)S—, —CHR¹⁵OC(=S)S—, —CHR¹⁵SC(=O)N(R¹⁵)—, —CHR¹⁵SC(=S)N(R¹⁵)—, —CHR¹⁵SC(=O)O—, —CHR¹⁵SC(=S)O—, —CHR¹⁵SC(=O)S—, —CHR¹⁵SC(=S)S—, —CHR¹⁵SC(=NR¹⁵)S— or —CHR¹⁵N(R¹⁵)C(=O)N(R¹⁵)— can be prepared by methods known in the art or obvious modifications (see, for example, U.S. Pat. No. 5,416,110-A, EP 656351-A1 and references therein) together with the methods disclosed herein.

The compounds of the present invention are prepared by combinations of reactions as illustrated in the Schemes 1–25 in which Z is a moiety as described in the sumnmay. Preparation of the compounds containing the radical Z as described in the summnary, substituted with L (defined as any group attached to Z as depicted in each of the individual schemes) can be accomplished by one skilled in the art by the appropriate combination of reagents and reaction sequences for a particular Z-L. Such reaction sequences can be developed based on known reactions available in the chemical art. For a general reference, see March, J. *Advanced Organic Chemistry*; 3rd ed., John Wiley: New York, (1985) and references therein. See the following paragraphs for some examples of how L is defined in individual schemes, and the preparation of representative Z-L examples.

Compounds of Formula 41 in Scheme 26 can be prepared from compounds of Formula 40 by reaction with hydroxylamnine or hydroxylamine salts. See Sandler and Karo, "Organic Functional Group Preparations," Vol. 3 Academic Press, New York, (1972) 372–381 for a review of methods. Compounds of Formula 41 correspond to compounds of Formula 13 in Scheme 6 when Y¹=O—N=C(R⁷) and in Scheme 21, reagent HO—N=CR⁷.

Scheme 26

Compounds of Formula 40 can be prepared from compounds of Formula 39a (Scheme 27) by Friedel-Crafts acylation with compounds of Formula 42. (See Olah, G. "Friedel-Crafts and Related Reactions," Interscience, New York (1963–1964) for a general review). Compounds of Formula 40 may also be prepared by reaction of acyl halides, anhydrides, esters, or amides of Formula 45 with organometallic reagents of Formula 44. (See March, *J. Advanced Organic Chemistry*; 3rd ed., John Wiley: New York, (1985), pp 433–435 and references therein.) The organometallic compounds of Formula 44 may be prepared by reductive metallation or halogen-metal exchange of a halogen-containing compound of Formula 43 using, for example, magnesium or an organolithium reagent, or by deprotonation of compounds of Formula 39a using a strong base such as a lithioamide or an organolithium reagent, followed by transmetallation. Compound 40 corresponds to Compound 14a in Scheme 8, while compound 40a corresponds to O=C($R^6$)Z in Scheme 22.

Scheme 27

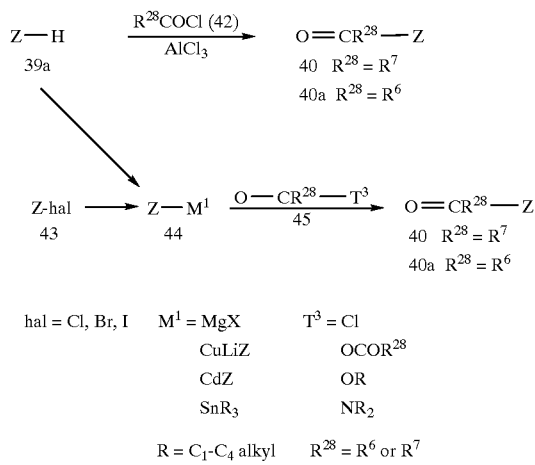

Compounds of Formula 43 may be prepared by reaction of compounds of Formula 39a (Scheme 28) with, for example, bromine or chlorine, with or without additional catalysts, under free-radical or aromatic electrophilic halogenation conditions, depending on the nature of Z. Alternative sources of halogen, such as N-halosuccinimides, tert-butyl hypohalites or $SO_2Cl_2$, may also be used. (See March, J. *Advanced Organic Chemistry*; 3rd ed., John Wiley: New York, (1985), pp 476–479, 620–626, and references therein.) For a review of free-radical halogenation, see Huyser, in Patai,"The Chemistry of the Carbon-Halogen Bond," Part 1, Wiley, New York (1973) pp 549–607. For electrophilic substitutions, see de la Mare, "Electrophilic Halogenation," Cambridge University Press, London (1976). Compounds of Formula 43 correspond to compounds of Formula 15 in Scheme 7 where Lg=Br, Cl, or I and reagent Z-hal in Scheme 24. Compounds of Formula 47 can be prepared from compounds of Formula 46 by similar procedures. Compounds of Formula 47 correspond to compounds of Formula 16 in Scheme 7 where Lg=Br, Cl, or I. Compounds of Formula 36 or 37 in Scheme 23 can be prepared by reaction of compounds of Formula 47 with triphenylphosphine or trialkyl phosphites, respectively, followed by deprotonation with base. See Cadogen, "Organophosphorus Reagents in Organic Synthesis," Academic Press, New York (1979) for a general treatise on these reagents.

Scheme 28

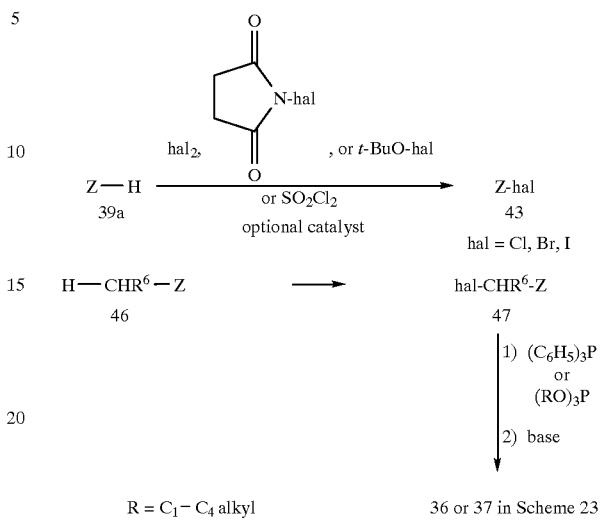

Compounds of Formula 48 can be prepared from compounds of Formula 40b by treatment with peracids such as perbenzoic or peracetic acid, or with other peroxy compounds in the presence of an acid catalysts, followed by hydrolysis of the resultant ester. For a review, see Plesnicar, in Trahanovsky, "Oxidation in Organic Chemistry," pt. C, Academic Press, New York (1978) pp 254–267. Formula 48 corresponds to Formula 13 in Scheme 6 when $Y^1$=O and reagent HO-Z in Scheme 21. Compounds of Formula 52 can be prepared from compounds of Formula 48 by conversion to the dialkylthiocarbamates of Formula 50 followed by rearrangement to Formula 51 and subsequent hydrolysis. See M. S. Newman and H. A. Karnes, *J. Org. Chem.* (1966), 31, 3980–4. Formula 52 corresponds to Formula 13 in Scheme 6 when $Y^1$=S and reagent HS-Z in Scheme 21.

Scheme 29

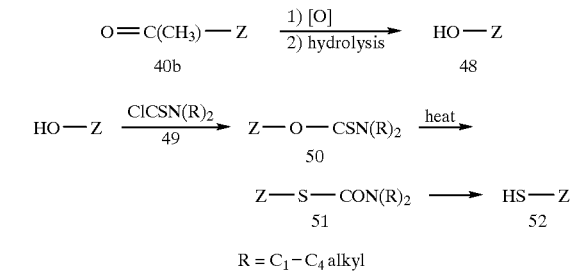

Compounds of Formula 53 can be converted to compounds of Formulae 43, 48 or 52 via the diazonium compounds 54, by treatment with nitrous acid followed by subsequent reaction (Scheme 30). See reviews by Hegarty, pt. 2, pp 511–91 and Schank, pt. 2, pp 645–657, in Patai, "The Chemistry of Diazonium and Diazo Groups," Wiley, New York (1978). Treatment of Formula 54 compounds with cuprous halides or iodide ions yield compounds of Formula 43. Treatment of Formula 54 compounds with cuprous oxide in the presence of excess cupric nitrate provides compounds of Formula 48. (Cohen, Dietz, and Miser, *J. Org. Chem*, (1977), 42, 2053). Treatment of Formula 54 compounds with $(S_2)^{-2}$ yields compounds of Formula 52.

Scheme 30

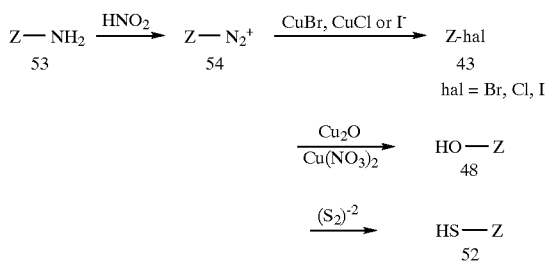

Scheme 31

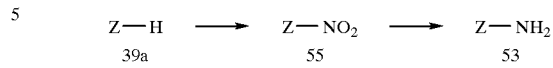

Compounds of Formula 53 can be prepared from compounds of Formula 39a by nitration, followed by reduction (Scheme 31). A wide variety of nitrating agents is available (see Schofield, "Aromatic Nitration," Cambridge University Press, Cambridge (1980)). Reduction of nitro compounds can be accomplished in a number of ways (see March, J. *Advanced Organic Chemistry*; 3rd ed., John Wiley: New York, (1985), pp 1103–4 and references therein). Formula 53 corresponds to Formula 13 in Scheme 6 when $Y^1=NR^{15}$ and $R^{15}=H$.

Iodides of Formula 8 can be prepared from compounds of Formula 58 by the methods described above in Schemes 21–25 for various Y-Z combinations. Compounds of Formula 58 can in turn be prepared from compounds of Formula 57 by functional group interconversions which are well known to one skilled in the art. The compounds of Formula 57 can be prepared by treating compounds of Formula 56 with an organolithium reagent such as n-BuLi or LDA followed by trapping the intermediate with iodine (Beak, P., Snieckus, V. *Acc. Chem. Res.*, (1982), 15,306). Additionally, lithiation via halogen metal exchange of compounds of Formula 56, where H is replaced by Br, will produce an intermediate which can be trapped with iodine to prepare compounds of Formula 57 (Parham, W E, Bradsher, C. K. *Acc. Chem. Res.*, (1982), 15, 300 (Scheme 32).

Scheme 32

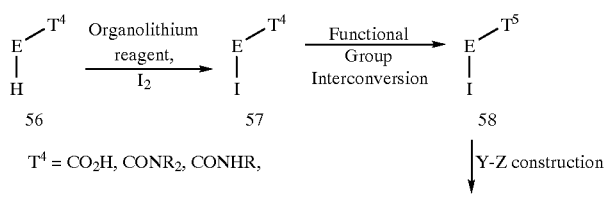

$T^4$ = $CO_2H$, $CONR_2$, CONHR,

CSNHR, 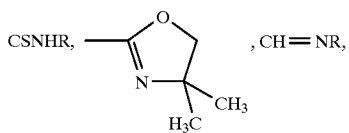, CH=NR, 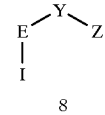

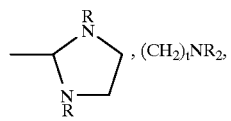, $(CH_2)_tNR_2$, $CH_2OH$, OMe, $OCH_2OMe$ $T^5$ = $CHR^6$(Cl, Br, I), CHO
$CH_2OH$, OH R = $C_1$–$C_4$ alkyl
t = 1 or 2

Conversion of compounds of Formula In to compounds of Formula Io is summarized in Scheme 33. Reaction of the secondary amides with silylating agents, such as trimethylsilyl chloride in the presence of base or hexamethyldisilazane in the presence of acid, provides the silylated intermediate which is oxidized in situ with the peroxo-molybdenum compound $MoO_5 \cdot HMPA$ complexed with pyridine or dimethylformamide. Subsequent hydrolysis with aqueous EDTA (ethylenediaminetetraacetic acid) liberates the hydroxylated armides (see S. A. Martin, P. G. Sammes and R. M. Upton, *J. Chem. Soc., Perkin Trans* 1, (1979), 2481 and J. H. Rigby and M. Qabar, *J. Org. Chem.* (1989), 54, 5852). Optional alkylation with $C_1$–$C_2$ alkyl halides in the presence of base or acylation with acetic anhydride can be performed on the hydroxyl amides of Formula Io where $R^{2'}$=OH.

Scheme 33

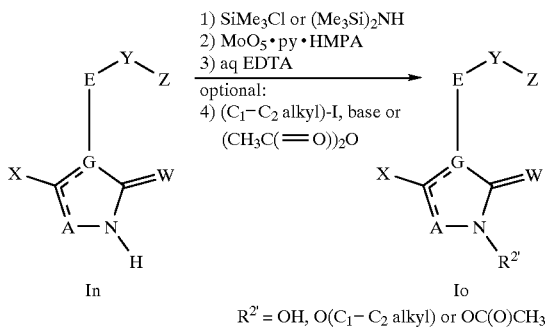

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane; s=singlet, d=doublet, t=triplet, m=multiplet, dd=doublet of doublets, br s=broad singlet.

EXAMPLE 1

Step A: Preparation of methyl 3-isocyanato-2-thiophenecarboxylate

Diphosgene (4.6 mL) was added dropwise to a solution of methyl 3-amino-2-thiophenecarboxylate (5.0 g) in p-dioxane (100 mL) at room temperature under $N_2$. Triethylamine (5.3 mL) was then added with concomitant formation of a white precipitate. The resulting reaction mixture was heated at reflux overnight. The reaction was allowed to cool to room temperature and then filtered to remove solid impurities. The precipitate was rinsed with diethyl ether (about 250 mL) and the filtrate was concentrated under reduced pressure to yield 6.4 g of crude title compound of Step A as a brown solid. $^1H$ NMR ($CDCl_3$): δ 7.43 (d,1H), 6.78 (d,1H), 3.92 (s,3H).

Step B: Preparation of methyl 3-[[(2,2-dimethylhydrazino)carbonyl]amino]-2-thiopnecarboxylate The tide compound of Step A (6.4 g) was dissolved in toluene (35 mL) under $N_2$ and the solution was cooled to about 5° C. (ice bath) followed by the subsequent addition of 1,1-dimethylhydrazine (2.7 mL). A beige precipitate formed immediately and the mixture was allowed to stir for 30 min. The solid was filtered off, rinsed with hexane and then dried under vacuum to afford 6.9 g (81%) of the title compound of Step B. $^1H$ NMR ($CDCl_3$): δ 10.66 (br s,1H), 8.05 (d,1H), 7.43 (d,1H), 5.49 (br s,1H), 3.89 (s,3H), 2.65 (s,6H).

Step C: Preparation of methyl 3-(3-chloro-4,5-dihydro-1-methyl-5-oxo-1H-1,2,4-triazol-4-yl)-2-thiophenecarboxylate Triphosgene (16.8 g) was added to a solution of the title compound of Step B (6.9 g) in methylene chloride (250 mL) under $N_2$. The reaction mixture was heated at reflux overnight, cooled, and then concentrated under reduced pressure. The resulting brown oil was dissolved in methylene chloride and washed with water. The aqueous layer was further extracted three times with methylene chloride and the combined organic extracts were dried ($MgSO_4$), filtered and concentrated in vacuo to yield 7.92 g of the title compound of Step C. $^1H$ NMR ($CDCl_3$): δ 7.66 (d,1H), 7.13 (d,1H), 3.85 (s,3H), 3.52 (s,3H).

Step D: Preparation of methyl 3-(4,5-dihydro-3-methoxy-1-methyl-5-oxo-1H-1,2,4-triazol-4-yl)-2-thiophenecarboxylate Sodium methoxide (16.5 mL of a 30% solution in methanol) was added to a solution of the title compound of Step C (7.9 g) in anhydrous dimethoxyethane/methanol (85 mL/35 mL). The resulting yellow solution was heated to 50° C. for 2 h under $N_2$ and then left to stir overnight at room temperature. The reaction mixture was concentrated under reduced pressure and the residue was dissolved in methylene chloride. The resulting mixture was washed with water and then with saturated aqueous NaCl. The aqueous layer was filtered through Celite® and the filtrate was extracted three times with methylene chloride. The combined methylene chloride layers were dried ($MgSO_4$), filtered, and concentrated under reduced pressure to give 5.4 g of an off-white solid. The crude product was purified by flash chromatography (20–100% ethyl acetate/hexane as eluent) to afford 3.9 g of the title compound of Step D as a white solid. $^1H$ NMR ($CDCl_3$): δ 7.58 (d,1H), 7.12 (d,1H), 3.93 (s,3H), 3.83 (s,3H), 3.44(s,3H).

Step E: Preparation of 2,4-dihydro-4-[2-(hydroxymethyl)-3-thienyl]-5-methoxy-2-methyl-3H-1,2,4-triazol-3-one To a solution of the title compound of Step D (1.8 g) in methylene chloride (23 mL) under $N_2$ at −78° C. was added a solution of diisobutylaluminum hydride (18.3 mL, 1 M) in methylene chloride. The resulting solution was allowed to stir at −78° C. for 15 min, warmed to room temperature and then stirred for 1.5 h. After cooling the reaction mixture to −78° C., acetone was added and after about 10 min, the reaction mixture was quenched with 1N HCl. The reaction mixture was allowed to warm to room temperature, was diluted further with methylene chloride, and was then washed with water. The organic layer was dried (MgSO$_4$), filtered and concentrated in vacuo to yield 1.3 g of the title compound of Step E as an off-white solid.

Step F: Preparation of 4-[2-(bromomethyl)-3-thienyl]-2,4-dihydro-5-methoxy-2-methyl-3H-1,2,4-triazol-3-one To a suspension of the title compound of Step E (2.6 g) in methylene chloride (20 mL) under N$_2$ at room temperature was added sequentially triphenylphosphine (3.44 g) and carbon tetrabromide (5.58 g). The resulting orange solution was allowed to stir for 1 h at room temperature and was then concentrated under reduced pressure to give an orange oil. The residue was purified by flash chromatography (1:1 ethyl acetate:hexane as eluent) to afford 2.3 g of the title compound of Step F, a compound of the invention, as a white solid. $^1$H NMR (CDCl$_3$): δ 7.34 (d,1H), 6.92 (d,1H), 4.65 (s,2H), 3.98 (s,3H), 3.45 (s,3H).

EXAMPLE 2

Step A: Preparation of 2-(3-bromophenyl)-2-methyl-1,3-dioxolane 1-(3-bromophenyl)ethanone (60.6 g), ethylene glycol (83.7 mL), and p-toluenesulfonic acid (0.15 g) were dissolved in benzene (250 mL) and heated at reflux overnight in a Dean-Stark apparatus. The mixture was cooled and washed with water. The aqueous layer was further extracted twice with chlorobutane and the combined organic layers were dried (MgSO$_4$), filtered and the solvent was removed under reduced pressure to yield 75.0 g of a yellow oil. The oil was purified by distillation under reduced pressure (19–24 Pa, 64–74° C.) to afford 70.1 g of the title compound of Step A as an oil. $^1$H NMR (CDCl$_3$): δ 7.64 (s,1H), 7.40 (m,2H), 7.20 (m,1H), 4.0 (m,2H), 3.7 (m,2H), 1.63 (s,3H).

Step B: Preparation of 2-[3-(trimethylsilyl)phenyl]-2-methyl-1,3-dioxolane

A three-neck flask was charged with magnesium pieces (2.0 g) and tetrahydrofuiran (12 mL) under a nitrogen atmosphere. A small quantity of iodine was added and the mixture turned yellow. To this yellow mixture was added dropwise a solution of the title compound of Step A (20.0 g) in 30 mL of THF. The reaction mixture was warmed to 65° C. during the addition and then was heated at reflux for 1.5 h after the addition was complete. After cooling the reaction to 60° C., a solution of trimethylsilyl chloride (10.4 mL) in THF (12 mL) was added and the mixture was heated at reflux for two hours and then was allowed to stir overnight at room temperature. The reaction mixture was poured into saturated aqueous NH$_4$Cl and the aqueous layer was extracted twice with diethyl ether and then once with ethyl acetate. The combined organic layers were dried over MgSO$_4$, filtered and the was solvent removed to give an oil (20.0 g) which crystallized upon standing. This solid was then recrystallized from pentane to afford 11.2 g of the title compound of Step B as a white solid melting at 54–55° C. $^1$H NMR (CDCl$_3$): δ 7.63 (s,1H), 7.44 (m,2H), 7.33 (t,1H), 4.0 (m,2H), 3.78 (m,2H), 1.67 (s,3H), 0.27 (s,8H).

Step C: Preparation of 1-[3-(trimethylsilyl)phenyl]ethanone

To a solution of the title compound of Step B (11.2 g) in acetone (400 mnL) was added an aqueous solution of 1N hydrochloric acid (6 mL) and the mixture was heated at reflux overnight. After cooling, the mixture was concentrated under reduced pressure and the resulting residue was dissolved in diethyl ether and dried (MgSO$_4$). The drying agent was removed by filtration and the solvent was removed under reduced pressure to give a yellow oil. The crude product was combined with another batch of crude product prepared in the same manner and purified by distillation (47 Pa, 58–59° C.) to afford 8.9 g of the title compound of Step C as an oil. $^1$H NMR (CDCl$_3$): δ 8.11 (s,1H), 7.92 (d,1H), 7.7 (d,1H), 7.47 (t,1H), 2.62 (s,3H), 0.30 (s,8H).

Step D: Preparation of 1-[3-(trimethylsilyl)phenyl]ethanone oxime

To a solution of the title compound of Step C (8.9 g) in methanol (120 mL)/water (50 mL) was added sodium acetate (7.5 g) followed by the addition of hydroxylamine hydrochloride (3.8 g). The mixture was heated at reflux overnight, cooled to room temperature, and concentrated to an oil. The oil was mixed with water and extracted three times with methylene chloride. The combined organic phases were dried (MgSO$_4$), concentrated, and chromatographed on silica gel with 8% ethyl acetate/hexane to afford the title compound of Step D as an oil. $^1$H NMR (CDCl$_3$): δ 8.8 (br s,1H), 7.77 (s,1H), 7.5 (m,2H), 7.37 (t,1H), 2.31 (s,3H), 0.27 (s,8H).

Step E: Preparation of 2,4-dihydro-5-methoxy-2-methyl-4-[2-[[[[1-[3-(trimethylsilyl)phenyl]ethylidene]amino]oxy]methyl]-3-thienyl]-3H-1,2,4-triazol-3-one A solution of the title compound of Step D (1.6 g) in DMF (18 mL) was cooled to 0° C. (ice bath) under N$_2$. Sodium hydride (236 mg) was added and, after 20 min, a solution of the title compound of Step F in Example 1 (2.3 g) in DMF (18 mL) was added. The reaction mixture was kept at 0° C. for 1 h and then at room temperature for another hour before quenching with water. The mixture was extracted four times with ethyl acetate and the combined organic extracts were washed with saturated aqueous NaCl, dried (MgSO$_4$), filtered and concentrated under reduced pressure to a gold oil. The crude product was purified by flash chromatography (1:1 ethyl acetate:hexane as eluent) to afford 2.7 g of the title compound of Step E, a compound of the invention, as a very viscous oil/solid. $^1$H NMR (CDCl$_3$): δ 7.76 (s,1H), 7.60 (m,1H), 7.54 (m,1H), 7.36 (d,1H), 7.32 (d,1H), 6.94 (d,1H), 5.29 (s,2H), 3.89 (s,3H), 3.41 (s,3H), 2.21 (s,3H), 0.28 (s,9H).

EXAMPLE 3

Preparation of 4-[2-[(2,5-dimethylphenoxy)methyl]-3-thienyl]-2,4-dihydro-5-methoxy-2-methyl-3H-1,2,4-triazol-3-one To a solution of the title compound of Step E in Example 1 (200 mg), 2,5-dimethylphenol (152 mg) and triphenylphosphine (261 mg) in THF (2 mL) at 0° C. (ice bath) under N$_2$ was added diethyl azodicarboxylate (231 mg). The ice bath was removed and the reaction mixture warmed to room temperature. After stirring for 4 h at room temperature, the reaction mixture was concentrated under reduced pressure to give an orange oil. Purification of this orange oil by flash chromatography (1:1 ethyl acetate:hexane eluent) followed by preparative TLC (10% ethyl acetate/methylene chloride) afforded 100 mg of the title compound of Example 3, a compound of the invention, as yellow-brown solid melting at 151–153° C. $^1$H NMR (CDCl$_3$): δ 7.34 (d,$^1$H), 7.01 (d,1H), 6.95 (d,1H), 6.68 (m,2H), 5.15 (s,2H), 3.94 (s,3H), 3.43 (s,3H), 2.30 (s,3H), 2.16 (s,3H).

EXAMPLE 4

Step A: Preparation of 3-(1,5-dihydro-3-methoxy-1-methyl-5-oxo-4H-1,2,4-triazol-4-yl)-2-thiophenecarboxaldehyde A solution of 4-methylmorpholine N-oxide (0.38 g, 0.0033 mol) in dichloromethane (7 mL) was stirred over anhydrous magnesium sulfate for 15 minutes and then filtered. Molecular sieves (4 Å) were added to the filtrate, followed by tetrapropylamrnonium perruthenate (0.11 g, 0.0003 mol). A solution of the title compound of Step E in Example 1 (0.39 g, 0.0016 mol) in dichloromethane (1 mL) was added and the resulting mixture was stired at room temperature for 1 hr. The reaction mixture was diluted with diethyl ether (10 mL), filtered through a short plug of silica gel, and the filtrate was concentrated by rotary evaporation to give 0.21 g of the title compound of Step A as a pale solid. $^1$H NMR (400 MHz, CDCl$_3$): δ 9.84 (s,1H), 7.79 (d,1H, J=5.2 Hz), 7.16 (d,1H, J=5.2 Hz), 4.01 (s,3H), 3.46 (s,3H).

Step B: Preparation of (1,1-dimethylethyl) dichloro (diethoxyphosphinyl)acetate

A solution of 5.25% sodium hypochlorite (Clorox® bleach; 421.5 g, 0.2973 mol) was adjusted to pH 7.1 with 3N HCl. tert-Butyl diethylphosphonoacetate (15.0 g, 0.0595 mol) was added dropwise at 0° C. with vigorous stirring. After complete addition, the ice bath was removed and stirring was continued for 1 h. The reaction mixture was extracted five times with hexane and the combined organic phases were dried (MgSO$_4$), filtered and concentrated to afford 18.4 g of the title compound of Step B as a colorless oil. $^1$H NMR (300 MHz, CDCl$_3$): δ 4.41–4.36 (m,4H), 1.57 (s,9H), 1.40 (t,6H, J=7.2 Hz).

Step C: Preparation of (1,1-dimethylethyl) chloro (diethoxyphosphinyl)acetate

The title compound of Step B (18.4 g, 0.0572 mol) was dissolved in ethanol (140 mL) and cooled to 0° C. A solution of sodium sulfite (14.4 g, 0.1144 mol) in H$_2$O (63 mL) was added with stirring such that the internal temperature remained below 14° C. The cooling bath was removed and the mixture was stirred at room temperature for 30 min. The reaction mixture was extracted five times with chloroform, and the combined organic phase was dried (MgSO$_4$), filtered and concentrated to afford 16.4 g of the title compound of Step C as a clear oil. $^1$H NMR (300 MHz, CDCl$_3$): δ 4.43 (d,1H, J=15.9 Hz), 4.30–4.24 (m,4H), 1.52 (s,9H), 1.38 (t,6H, J=6.9 Hz).

Step D: Preparation of (1,1-dimethylethy) 2-chloro-3-[3-(1, 5-dihydro-3-methoxy-1-methyl-5-oxo-4H-1,2,4-triazol-4-yl)-2-thienyl]-2-propenoate A solution of the title compound of Step C (0.026 g, 0.0009 mol) in ethyl acetate (2 mL) was added to a mixture of calcium hydroxide (0.068 g, 0.0009 mol) and the title compound of Step A (0.220 g, 0.0009 mol) in ethyl acetate (5 mL). The resulting mixture was stirred at 60° C. overnight. Three additional 0.026 g (0.0009 mol) portions of the title compound of Step C were added at 3 h intervals and then the temperature of the mixture was increased to 70° C. and heating was continued overnight. After 40 h of total reaction time, the reaction mixture was poured into ice water and extracted three times with ethyl acetate. The combined organic phase was washed successively with saturated aqueous NaCl and then with a 1/1 mixture of saturated aqueous NaCl and saturated aqueous sodium hydrogen carbonate, dried (Na$_2$SO$_4$), filtered and concentrated to a pale yellow oil. The crude product was purified by flash column chromatography on silica gel to give a preliminary fraction of 0.170 g of the title compound of Step D, a compound of the invention, as a white solid (m.p. 105–115° C.) consisting of a 7:3 ratio of Z- and E-isomers, respectively, followed by a final fraction of 0.04 g of the title compound of Step D, a compound of the invention, as a white solid (m.p. 104° C.) consisting of a 5:1 ratio of Z- and E-isomers, respectively. $^1$H NMR (300 MHz, CDCl$_3$: for the Z/E mixture): δ 7.77 and 7.00 (2d,1H total, J=0.8 Hz), 7.62 and 7.46 (2dd,1H total, J=0.8, 5.4 Hz), 7.09 and 6.98 (2dd,1H total, J=0.9, 5.4 Hz), 3.97 (s,3H), 3.45 (s,3H), 1.54 (s,9H).

EXAMPLE 5

Step A: Preparation of monomethyl 3,4-furandicarboxylate

A solution of NaOH (5.0 g) in H$_2$O/methanol (20 ml/60 mL) was added to a solution of dimethyl 3,4-furandicarboxylate (23 g) in methanol (250 mL) at 0° C. The mixture was allowed to stir at 0° C. for 2 h, and then was warmed to room temperature and left to stir overnight. The congealed mixture was concentrated under reduced pressure and the resulting solid was dissolved in water. The aqueous solution was extracted three times with diethyl ether and the combined organic extracts were dried (MgSO$_4$), filtered and concentrated under reduced pressure to afford a white solid (3.5 g) which was the starting dimethyl 3,4-furandicarboxylate. The remaining aqueous layer was acidified by dropwise addition of concentrated HCl and extracted three times with methylene chloride. The combined methylene chloride extracts were dried (MgSO$_4$), filtered and concentrated under reduced pressure to afford 22.97 g of the title compound of Step A as a white solid. $^1$H NMR (CDCl$_3$): δ 13.02 (br s,1H), 8.25 (d,1H), 8.13 (d,1H), 4.00 (s,3H).

Step B: Preparation of methyl 4-(azidocarbonyl)-3-furancarboxylate

To a solution of the title compound of Step A (23 g), triethylamine (18.8 mL) and DMF (120 mL) at 0° C. under nitrogen was added a solution of diphenylphosphorylazide (29.1 mL) in DMF (20 mL) via an addition funnel. The reaction was allowed to stir for 3 h at 0° C. and was monitored by TLC (1:1 ethyl acetate/hexane). The reaction mixture was poured onto an ice/diethyl ether mixture and then extracted three times with diethyl ether. The combined organic extracts were washed with a 10% aqueous NaHCO$_3$ solution, dried (MgSO$_4$) and concentrated to give 24 g of crude product, the title compound of Step B, as an oil/solid mixture.

Step C: Preparation of methyl 4-[[(2,2-dimethylhydrazino) carbonyl]amino]-3-furancarboxylate A solution of the title compound of Step B (24 g) in toluene (200 mL) was heated at 70° C. for 3 h and then at 90° C. for another 3 h. The reaction was followed by IR. After cooling to 0° C., 1,1-dimethylhydrazine (9.4 mL) was added and the reaction was allowed to stir overnight at room temperature. The resulting precipitate was collected by filtration to afford 13.5 g of the title compound of Step C as a white solid melting at 138–139° C. The filtrate was concentrated under reduced pressure to give a second batch, 15.7 g of crude product, the title compound of Step C, as an orange solid. $^1$H NMR (CDCl$_3$): δ 9.28 (br s,1H), 8.03 (d,1H), 7.85 (d,1H), 5.44 (d,1H), 3.88 (s,3H), 2.62 (s,6H).

Step D: Preparation of methyl 4-(3-chloro-1,5-dihydro-1-methyl-5-oxo-4H-1,2,4-triazol-4-yl)-3-furancarboxylate Triphosgene (40.1 g) was added to a solution of crude title compound of Step C (15.4 g) in methylene chloride (550 mL) at 0° C. The mixture was heated at reflux for 4 h, cooled to room temperature and stirred overnight. The reaction mixture was concentrated to a brown oil which was dissolved in methylene chloride, washed with water and the aqueous layer extracted three times with methylene chloride. The combined organic extracts were dried (MgSO$_4$), filtered and concentrated to a brown oil. Purification by flash chromatography (1:1 hexane:ethyl acetate) provided 5.34 g of the title compound of Step D as a yellow solid melting at 129–130° C. $^1$H NMR (CDCl$_3$): δ 8.10 (d,1H), 7.72 (d,1H), 3.80 (s,3H), 3.52 (s,3H).

Step E: Preparation of methyl 4-(1,5-dihydro-3-methoxy-1-methyl-5-oxo-4H-1,2,4-triazol-4-yl)-3-furancarboxylate A solution of sodium methoxide (11.4 mL, 30% in methanol) was added to a solution of the title compound of Step D (5.34 g) in methanol/dimethoxyethane (26 mL/26 mL) while stirring under nitrogen. The yellow solution was heated to 40° C. for 5 h, cooled to room temperature and left to stir overnight under nitrogen. The reaction mixture was poured into saturated aqueous NH$_4$Cl (50 mL) and the resulting mixture was extracted three times with ethyl acetate. The combined organic extracts were dried (MgSO$_4$), filtered and concentrated to a yellow solid. The yellow solid was dried under vacuum to afford 4.7 g of the title compound of Step E melting at 131–133° C. $^1$H NMR (CDCl$_3$): δ 8.04 (d,1H), 7.68 (d,1H), 3.94 (s,3H), 3.78 (s,3H), 3.43 (s,3H).

Step F: Preparation of 2,4-dihydro-4-[4-(hydroxymethyl)-3-furanyl]-5-methoxy-2-methyl-3H-1,2,4-triazol-3-one A solution of the title compound of Step E (4.6 g) in methylene chloride (40 mL) under nitrogen was cooled to −78° C. while stirring. A solution of diisobutylaluminum hydride (55.0 mL, 1 M in CH$_2$Cl$_2$) in methylene chloride was then added, the reaction mixture was allowed to warm to room temperature and stirred for 1 h. The reaction was monitored by TLC (5% methanol/ethyl acetate). After cooling back down to −78° C., the reaction was diluted with acetone (45 mL), quenched with glacial acetic acid (20 mL) and then allowed to warm to room temperature. The resulting mixture was further diluted with water (200 mL) and extracted successively with methylene chloride and ethyl acetate. The combined organic extracts were dried (MgSO$_4$), filtered and concentrated under reduced pressure to yield 3.62 g of the title compound of Step F as an orange solid melting at 132.5–133.5° C. $^1$H NMR (CDC$_3$): δ 7.53 (s,2H), 4.38 (s,3H), 3.99 (s,3H), 3.44 (s,3H).

Step G: Preparation of 4-[4-(bromomethyl)-3-furanyl]-2,4-dihydro-5-methoxy-2-methyl-3H-1,2,4-triazol-3-one To a solution of the title compound of Step F (3.6 g), and triphenylphosphine (5.1 g) in methylene chloride (40 mL) under N$_2$ at 0° C. was added carbon tetrabromide (8.0 g). The resulting orange solution was allowed to stir overnight at room temperature and then was concentrated under reduced pressure to give a brown oil. The residue was purified by flash chromatography (1:2 ethyl acetate:hexane as eluent) to afford 3.6 g (78%) of the title compound of Step G, a compound of the invention, as a white solid melting at 147–149° C.

EXAMPLE 6

Preparation of 2,4-dihydro-5-methoxy-2-methyl-4-[4-[[[[1-[3-(trimethylsilyl)phenyl]ethylidene]amino]oxy]methyl]-3-furanyl]-3H-1,2,4-triazol-3-one A solution of the title compound of Step D in Example 2 (180 mg) in DMF (2 mL) under N$_2$ was cooled to 0° C. Sodium hydride (27 mg, 95%) was added and the mixture was stirred at 0° C. for 20 min. A solution of the title compound of Step G in Example 5 (250 mg) in DMF (2 mL) was added via syringe and the resulting mixture was allowed to warm to room temperature. The mixture was left to stir overnight at room temperature. The reaction mixture was cooled to 0° C., quenched with water and extracted three times with methylene chloride. The combined organic extracts were dried (MgSO$_4$), filtered and concentrated under reduced pressure to a yellow oil. The oil was purified by flash chromatography (1:2 ethyl acetate:hexane as eluent) to afford 242 mg of the tide compound of Example 6, a compound of the invention, as a clear oil. $^1$H NMR (CDCl$_3$): δ 7.70 (s,1H), 7.54 (m,4H), 7.34 (t,1H), 5.11 (s,2H), 3.86 (s,3H), 3.32 (s,3H), 2.14 (s,3H), 0.28 (s,9H).

EXAMPLE 7

Step A: Preparation of 3,4-dihydro-7-methoxy-N-(phenylmethyl)-1-naphthalenamine

A mixture containing 7-methoxytetralone (25.0 g), benzylamine (15.8 mL), toluene and 4 Å molecular sieves (42.0 g) was heated at reflux for 3.5 h. The mixture was cooled to room temperature, filtered through a layer of Florisil® and concentrated under reduced pressure to yield 42.1 g of crude title compound of Step A.

Step B: Preparation of 7-methoxy-1-naphthalenamine

To a solution of crude title compound of Step A (42.1 g) in diphenyl ether (320 mL) was added 10% palladium on carbon (17.8 g). The heterogeneous black mixture was heated at reflux for 5 h under N$_2$ while stirring. The reaction mixture was allowed to cool to room temperature and filtered. The filtrate was acidified with concentrated HCl and the resulting white precipitate was collected by filtration, washed with CH$_2$Cl$_2$, dissolved in water and treated with 50% aqueous NaOH until basic. The aqueous mixture was then extracted four times with CH$_2$Cl$_2$. The combined organic extracts were dried (MgSO$_4$), filtered and the filtrate was concentrated under reduced pressure to give 20.9 g of the title compound of Step B as a pink solid melting at 79–80° C. $^1$H NMR (CDCl$_3$): δ 7.70 (d,1H), 7.29–7.13 (m,3H), 7.07 (d,1H), 6.80 (dd,1H), 4.0 (br s,2H), 3.94 (s,3H).

Step C: Preparation of 1-isocyanato-7-methoxynaphthalene

To a solution of the title compound of Step B (5.0 g) in p-dioxane (115 mL) at room temperature was added via syringe diphosgene (4.2 mL) followed by the addition of triethylamine (4.8 mL). The mixture was heated at reflux overnight while stirring. The reaction was monitored by IR (2267 cm$^{-1}$). The reaction mixture was filtered and the residue was washed with diethyl ether. The filtrate was concentrated under reduced pressure to give 5.8 g of the title compound of Step C as a beige solid which was used without further purification.

Step D: Preparation of N-(7-methoxy-1-naphthalenyl)-2,2-dimethylhydrazinecarboxamide A solution of crude title compound of Step C (5.8 g) in toluene (85 mL) was cooled to 0° C. under N$_2$. While stirring the reaction solution, 1,1-dimethylhydrazine (2.5 mL) was added and the mixture was allowed to warm to room temperature. After stirring for 30 min at room temperature, a precipitate formed. Filtration afforded 5.1 g of the title compound of Step D as a white solid melting at 152–153° C. $^1$H NMR (CDCl$_3$): δ 8.48 (br s,1H), 7.89 (d,1H), 7.77 (m,1H), 7.58 (d,1H), 7.34 (t,1H), 7.17 (m,2H), 5.72 (br s,1H), 3.93 (s,3H), 2.72 (s,6H).

Step E: Preparation of 5-chloro-2,4-dihydro-4-(7-methoxy-1-naphthalenyl)-2-methyl-3H-1,2,4-triazol-3-one A solution of triphosgene (16.7 g) in ethyl acetate (130 mL) was heated to reflux and a suspension of the title compound of Step D (4.9 g) in ethyl acetate was added via cannula and the aid of a mechanical pump over a period of 40 min. The temperature was held at approximately 75° C. during the addition. After the addition was complete, the reaction mixture was heated at reflux for 2 h, cooled to room temperature and stirred overnight at room temperature. The reaction mixture was poured into a solution of saturated aqueous sodium bicarbonate, extracted with ethyl acetate, and the combined organic extracts were dried (MgSO$_4$), filtered and concentrated under reduced pressure to afford 4.9 g of the title compound of Step E as a white solid melting at 142–143° C. $^1$H NMR (CDCl$_3$): δ 7.93 (dd,1H), 7.84 (d,1H), 7.43 (m,2H), 7.24 (dd,1H), 6.75 (d,1H), 3.87 (s,3H), 3.62 (s,3H).

Step F: Preparation of 5-chloro-2,4-dihydro-4-(7-hydroxy-1-naphthalenyl)-2-methyl-3H-1,2,4-triazol-3-one A solution of the title compound of Step E (2.9 g) in methylene chloride (35 mL) was cooled to 0° C. while stirring under $N_2$, and aluminum trichloride (4.0 g) was added in portions. The reaction mixture was allowed to warm to room temperature and then was heated to reflux for 18 h. The reaction mixture was cooled to room temperature, poured into water and extracted with ethyl acetate. The combined organic extracts were dried ($MgSO_4$), filtered and concentrated under reduced pressure. The crude material was purified by flash chromatography (1:4 ethyl acetate-:hexane as eluent) to afford 2.2 g of the title compound of Step F. $^1$H NMR ($Me_2SO$-$d_6$): δ 10.08 (s,1H), 8.02 (d,1H), 7.95 (d,1H), 7.59 (dd,1H), 7.41 (t,1H), 7.18 (dd,1H), 6.71 (d,1H), 3.49 (s,3H).

Step G: Preparation of 2,4-dihydro-4-(7-hydroxy-1-naphthalenyl)-5-methoxy-2-methyl-3H-1,2,4-triazol-3-one To a solution of the tide compound of Step F (3.3 g) in THF (38 mL) was added a solution of sodium methoxide (6.5 mL, 30% in methanol) while stiring under $N_2$. The mixture was heated at 50° C. for 6 h and cooled to room temperature and left to stir overnight. The reaction was quenched with water and extracted three times with methylene chloride and then three times with ethyl acetate. The combined organic extracts were dried ($MgSO_4$), filtered and concentrated under reduced pressure. Trituration (ethyl acetate:hexane 1:1) of the crude product provided 1.61 g of the title compound of Step G as a light brown solid melting at greater than 250° C. $^1$H NMR ($Me_2SO$-$d_6$): δ 10.00 (s,1H), 7.93 (m,2H), 7.47 (dd,1H), 7.36 (t,1H), 7.15 (dd,1H), 6.73 (d,1H), 3.86 (s,3H), 3.39 (s,3H).

Step H: Preparation of 5-chloro-3-[4-(trifluoromethyl)phenyl]-1,2,4-thiadiazole

A mixture of 4-(trifluoromethyl)benzamidine hydrochloride dihydrate (5.0 g), water (50 mL), methylene chloride (100 mL), benzyltriethylammonium chloride (0.44 g), and perchloromethyl mercaptan (2.1 mL) was prepared at room temperature and then cooled to 0° C. A solution of sodium hydroxide (3.07 g) in water (50 mL) was added via an addition funnel while maintaining the temperature below 10° C. The reaction was left to stir overnight at room temperature. The mixture was transferred to a separatory funnel and the two layers were separated. The organic layer was washed with saturated sodium bicarbonate, dried ($MgSO_4$), filtered and concentrated under reduced pressure. The crude material was purified by flash chromatography (hexane as eluent) to afford 3.7 g of the title compound of Step H as a white powder. $^1$H NMR ($CDCl_3$): δ 8.36 (d,2H), 7.73 (d,2H).

Step I: Preparation of 2,4-dihydro-5-methoxy-2-methyl-4-[7-[[3-[4-(trifluoromethyl)phenyl]-1,2,4-thiadiazol-5-yl]oxy]-1-naphthalenyl]-3H-1,2,4-triazol-3-one A solution of the title compound of Step G (214 mg) and the title compound of Step H (251 mg) in DMF (5 mL) was cooled to 0° C. under $N_2$. To the resulting yellow solution was added sodium hydride (25 mg) and the mixture was left to stir overnight at room temperature. The reaction was then cooled to 0° C., quenched with water and extracted twice with ethyl acetate. The combined organic extracts were dried ($MgSO_4$), filtered and concentrated under reduced pressure. The crude yellow solid was purified by crystallization in methanol to afford 216 mg of the title compound of Step I, a compound of the invention as a white powder melting at 216–217° C. $^1$H NMR ($Me_2SO$-$d_6$): δ 8.30 (m,3H), 8.23 (dd,1H), 7.98 (d,1H), 7.91–7.81 (m,3H), 7.73 (m,2H), 3.86 (s,3H), 3.33 (s,3H).

EXAMPLE 8

Step A: Preparation of 3-nitro-2-(3-phenoxyphenoxy)pyridine

3-Phenoxyphenol (3 g, 16.1 mmol) was added to a solution of potassium t-butoxide (1.90 g of 90%, 16.6 mmol) in 50 mL of dry tetrahydrofuran at room temperature after which the reaction was stirred at room temperature for 10 min. Then, 2-chloro-3-nitropyridine (2.56 g, 16.1 mmol) was added. The reaction mixture was stirred at room temperature for 16 h. The reaction mixture was concentrated under reduced pressure. The residue was diluted with water, extracted twice with methylene chloride and dried over magnesium sulfate. The solvent was then removed to yield the title compound of Step A as an oil. $^1$H NMR ($CDCl_3$; 300 MHz): δ 6.85 (m,1H), 6.90 (m,2H), 7.0–7.2 (m,4H), 7.3–7.4 (m,3H), 8.35 (m,2H).

Step B: Preparation of 3-isocyanato-2-(3-phenoxyphenoxy)pyridine

A solution of the entire amount of the intermediate in Step A and 6 mL water in 60 mL acetic acid was heated on a steam bath to 65° C. and at this temperature iron powder (3.05 g, 54.6 mmol) was added portionwise noting the exotherm after each addition. The reaction temperature was kept between 65–85° C. by the addition rate and by a water cooling bath. After stirring for an additional 10 min at 85° C., the reaction was cooled to room temperature, diluted with methylene chloride and filtered through Celite®. The filtrate was washed once with water, then once with saturated sodium bicarbonate, and dried over magnesium sulfate. The solvent was then removed under reduced pressure to yield an oil. This intermediate oil was then dissolved in 60 mL of dry toluene and to this solution was added diphosgene (3.29 g, 16.6 mmol). The mixture was then refluxed with a water scrubber in place for 4 h. The reaction was cooled to room temperature, concentrated under reduced pressure to give crude title compound of Step B as solids which were used entirely in the next reaction (Step C).

Step C: Preparation of 5-chloro-2,4-dihydro-2-methyl-4-[2-(3-phenoxyphenoxy)-3-pyridinyl]-3H-1,2,4-triazol-3-one The solids from Step B were dissolved in 100 mL of dry tetrahydrofuran. 1,1-Dimethylhydrazine (3 g, 50.0 mmol) was added and the reaction mixture was stirred at room temperature for 16 h. The reaction mixture was concentrated under reduced pressure. The residue was diluted with water and extracted twice with diethyl ether. The combined organic layers were then washed once with saturated aqueous NaCl solution and dried over magnesium sulfate. The solvent was removed under reduced pressure to give an oil. This oil was then dissolved in 200 mL methylene chloride and cooled to 0° C. at which temperature triphosgene (4.08 g, 13.7 mmol) was added. The reaction mixture was refluxed for 16 h, cooled to room temperature and washed once with water. The organic layer was then dried over magnesium sulfate and concentrated under reduced pressure to yield a crude oil which was purified by silica gel chromatography using 3:2/hexanes:ethyl acetate as the eluent to yield 2 g of the title compound of Step C, a compound of the invention, as a solid. $^1$H NMR ($CDCl_3$; 300 MHz): δ 3.53 (s,3H), 6.8–6.9 (m,3H), 7.0–7.2 (m,4H), 7.3–7.4 (m,3H), 7.71 (dd, 1H, J=1.9, 7.7 Hz), 8.27 (dd,1H, J=1.8, 4.9 Hz).

EXAMPLE 9

Preparation of 2,4-dihydro-5-methoxy-2-methyl-4-[2-(3-phenoxyphenoxy)-3-pyridinyl]-3H-1,2,4-triazol-3-one The title compound of Step C in Example 8 (2 g, 5.26 mmol) was dissolved in 100 mL of methanol and to this solution was added sodium methoxide (1.90 g 30% solution in methanol, 10.5 mmol) at room temperature. The reaction was subsequently refluxed for 6 h, cooled to room temperature and concentrated under reduced pressure to semisolids. The semisolids were diluted with water, extracted twice with methylene chloride and dried over magnesium sulfate. The solvent was removed under reduced pressure to yield an oil which was subsequently purified by silica gel chromatography using 1:2/hexanes:ethyl acetate as the eluent to yield 0.90 g of the title compound of Step D, compound of the invention, as a solid melting at 113–114° C. $^1$H NMR (CDCl$_3$; 400 MHz): δ 3.44 (s,3H), 3.91 (s,3H), 6.80 (m,1H), 6.85 (m,2H), 7.06 (dd,2H, J=1.1, 8.6 Hz), 7.12 (dd,2H, J=4.9, 7.6 Hz), 7.3–7.4 (m,3H), 7.71 (dd,1H, J=1.8, 7.6 Hz), 8.21 (dd,1H, J=1.9, 4.9 Hz).

EXAMPLE 10

2,4-dihydro-5-methoxy-2-methyl-4-[2-[[[3-[4-(trifluoromethyl)phenyl]-1,2,4-thiadiazol-5-yl]oxy]methyl]-3-thienyl]-3H-1,2,4-triazol-3-one A solution of the title compound of Step E in Example 1 (250 mg) and the title compound of Step H in Example 7 (329 mg) in DMF (5 mL) was cooled to 0° C. under N$_2$. To the resulting yellow solution was added sodium hydride (32 mg) and the mixture was left to stir overnight at room temperature. The reaction mixture was poured into water and extracted three times with CH$_2$Cl$_2$. The combined organic extracts were dried (MgSO$_4$), filtered and concentrated under reduced pressure. The resulting crude yellow solid was purified by crystallization in hexane:ethyl acetate (1:1) to afford 191 mg of the title compound of Example 10, a compound of the invention, as a white powder melting at 138–139° C. $^1$H NMR (CDCl$_3$): δ 8.29 (d,2H), 7.71 (d,2H), 7.44 (d,1H), 6.98 (d,1H), 5.75 (s,2H), 3.91 (s,3H), 3.43 (s,3H).

By the procedures described herein together with methods known in the art, the following compounds of Tables 1 to 21 can be prepared. The following abbreviations are used in the Tables which follow: t=tertiary, s=secondary, n=normal, i=iso, c=cyclo, Me=methyl, Et=ethyl, Pr=propyl, i-Pr=isopropyl, Bu=butyl, Ph=phenyl, nap=naphthalenyl, MeO=methoxy, EtO=ethoxy, PhO=phenoxy, MeS=methylthio, EtS=ethylthio, CN=cyano, NO$_2$=nitro, TMS=trimethylsilyl, S(O)Me=methylsulfinyl, and S(O)$_2$Me=methylsulfonyl.

TABLE 1

Compounds of Formula I where A = N, G = N, W = O, X = OMe, R$^2$ = Me, Y = CH$_2$O—N=C(Me), Z = 3-CF$_3$-Ph, the floating double bond is attached to A and

TABLE 2

Compounds of Formula I where A = O, G = C, W = O, X = OMe, R² = Me,
Y = CH₂O—N=C(Me), Z = 3-CF₃-Ph, the floating double bond is attached to G and

E—Y—Z    E—Y—Z    E—Y—Z    E—Y—Z    E—Y—Z

[Structures of various heterocyclic E groups connected to Y—Z: thiophenes, furans, pyridines, naphthalenes, pyrazines, indoles, benzofuran, benzothiophene, pyrroles, thiazole, oxazole, pyrazoles, imidazoles]

TABLE 3

Compounds of Formula I defined as:

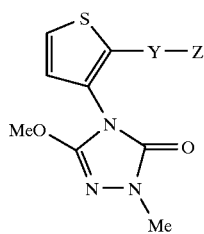

| Y | Y |
|---|---|
| Z = 3-CF₃-Ph | |
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |

TABLE 3-continued

Compounds of Formula I defined as:

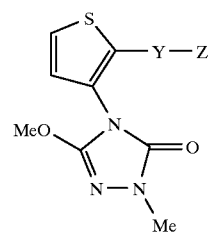

| Y | Y |
|---|---|
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |

TABLE 3-continued

Compounds of Formula I defined as:

[Structure: thiophene ring with S at top, substituted at 2-position with Y—Z, and at 3-position with N of a triazolone ring bearing MeO and N—Me substituents, C=O]

| Y | Y |
|---|---|
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂CO(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

Z = 3-Me₃Si—Ph

| Y | Y |
|---|---|
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂CO(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

TABLE 3-continued

Compounds of Formula I defined as:

[Structure: same thiophene-triazolone structure as above]

| Y | Y |
|---|---|
| Z = 4-CF₃-2-pyridinyl | |
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂OC(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

TABLE 4

Compounds of Formula I defined as:

[Structure: thiophene with S at top, substituted at 2-position with Y—Z, and at 3-position with an isoxazolone ring bearing MeO and N—Me substituents, C=O]

| Y | Y |
|---|---|
| Z = 3-CF₃-Ph | |
| S | CH₂CH₂ |

TABLE 4-continued

Compounds of Formula I defined as:

[Structure: thiophene connected to MeO-substituted isoxazolinone with Y—Z substituent]

| Y | Y |
|---|---|
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂CO(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

Z = 3-Me₃Si—Ph

| Y | Y |
|---|---|
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |

Z = 4-CF₃-2-pyridinyl

| Y | Y |
|---|---|
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂OC(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

TABLE 5

Compounds of Formula I defined as:

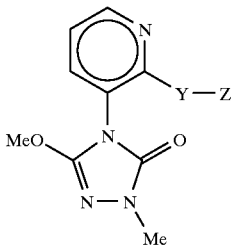

| Y | Y |
|---|---|
| Z = 3-CF$_3$-Ph | |
| S | CH$_2$CH$_2$ |
| CH=CH | CH(Me)CH$_2$ |
| C(Me)=CH | CH$_2$CH(Me) |
| CH=C(Me) | CH(Me)CH(Me) |
| C(Me)=C(Me) | CH$_2$O |
| S(O)$_2$ | CH=C(Cl)C(=O)O |
| CH$_2$O—N=C(CN) | CH=N—O—CH$_2$ |
| CH$_2$O—N=C(c-Pr) | CH=N—O—CH(Me) |
| CH$_2$O—N=C(CN)C(=O) | CH$_2$O—N=C(Et) |
| CH$_2$O—N=C(NHMe) | CH$_2$O—N=C(NH$_2$) |
| CH$_2$O—N(Me)C(=O)N(Me) | CH$_2$O—N(Me)C(=S)N(Me) |
| CH$_2$SC(SMe)=N | CH=N—N(Me) |
| CH$_2$OC(=O)O | CH$_2$OC(=S)O |
| CH$_2$SC(=O)N(Me) | CH$_2$SC(=O)NH |
| CH$_2$SC(=O)O | CH$_2$SC(=S)O |
| CH$_2$SC(=NMe)S | CH$_2$N(Me)C(=O)N(Me) |
| CH$_2$O—N=C(Me)CH$_2$S | CH$_2$O—N=C(SMe)CH$_2$S |
| O—N=CH | O—N=C(Me) |
| S(O) | CH$_2$SC(Et)=N |
| CH(Me)O | SCH$_2$ |
| OCH$_2$ | SCH(Me) |
| OCH(Me) | CH$_2$O—N=CH |
| CH$_2$S | |
| CH(Me)S | CH=N—O |
| O | C(=O) |
| CH$_2$OC(=O)NH | CH$_2$O—N=C(SMe) |
| CH$_2$O—N=C(OMe) | N=C(Cl)C(=O)O |
| CH$_2$O—N=C(Cl) | CH$_2$O—N=C(CF$_3$) |
| CH$_2$CO(=S)NH | CH$_2$OC(=S)N(Me) |
| CH$_2$O—N=C(Me)N(Me) | CH$_2$O—N=C(Me)OCH$_2$ |
| CH$_2$O—N=C(Me)N=N | CH$_2$N(Me)—N=C(Me) |
| CH$_2$OC(=O)S | CH$_2$OC(=S)S |
| CH$_2$SC(=S)N(Me) | CH$_2$SC(=S)S |
| CH$_2$SC(=O)S | CH$_2$O—N=C(SMe)CH$_2$O |
| CH$_2$O—N=C(Me)CH$_2$O | CH$_2$OC(Me)=C(CN) |
| OCH$_2$CH$_2$O—N=C(Me) | C(Me)=N—O |
| CH=N—N=C(Me) | C≡C |
| C≡C—C(=O)O | CH$_2$SC(c-Pr)=N |
| Z = 3-Me$_3$Si—Ph | |
| S | CH$_2$CH$_2$ |
| CH=CH | CH(Me)CH$_2$ |
| C(Me)=CH | CH$_2$CH(Me) |
| CH=C(Me) | CH(Me)CH(Me) |
| C(Me)=C(Me) | CH$_2$O |
| S(O)$_2$ | CH=C(Cl)C(=O)O |
| CH$_2$O—N=C(CN) | CH=N—O—CH$_2$ |
| CH$_2$O—N=C(c-Pr) | CH=N—O—CH(Me) |
| CH$_2$O—N=C(CN)C(=O) | CH$_2$O—N=C(Et) |
| CH$_2$O—N=C(NHMe) | CH$_2$O—N=C(NH$_2$) |
| CH$_2$O—N(Me)C(=O)N(Me) | CH$_2$O—N(Me)C(=S)N(Me) |
| CH$_2$SC(SMe)=N | CH=N—N(Me) |
| CH$_2$OC(=O)O | CH$_2$OC(=S)O |
| CH$_2$SC(=O)N(Me) | CH$_2$SC(=O)NH |
| CH$_2$SC(=O)O | CH$_2$SC(=S)O |
| CH$_2$SC(=NMe)S | CH$_2$N(Me)C(=O)N(Me) |
| CH$_2$O—N=C(Me)CH$_2$S | CH$_2$O—N=C(SMe)CH$_2$S |
| O—N=CH | O—N=C(Me) |
| S(O) | CH$_2$SC(Et)=N |

TABLE 5-continued

Compounds of Formula I defined as:

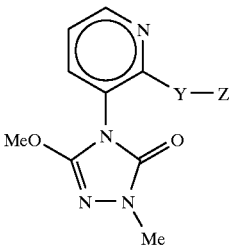

| Y | Y |
|---|---|
| CH(Me)O | SCH$_2$ |
| OCH$_2$ | SCH(Me) |
| OCH(Me) | CH$_2$O—N=CH |
| CH$_2$S | |
| CH(Me)S | CH=N—O |
| O | C(=O) |
| CH$_2$OC(=O)NH | CH$_2$O—N=C(SMe) |
| CH$_2$O—N=C(OMe) | N=C(Cl)C(=O)O |
| CH$_2$O—N=C(Cl) | CH$_2$O—N=C(CF$_3$) |
| CH$_2$CO(=S)NH | CH$_2$OC(=S)N(Me) |
| CH$_2$O—N=C(Me)N(Me) | CH$_2$O—N=C(Me)OCH$_2$ |
| CH$_2$O—N=C(Me)N=N | CH$_2$N(Me)—N=C(Me) |
| CH$_2$OC(=O)S | CH$_2$OC(=S)S |
| CH$_2$SC(=S)N(Me) | CH$_2$SC(=S)S |
| CH$_2$SC(=O)S | CH$_2$O—N=C(SMe)CH$_2$O |
| CH$_2$O—N=C(Me)CH$_2$O | CH$_2$OC(Me)=C(CN) |
| OCH$_2$CH$_2$O—N=C(Me) | C(Me)=N—O |
| CH=N—N=C(Me) | C≡C |
| C≡C—C(=O)O | CH$_2$SC(c-Pr)=N |
| Z = 4-CF$_3$-2-pyridinyl | |
| S | CH$_2$CH$_2$ |
| CH=CH | CH(Me)CH$_2$ |
| C(Me)=CH | CH$_2$CH(Me) |
| CH=C(Me) | CH(Me)CH(Me) |
| C(Me)=C(Me) | CH$_2$O |
| S(O)$_2$ | CH=C(Cl)C(=O)O |
| CH$_2$O—N=C(CN) | CH=N—O—CH$_2$ |
| CH$_2$O—N=C(c-Pr) | CH=N—O—CH(Me) |
| CH$_2$O—N=C(CN)C(=O) | CH$_2$O—N=C(Et) |
| CH$_2$O—N=C(NHMe) | CH$_2$O—N=C(NH$_2$) |
| CH$_2$O—N(Me)C(=O)N(Me) | CH$_2$O—N(Me)C(=S)N(Me) |
| CH$_2$SC(SMe)=N | CH=N—N(Me) |
| CH$_2$OC(=O)O | CH$_2$OC(=S)O |
| CH$_2$SC(=O)N(Me) | CH$_2$SC(=O)NH |
| CH$_2$SC(=O)O | CH$_2$SC(=S)O |
| CH$_2$SC(=NMe)S | CH$_2$N(Me)C(=O)N(Me) |
| CH$_2$O—N=C(Me)CH$_2$S | CH$_2$O—N=C(SMe)CH$_2$S |
| O—N=CH | O—N=C(Me) |
| S(O) | CH$_2$SC(Et)=N |
| CH(Me)O | SCH$_2$ |
| OCH$_2$ | SCH(Me) |
| OCH(Me) | CH$_2$O—N=CH |
| CH$_2$S | |
| CH(Me)S | CH=N—O |
| O | C(=O) |
| CH$_2$OC(=O)NH | CH$_2$O—N=C(SMe) |
| CH$_2$O—N=C(OMe) | N=C(Cl)C(=O)O |
| CH$_2$O—N=C(Cl) | CH$_2$O—N=C(CF$_3$) |
| CH$_2$OC(=S)NH | CH$_2$OC(=S)N(Me) |
| CH$_2$O—N=C(Me)N(Me) | CH$_2$O—N=C(Me)OCH$_2$ |
| CH$_2$O—N=C(Me)N=N | CH$_2$N(Me)—N=C(Me) |
| CH$_2$OC(=O)S | CH$_2$OC(=S)S |
| CH$_2$SC(=S)N(Me) | CH$_2$SC(=S)S |
| CH$_2$SC(=O)S | CH$_2$O—N=C(SMe)CH$_2$O |
| CH$_2$O—N=C(Me)CH$_2$O | CH$_2$OC(Me)=C(CN) |
| OCH$_2$CH$_2$O—N=C(Me) | C(Me)=N—O |
| CH=N—N=C(Me) | C≡C |
| C≡C—C(=O)O | CH$_2$SC(c-Pr)=N |

TABLE 6

Compounds of Formula I defined as:

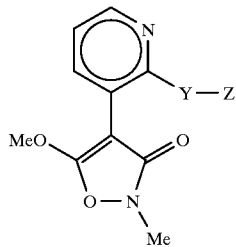

| Y | Y |
|---|---|
| Z = 3-CF₃-Ph | |
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂CO(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |
| Z = 3-Me₃Si—Ph | |
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |

TABLE 6-continued

Compounds of Formula I defined as:

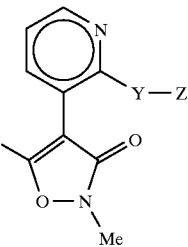

| Y | Y |
|---|---|
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂CO(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | |
| Z = 4-CF₃-2-pyridinyl | |
| S | CH₂CH₂ |
| CH=CH | CH(Me)CH₂ |
| C(Me)=CH | CH₂CH(Me) |
| CH=C(Me) | CH(Me)CH(Me) |
| C(Me)=C(Me) | CH₂O |
| S(O)₂ | CH=C(Cl)C(=O)O |
| CH₂O—N=C(CN) | CH=N—O—CH₂ |
| CH₂O—N=C(c-Pr) | CH=N—O—CH(Me) |
| CH₂O—N=C(CN)C(=O) | CH₂O—N=C(Et) |
| CH₂O—N=C(NHMe) | CH₂O—N=C(NH₂) |
| CH₂O—N(Me)C(=O)N(Me) | CH₂O—N(Me)C(=S)N(Me) |
| CH₂SC(SMe)=N | CH=N—N(Me) |
| CH₂OC(=O)O | CH₂OC(=S)O |
| CH₂SC(=O)N(Me) | CH₂SC(=O)NH |
| CH₂SC(=O)O | CH₂SC(=S)O |
| CH₂SC(=NMe)S | CH₂N(Me)C(=O)N(Me) |
| CH₂O—N=C(Me)CH₂S | CH₂O—N=C(SMe)CH₂S |
| O—N=CH | O—N=C(Me) |
| S(O) | CH₂SC(Et)=N |
| CH(Me)O | SCH₂ |
| OCH₂ | SCH(Me) |
| OCH(Me) | CH₂O—N=CH |
| CH₂S | |
| CH(Me)S | CH=N—O |
| O | C(=O) |
| CH₂OC(=O)NH | CH₂O—N=C(SMe) |
| CH₂O—N=C(OMe) | N=C(Cl)C(=O)O |
| CH₂O—N=C(Cl) | CH₂O—N=C(CF₃) |
| CH₂OC(=S)NH | CH₂OC(=S)N(Me) |
| CH₂O—N=C(Me)N(Me) | CH₂O—N=C(Me)OCH₂ |
| CH₂O—N=C(Me)N=N | CH₂N(Me)—N=C(Me) |
| CH₂OC(=O)S | CH₂OC(=S)S |
| CH₂SC(=S)N(Me) | CH₂SC(=S)S |
| CH₂SC(=O)S | CH₂O—N=C(SMe)CH₂O |
| CH₂O—N=C(Me)CH₂O | CH₂OC(Me)=C(CN) |
| OCH₂CH₂O—N=C(Me) | C(Me)=N—O |
| CH=N—N=C(Me) | C≡C |
| C≡C—C(=O)O | CH₂SC(c-Pr)=N |

TABLE 7

Compounds of the Formula I defined as:

[Structure: thiophene ring with N-linked triazolinone bearing MeO and N-Me groups, and CH2-O-N=C(Me)-Z substituent]

| Z | Z |
|---|---|
| 2-Br-Ph | PhCH=CHCH2 |
| 2-CN-Ph | 2-Me-Ph |
| 2,4-diCl-Ph | 2-F-Ph |
| 2-CF3-Ph | 2-Me-4-Cl-Ph |
| 2-I-Ph | 4-Ph-Ph |
| c-hexyl | 3-(2-Cl-PhO)-Ph |
| 4-NO2-Ph | 3,5-diCl-Ph |
| PhCH2CH2 | 3,5-diCF3-Ph |
| (2-CN-Ph)CH2 | 2-MeO-Ph |
| CF3CH2 | 2,6-diMeO-Ph |
| 2-MeS-Ph | 3-(2-CN-PhO)-Ph |
| 2-CF3O-Ph | 5-PhO-3-pyridinyl |
| 4-Me-Ph | 6-Me-2-pyridinyl |
| 4-Cl-Ph | 3-CF3O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF3-Ph | 4-NO2-Ph |
| 3,4-diCl-Ph | 4-F-Ph |
| 3,4-diCF3-Ph | 3-Ph-Ph |
| 3-EtO-Ph | 3,4-diMe-Ph |
| Ph | 3,5-diMe-Ph |
| 2-nap | 3-MeS-Ph |
| 3-SF5-Ph |  |
| t-Bu | 4-Me3Si-Ph |
| 4-F-3-CF3-Ph | 3-Me3Ge-Ph |
| 5-F-3-CF3-Ph | 4-Me3Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyol |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF3-PhO)-Ph | 6-(2-NO2-PhO)-4-pyrimidinyl |
| 3-(2-Me-PhO)-Ph | 6-(2-Cl-PhO)-4-pyrimidinyl |
| 5-PbO-2-pyridinyl | 6-(2-CF3-PhO)-4-pyrimidinyl |
| 6-PhO-2-pyridinyl | 4,6-diMeO-2-pyrimidinyl |
| 6-CF3-2-pyridinyl | 4,6-diMe-2-pyrimidinyl |
| 6-PhO-3-pyridinyl | 6-CF3-4-pyrimidinyl |
| 2-pyrimidinyl |  |
| 4-pyrimidinyl | 4-CF3-2-pyrimidinyl |
| 4-MeO-2-pyrimidinyl | 6-CF3-2-pyrazinyl |
| 4-Me-2-pyrimidinyl | 5-CF3-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF2H-Ph | 4-t-Bu-2-pyridinyl |
| 4-OCF2H-Ph | 4-Ph-2-pyridinyl |
| 5-Me-2-nap | 4-Me3Si-2-pyridinyl |
| 6-Me3Si-2-nap | 5-Me3Ge-2-pyridinyl |
| 7-OCF3-2-nap | 4-CF3-2-nap |

TABLE 8

Compounds of the Formula I defined as:

[Structure: naphthalene ring with N-linked triazolinone bearing MeO and N-Me groups, and CH2-O-N=C(Me)-Z substituent]

| Z | Z |
|---|---|
| 2-Br-Ph | PhCH=CHCH2 |
| 2-CN-Ph | 2-Me-Ph |
| 2,4-diCl-Ph | 2-F-Ph |
| 2-CF3-Ph | 2-Me-4-Cl-Ph |
| 2-I-Ph | 4-Ph-Ph |
| c-hexyl | 3-(2-Cl-PhO)-Ph |
| 4-NO2-Ph | 3,5-diCl-Ph |
| PhCH2CH2 | 3,5-diCF3-Ph |
| (2-CN-Ph)CH2 | 2-MeO-Ph |
| CF3CH2 | 2,6-diMeO-Ph |
| 2-MeS-Ph | 3-(2-CN-PhO)-Ph |
| 2-CF3O-Ph | 5-PhO-3-pyridinyl |
| 4-Me-Ph | 6-Me-2-pyridinyl |
| 4-Cl-Ph | 3-CF3O-Ph |
| 3-Me-Ph | 4-Br-Ph |
| 3-CF3-Ph | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF3-Ph | 4-NO2-Ph |
| 3,4-diCl-Ph | 4-F-Ph |
| 3,4-diCF3-Ph | 3-Ph-Ph |
| 3-EtO-Ph | 3,4-diMe-Ph |
| Ph | 3,5-diMe-Ph |
| 2-nap | 3-MeS-Ph |
| 3-SF5-Ph | 3-Me3Si-Ph |
| t-Bu | 4-Me3Si-Ph |
| 4-F-3-CF3-Ph | 3-Me3Ge-Ph |
| 5-F-3-CF3-Ph | 4-Me3Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyol |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF3-PhO)-Ph | 6-(2-NO2-PhO)-4-pyrimidinyl |
| 3-(2-Me-PhO)-Ph | 6-(2-Cl-PhO)-4-pyrimidinyl |
| 5-PbO-2-pyridinyl | 6-(2-CF3-PhO)-4-pyrimidinyl |
| 6-PhO-2-pyridinyl | 4,6-diMeO-2-pyrimidinyl |
| 6-CF3-2-pyridinyl | 4,6-diMe-2-pyrimidinyl |
| 6-PhO-3-pyridinyl | 6-CF3-4-pyrimidinyl |
| 2-pyrimidinyl |  |
| 4-pyrimidinyl | 4-CF3-2-pyrimidinyl |
| 4-MeO-2-pyrimidinyl | 6-CF3-2-pyrazinyl |
| 4-Me-2-pyrimidinyl | 5-CF3-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF2H-Ph | 4-t-Bu-2-pyridinyl |
| 4-OCF2H-Ph | 4-Ph-2-pyridinyl |
| 5-Me-2-nap | 4-Me3Si-2-pyridinyl |
| 6-Me3Si-2-nap | 5-Me3Ge-2-pyridinyl |
| 7-OCF3-2-nap | 4-CF3-2-nap |

TABLE 9

Compounds of the Formula I defined as:

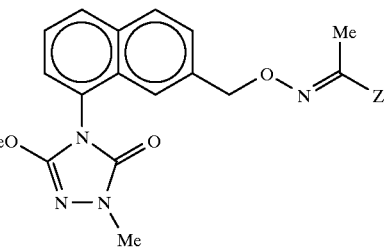

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
| 3-CF$_3$-Ph | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph | 3-Me$_3$Si-Ph |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyridinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl | 4-CF$_3$-2-pyridinyl |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 10

Compounds of the Formula I defined as:

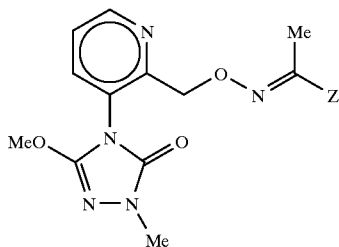

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph |  |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyridinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 11

Compounds of the Formula I defined as:

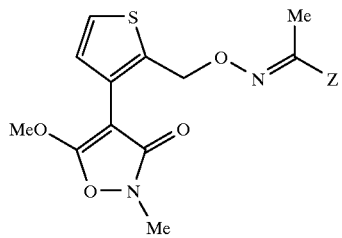

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph |  |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 12

Compounds of the Formula I defined as:

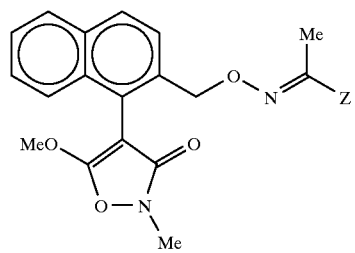

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph | 3-Me$_3$Si-Ph |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 13

Compounds of the Formula I defined as:

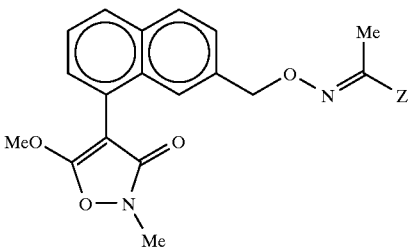

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
| 3-CF$_3$-Ph | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph | 3-Me$_3$Si-Ph |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyridinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl | 4-CF$_3$-2-pyridinyl |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 14

Compounds of the Formula I defined as:

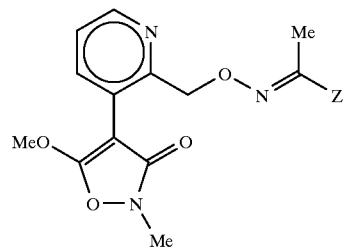

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph |  |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyridinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 15

Compounds of the Formula I defined as:

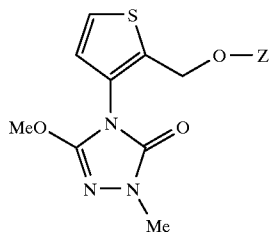

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph |  |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 16

Compounds of the Formula I defined as:

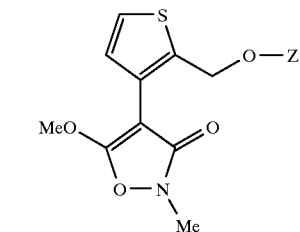

| Z | Z |
|---|---|
| 2-Br-Ph | PhCH=CHCH$_2$ |
| 2-CN-Ph | 2-Me-Ph |
| 2,4-diCl-Ph | 2-F-Ph |
| 2-CF$_3$-Ph | 2-Me-4-Cl-Ph |
| 2-I-Ph | 4-Ph-Ph |
| c-hexyl | 3-(2-Cl-PhO)-Ph |
| 4-NO$_2$-Ph | 3,5-diCl-Ph |
| PhCH$_2$CH$_2$ | 3,5-diCF$_3$-Ph |
| (2-CN-Ph)CH$_2$ | 2-MeO-Ph |
| CF$_3$CH$_2$ | 2,6-diMeO-Ph |
| 2-MeS-Ph | 3-(2-CN-PhO)-Ph |
| 2-CF$_3$O-Ph | 5-PhO-3-pyridinyl |
| 4-Me-Ph | 6-Me-2-pyridinyl |
| 4-Cl-Ph | 3-CF$_3$O-Ph |
| 3-Me-Ph | 4-Br-Ph |
|  | 3-Et-Ph |
| 3-Cl-2-Me-Ph | 4-MeO-Ph |
| 3-t-Bu-Ph | 4-t-Bu-Ph |
| 3-F-Ph | 4-CN-Ph |
| 4-CF$_3$-Ph | 4-NO$_2$-Ph |
| 3,4-diCl-Ph | 4-F-Ph |
| 3,4-diCF$_3$-Ph | 3-Ph-Ph |
| 3-EtO-Ph | 3,4-diMe-Ph |
| Ph | 3,5-diMe-Ph |
| 2-nap | 3-MeS-Ph |
| 3-SF$_5$-Ph |  |
| t-Bu | 4-Me$_3$Si-Ph |
| 4-F-3-CF$_3$-Ph | 3-Me$_3$Ge-Ph |
| 5-F-3-CF$_3$-Ph | 4-Me$_3$Ge-Ph |
| PhC≡CCH2 | 4-PhO-2-pyridinyl |
| 2-Et-Ph | 6-(2-CN-PhO)-4-pyrimidinyl |
| 2-Cl-Ph | 6-PhO-4-pyrimidinyl |
| 2,4,6-triCl-Ph | 4-EtO-2-pyrimidinyl |
| 3-PhO-Ph | 3-(4-pyrimidinyloxy)-Ph |
| 3-(2-Et-PhO)-Ph | 4-(2-thienyl)Ph |
| 6-Ph-2-pyridinyl | 3-(2-pyridinyloxy)Ph |
| 6-PhO-4-pyridinyl | 4-(3-Cl-2-pyridinyloxy)-Ph |
| 3-thienyloxy-Ph | 5-PhO-2-pyrimidinyl |
| 3-(4-CF$_3$-PhO)-Ph | 6-(2-NO$_2$-PhO)-4-pyrimidinyl |
| 3-(2-Me-PhO)-Ph | 6-(2-Cl-PhO)-4-pyrimidinyl |
| 5-PbO-2-pyridinyl | 6-(2-CF$_3$-PhO)-4-pyrimidinyl |
| 6-PhO-2-pyridinyl | 4,6-diMeO-2-pyrimidinyl |
| 6-CF$_3$-2-pyridinyl | 4,6-diMe-2-pyrimidinyl |
| 6-PhO-3-pyridinyl | 6-CF$_3$-4-pyrimidinyl |
| 2-pyrimidinyl |  |
| 4-pyrimidinyl | 4-CF$_3$-2-pyrimidinyl |
| 4-MeO-2-pyrdimidinyl | 6-CF$_3$-2-pyrazinyl |
| 4-Me-2-pyrimidinyl | 5-CF$_3$-3-pyridinyl |
| 6-MeO-4-pyrimidinyl | 3-MeO-2-pyridinyl |
| 2-Ph-4-thiazolyl | 5-CN-2-pyridinyl |
| 3-MeO-6-pyridazinyl | 6-Me-2-pyridinyl |
| 5-Me-2-furanyl | 4-t-Bu-2-nap |
| 2,5-diMe-3-thienyl | 3,5-diBr-Ph |
| 3-OCF$_2$H-Ph | 4-t-Bu-2-pyridinyl |
| 4-OCF$_2$H-Ph | 4-Ph-2-pyridinyl |
| 5-Me-2-nap | 4-Me$_3$Si-2-pyridinyl |
| 6-Me$_3$Si-2-nap | 5-Me$_3$Ge-2-pyridinyl |
| 7-OCF$_3$-2-nap | 4-CF$_3$-2-nap |

TABLE 17

Compounds of Formula I defined as:

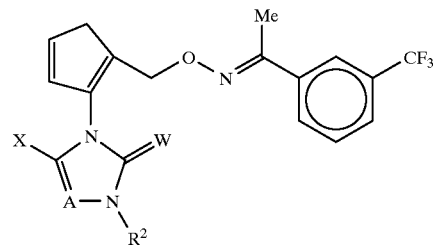

| X | A | X | A |
|---|---|---|---|
| $R^2$ = Me, W = O | | | |
|  |  | MeS | N |
| EtO | N | EtS | N |
| n-PrO | N | n-PrS | N |
| H$_2$C=CHCH$_2$O | N | H$_2$C=CHCH$_2$S | N |
| HC≡CCH$_2$O | N | HC≡CCH$_2$S | N |
| CF$_3$O | N | CF$_3$S | N |
| (c-Pr)O | N | (c-Pr)S | N |
| MeO | CH | MeS | CH |
| EtO | CH | EtS | CH |
| n-PrO | CH | n-PrS | CH |
| H$_2$C=CHCH$_2$O | CH | H$_2$C=CHCH$_2$S | CH |
| HC≡CCH$_2$O | CH | HC≡CCH$_2$S | CH |
| CF$_3$O | CH | CF$_3$S | CH |
| (c-Pr)O | CH | (c-Pr)S | CH |
| $R^2$ = Et, W = O | | | |
| MeO | N | MeS | N |
| EtO | N | EtS | N |
| n-PrO | N | n-PrS | N |
| H$_2$C=CHCH$_2$O | N | H$_2$C=CHCH$_2$S | N |
| HC≡CCH$_2$O | N | HC≡CCH$_2$S | N |
| CF$_3$O | N | CF$_3$S | N |
| (c-Pr)O | N | (c-Pr)S | N |
| MeO | CH | MeS | CH |
| EtO | CH | EtS | CH |
| n-PrO | CH | n-PrS | CH |
| H$_2$C=CHCH$_2$O | CH | H$_2$C=CHCH$_2$S | CH |
| HC≡CCH$_2$O | CH | HC≡CCH$_2$S | CH |
| CF$_3$O | CH | CF$_3$S | CH |
| (c-Pr)O | CH | (c-Pr)S | CH |
| $R^2$ = Me, W = S | | | |
| MeO | N | MeS | N |
| EtO | N | EtS | N |

TABLE 17-continued

Compounds of Formula I defined as:

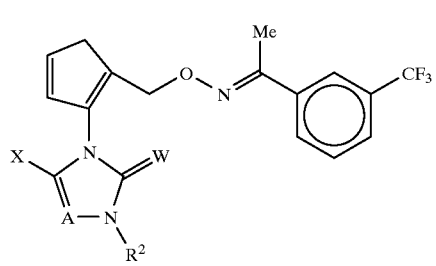

| X | A | X | A |
|---|---|---|---|
| n-PrO | N | n-PrS | N |
| H$_2$C=CHCH$_2$O | N | H$_2$C=CHCH$_2$S | N |
| HC≡CCH$_2$O | N | HC≡CCH$_2$S | N |
| CF$_3$O | N | CF$_3$S | N |
| (c-Pr)O | N | (c-Pr)S | N |
| MeO | CH | MeS | CH |
| EtO | CH | EtS | CH |
| n-PrO | CH | n-PrS | CH |
| H$_2$C=CHCH$_2$O | CH | H$_2$C=CHCH$_2$S | CH |
| HC≡CCH$_2$O | CH | HC≡CCH$_2$S | CH |
| CF$_3$O | CH | CF$_3$S | CH |
| (c-Pr)O | CH | (c-Pr)S | CH |
| $R^2$ = Et, W = S | | | |
| MeO | N | MeS | N |
| EtO | N | EtS | N |
| n-PrO | N | n-PrS | N |
| H$_2$C=CHCH$_2$O | N | H$_2$C=CHCH$_2$S | N |
| HC≡CCH$_2$O | N | HC≡CCH$_2$S | N |
| CF$_3$O | N | CF$_3$S | N |
| (c-Pr)O | N | (c-Pr)S | N |
| MeO | CH | MeS | CH |
| EtO | CH | EtS | CH |
| n-PrO | CH | n-PrS | CH |
| H$_2$C=CHCH$_2$O | CH | H$_2$C=CHCH$_2$S | CH |
| HC≡CCH$_2$O | CH | HC≡CCH$_2$S | CH |
| CF$_3$O | CH | CF$_3$S | CH |
| (c-Pr)O | CH | (c-Pr)S | CH |

TABLE 18

Compounds of Formula I defined as:

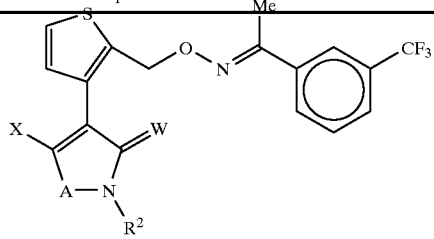

$R^2$ = Me, W = O

| X | A | X | A | X | A | X | A |
|---|---|---|---|---|---|---|---|
|   |   | MeS | O | MeO | S | MeS | S |
| EtO | O | EtS | O | EtO | S | EtS | S |
| n-PrO | O | n-PrS | O | n-PrO | S | n-PrS | S |

TABLE 18-continued

Compounds of Formula I defined as:

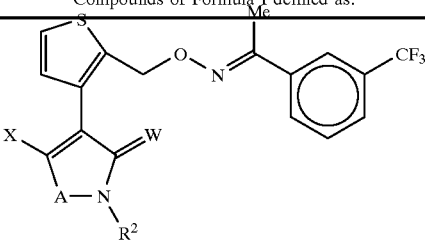

| X | A | X | A | X | A | X | A |
|---|---|---|---|---|---|---|---|
| H₂C=CHCH₂O | O | H₂C=CHCH₂S | O | H₂C=CHCH₂O | S | H₂C=CHCH₂S | S |
| HC≡CCH₂O | O | HC≡-CCH₂S | O | HC≡CCH₂O | S | HC≡CCH₂S | S |
| CF₃O | O | CF₃S | O | CF₃O | S | CF₃S | S |
| (c-Pr)O | O | (c-Pr)S | O | (c-Pr)O | S | (c-Pr)S | S |

$R^2$ = Et, W = O

| X | A | X | A | X | A | X | A |
|---|---|---|---|---|---|---|---|
| MeO | O | MeS | O | MeO | S | MeS | S |
| EtO | O | EtS | O | EtO | S | EtS | S |
| n-PrO | O | n-PrS | O | n-PrO | S | n-PrS | S |
| H₂C=CHCH₂O | O | H₂C=CHCH₂S | O | H₂C=CHCH₂O | S | H₂C=CHCH₂S | S |
| HC≡CCH₂O | O | HC≡CCH₂S | O | HC≡CCH₂O | S | HC≡CCH₂S | S |
| CF₃O | O | CF₃S | O | CF₃O | S | CF₃S | S |
| (c-Pr)O | O | (c-Pr)S | O | (c-Pr)O | S | (c-Pr)S | S |

$R^2$ = Me, W = S

| X | A | X | A | X | A | X | A |
|---|---|---|---|---|---|---|---|
| MeO | O | MeS | O | MeO | S | MeS | S |
| EtO | O | EtS | O | EtO | S | EtS | S |
| n-PrO | O | n-PrS | O | n-PrO | S | n-PrS | S |
| H₂C=CHCH₂O | O | H₂C=CHCH₂S | O | H₂C=CHCH₂O | S | H₂C=CHCH₂S | S |
| HC≡CCH₂O | O | HC≡CCH₂S | O | HC≡CCH₂O | S | HC≡CCH₂S | S |
| CF₃O | O | CF₃S | O | CF₃O | S | CF₃S | S |
| (c-Pr)O | O | (c-Pr)S | O | (c-Pr)O | S | (c-Pr)S | S |

$R^2$ = Et, W = S

| X | A | X | A | X | A | X | A |
|---|---|---|---|---|---|---|---|
| MeO | O | MeS | O | MeO | S | MeS | S |
| EtO | O | EtS | O | EtO | S | EtS | S |
| n-PrO | O | n-PrS | O | n-PrO | S | n-PrS | S |
| H₂C=CHCH₂O | O | H₂C=CHCH₂S | O | H₂C=CHCH₂O | S | H₂C=CHCH₂S | S |
| HC≡CCH₂O | O | HC≡CCH₂S | O | HC≡CCH₂O | S | HC≡C-CH₂S | S |
| CF₃O | O | CF₃S | O | CF₃CF₃O | S | CF₃S | S |
| (c-Pr)O | O | (c-Pr)S | O | (c-Pr)O | S | (c-Pr)S | S |

TABLE 19

Compounds of Formula I defined as:

| $R^9$ | $R^9$ | $R^9$ | $R^9$ |
|---|---|---|---|
| 2-Br—Ph | 2-Me—Ph | 2-Et—Ph | 4-EtO-2-pyrimidinyl |
| 2-CN—Ph | 2-F—Ph | 2-Cl—Ph | 4,6-diMeO-2-pyrimidinyl |
| 2,4-diCl—Ph | 2-Me-4-Cl—Ph | 6-CF₃-2-pyridinyl | 4,6-diMe-2-pyrimidinyl |
| 2-CF₃—Ph | 3,5-diCl—Ph | 2-pyrimidinyl | 6-CF₃-4-pyrimidinyl |
| 2-I—Ph | 3,5-diCF₃—Ph | 4-pyrimidinyl | 4-CF₃-2-pyridinyl |
| 4-NO₂—Ph | 2-MeO—Ph | 4-MeO-2-pyrimidinyl | 4-CF₃-2-pyridinyl |
| 4-CF₃O—Ph | 2,6-diMeO—Ph | 4-Me-2-pyrimidinyl | 5-CF₃-3-pyridinyl |

TABLE 19-continued

Compounds of Formula I defined as:

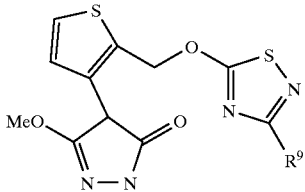

| $R^9$ | $R^9$ | $R^9$ | $R^9$ |
|---|---|---|---|
| 4-Me—Ph | 3-CF$_3$O—Ph | 6-MeO-4-pyrimidinyl | 3-MeO-2-pyridinyl |
| 4-Cl—Ph | 4-Br—Ph | 5-Me-2-furanyl | 5-CN-2-pyridinyl |
| 3-Me—Ph | 3-Et—Ph | 2,5-diMe-3-thienyl | 6-Me-2-pyridinyl |
| 3-CF$_3$—Ph | 4-MeO—Ph | 3-OCF$_2$H—Ph | 3,5-diBr—Ph |
| 3-Cl-2-Me—Ph | 4-t-Bu—Ph | 4-OCF$_2$H—Ph | 4-t-Bu-2-pyridinyl |
| 3-t-Bu—Ph | 4-CN—Ph | 3-Me$_3$Si—Ph | 4-Me$_3$Si-2-pyridinyl |
| 3-F—Ph | 4-NO$_2$—Ph | 4-Me$_3$Si—Ph | 4-Me$_3$Ge-2-pyridinyl |
| 4-CF$_3$—Ph | 3,4-diMe—Ph | 3-Me$_3$Ge—Ph | 4,6-diCF$_3$-2-pyrimidinyl |
| 3,4-diCl—Ph | 3,5-diMe—Ph | 4-Me$_3$Ge—Ph | 5-CF$_3$-2-furanyl |
| 3,4-diCF$_3$—Ph | 4-F-3-CF$_3$—Ph | 3-EtO—Ph | 5-CF$_3$-2-thienyl |
| 4-F—Ph | 5-F-3-CF$_3$—Ph | Ph | (2-CN—Ph)CH$_2$ |
| 3,4-diF—Ph | 3-Br-4-MeO—Ph | 4,5-diBr-2-thienyl | (2-CF$_3$—Ph)CH$_2$ |
| 3-Cl-4-Me—Ph | 5-F-2-thienyl | 4,5-diCl-2-thienyl | (3-CF$_3$—Ph)CH$_2$ |
| 3,5-diF—Ph | 5-Br-2-thienyl | 4,5-diF-2-thienyl | (4-CF$_3$—Ph)CH$_2$ |
| 3-F-4-Cl—Ph | 5-Cl-2-thienyl | 2-CF$_3$CH$_2$O-5-pyridinyl | (3,5-diCF$_3$—Ph)CH$_2$ |
| 3-MeO—Ph | 2,5-diF-3-thienyl | (4-Cl—Ph)CH$_2$ | (2-CF$_3$O—Ph)CH$_2$ |
| 3-Cl—Ph | 2,5-diCl-3-thienyl | (3-Cl—Ph)CH$_2$ | (3-CF$_3$O—Ph)CH$_2$ |
| t-Bu | 2,5-diBr-3-thienyl | (2-Cl—Ph)CH$_2$ | (4-CF$_3$O—Ph)CH$_2$ |
| 3-Br—Ph | 2-I—Ph | (2-Br—Ph)CH$_2$ | 2,6-diCl-4-pyridinyl |
| 4-Ph—Ph | 3-I—Ph | (3-Br—Ph)CH$_2$ | (2,6-diCl—Ph)CH$_2$ |
| 4-Br-3-Me—Ph | 2-Br-5-pyridinyl | (4-Br—Ph)CH$_2$ | |

TABLE 20

Compounds of Formula I defined as:

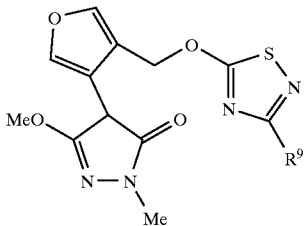

| $R^9$ | $R^9$ | $R^9$ | $R^9$ |
|---|---|---|---|
| 2-Br—Ph | 2-Me—Ph | 2-Et—Ph | 4-EtO-2-pyrimidinyl |
| 2-CN—Ph | 2-F—Ph | 2-Cl—Ph | 4,6-diMeO-2-pyrimidinyl |
| 2,4-diCl—Ph | 2-Me-4-Cl—Ph | 6-CF$_3$-2-pyridinyl | 4,6-diMe-2-pyrimidinyl |
| 2-CF$_3$—Ph | 3,5-diCl—Ph | 2-pyrimidinyl | 6-CF$_3$-4-pyrimidinyl |
| 2-I—Ph | 3,5-diCF$_3$—Ph | 4-pyrimidinyl | 4-CF$_3$-2-pyridinyl |
| 4-NO$_2$—Ph | 2-MeO—Ph | 4-MeO-2-pyrimidinyl | 4-CF$_3$-2-pyrimidinyl |
| 4-CF$_3$O—Ph | 2,6-diMeO—Ph | 4-Me-2-pyrimidinyl | 5-CF$_3$-3-pyridinyl |
| 4-Me—Ph | 3-CF$_3$O—Ph | 6-MeO-4-pyrimidinyl | 3-MeO-2-pyridinyl |
| 4-Cl—Ph | 4-Br—Ph | 5-Me-2-furanyl | 5-CN-2-pyridinyl |
| 3-Me—Ph | 3-Et—Ph | 2,5-diMe-3-thienyl | 6-Me-2-pyridinyl |
| 3-CF$_3$—Ph | 4-MeO—Ph | 3-OCF$_2$H—Ph | 3,5-diBr—Ph |
| 3-Cl-2-Me—Ph | 4-t-Bu—Ph | 4-OCF$_2$H—Ph | 4-t-Bu-2-pyridinyl |
| 3-t-Bu—Ph | 4-CN—Ph | 3-Me$_3$Si—Ph | 4-Me$_3$Si-2-pyridinyl |
| 3-F—Ph | 4-NO$_2$—Ph | 4-Me$_3$Si—Ph | 4-Me$_3$Ge-2-pyridinyl |
| 4-CF$_3$—Ph | 3,4-diMe—Ph | 3-Me$_3$Ge—Ph | 4,6-diCF$_3$-2-pyrimidinyl |
| 3,4-diCl—Ph | 3,5-diMe—Ph | 4-Me$_3$Ge—Ph | 5-CF$_3$-2-furanyl |
| 3,4-diCF$_3$—Ph | 4-F-3-CF$_3$—Ph | 3-EtO—Ph | 5-CF$_3$-2-thienyl |
| 4-F—Ph | 5-F-3-CF$_3$—Ph | Ph | (2-CN—Ph)CH$_2$ |
| 3,4-diF—Ph | 3-Br-4-MeO—Ph | 4,5-diBr-2-thienyl | (2-CF$_3$—Ph)CH$_2$ |
| 3-Cl-4-Me—Ph | 5-F-2-thienyl | 4,5-diCl-2-thienyl | (3-CF$_3$—Ph)CH$_2$ |
| 3,5-diF—Ph | 5-Br-2-thienyl | 4,5-diF-2-thienyl | (4-CF$_3$—Ph)CH$_2$ |

TABLE 20-continued

Compounds of Formula I defined as:

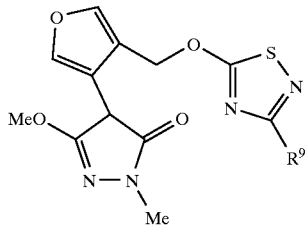

| $R^9$ | $R^9$ | $R^9$ | $R^9$ |
| --- | --- | --- | --- |
| 3-F-4-Cl—Ph | 5-Cl-2-thienyl | 2-CF$_3$CH$_2$O-5-pyridinyl | (3,5-diCF$_3$—Ph)CH$_2$ |
| 3-MeO—Ph | 2,5-diF-3-thienyl | (4-Cl—Ph)CH$_2$ | (2-CF$_3$O—Ph)CH$_2$ |
| 3-Cl—Ph | 2,5-diCl-3-thienyl | (3-Cl—Ph)CH$_2$ | (3-CF$_3$O—Ph)CH$_2$ |
| t-Bu | 2,5-diBr-3-thienyl | (2-Cl—Ph)CH$_2$ | (4-CF$_3$O—Ph)CH$_2$ |
| 3-Br—Ph | 2-I—Ph | (2-Br—Ph)CH$_2$ | 2,6-diCl-4-pyridinyl |
| 4-Ph—Ph | 3-I—Ph | (3-Br—Ph)CH$_2$ | (2,6-diCl—Ph)CH$_2$ |
| 4-Br-3-Me—Ph | 2-Br-5-pyridinyl | (4-Br—Ph)CH$_2$ | |

TABLE 21

Compounds of Formula I defined as:

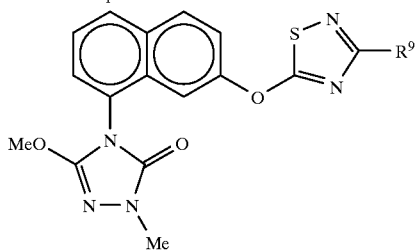

| $R^9$ | $R^9$ | $R^9$ | $R^9$ |
| --- | --- | --- | --- |
| 2-Br—Ph | 2-Me—Ph | 2-Et—Ph | 4-EtO-2-pyrimidinyl |
| 2-CN—Ph | 2-F—Ph | 2-Cl—Ph | 4,6-diMeO-2-pyrimidinyl |
| 2,4-diCl—Ph | 2-Me-4-Cl—Ph | 6-CF$_3$-2-pyridinyl | 4,6-diMe-2-pyrimidinyl |
| 2-CF$_3$—Ph | 3,5-diCl—Ph | 2-pyrimidinyl | 6-CF$_3$-4-pyrimidinyl |
| 2-I—Ph | 3,5-diCF$_3$—Ph | 4-pyrimidinyl | 4-CF$_3$-2-pyridinyl |
| 4-NO$_2$—Ph | 2-MeO—Ph | 4-MeO-2-pyrimidinyl | 4-CF$_3$-2-pyrimidinyl |
| 4-CF$_3$O—Ph | 2,6-diMeO—Ph | 4-Me-2-pyrimidinyl | 5-CF$_3$-3-pyridinyl |
| 4-Me—Ph | 3-CF$_3$O—Ph | 6-MeO-4-pyrimidinyl | 3-MeO-2-pyridinyl |
| 4-Cl—Ph | 4-Br—Ph | 5-Me-2-furanyl | 5-CN-2-pyridinyl |
| 3-Me—Ph | 3-Et—Ph | 2,5-diMe-3-thienyl | 6-Me-2-pyridinyl |
| 3-CF$_3$—Ph | 4-MeO—Ph | 3-OCF$_2$H—Ph | 3,5-diBr—Ph |
| 3-Cl-2-Me—Ph | 4-t-Bu—Ph | 4-OCF$_2$H—Ph | 4-t-Bu-2-pyridinyl |
| 3-t-Bu—Ph | 4-CN—Ph | 3-Me$_3$Si—Ph | 4-Me$_3$Si-2-pyridinyl |
| 3-F—Ph | 4-NO$_2$—Ph | 4-Me$_3$Si—Ph | 4-Me$_3$Ge-2-pyridinyl |
| 4-CF$_3$—Ph | 3,4-diMe—Ph | 3-Me$_3$Ge—Ph | 4,6-diCF$_3$-2-pyrimidinyl |
| 3,4-diCl—Ph | 3,5-diMe—Ph | 4-Me$_3$Ge—Ph | 5-CF$_3$-2-furanyl |
| 3,4-diCF$_3$—Ph | 4-F-3-CF$_3$—Ph | 3-EtO—Ph | 5-CF$_3$-2-thienyl |
| 4-F—Ph | 5-F-3-CF$_3$—Ph | Ph | (2-CN—Ph)CH$_2$ |
| 3,4-diF—Ph | 3-Br-4-MeO—Ph | 4,5-diBr-2-thienyl | (2-CF$_3$—Ph)CH$_2$ |
| 3-Cl-4-Me-Ph | 5-F-2-thienyl | 4,5-diCl-2-thienyl | (3-CF$_3$—Ph)CH$_2$ |
| 3,5-diF-Ph | 5-Br-2-thienyl | 4,5-diF-2-thienyl | (4-CF$_3$—Ph)CH$_2$ |
| 3-F-4-Cl—Ph | 5-Cl-2-thienyl | 2-CF$_3$CH$_2$O-5-pyridinyl | (3,5-diCF$_3$—Ph)CH$_2$ |
| 3-MeO—Ph | 2,5-diF-3-thienyl | (4-Cl—Ph)CH$_2$ | (2-CF$_3$O—Ph)CH$_2$ |
| 3-Cl—Ph | 2,5-diCl-3-thienyl | (3-Cl—Ph)CH$_2$ | (3-CF$_3$O—Ph)CH$_2$ |
| t-Bu | 2,5-diBr-3-thienyl | (2-Cl—Ph)CH$_2$ | (4-CF$_3$O—Ph)CH$_2$ |
| 3-Br—Ph | 2-I—Ph | (2-Br—Ph)CH$_2$ | 2,6-diCl-4-pyridinyl |
| 4-Ph—Ph | 3-I—Ph | (3-Br—Ph)CH$_2$ | (2,6-diCl—Ph)CH$_2$ |
| 4-Br-3-Me—Ph | 2-Br-5-pyridinyl | (4-Br—Ph)CH$_2$ | |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–G.

Example A

| Wettable Powder | |
| --- | --- |
| Compound 17 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
| --- | --- |
| Compound 17 | 10.0% |
| attapulgite granules (low volatile matter, 0.71/0.30 mm; U.S.S. No. 25–50 sieves) | 90.0%. |

Example C

| Extruded Pellet | |
| --- | --- |
| Compound 17 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
| --- | --- |
| Compound 17 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof to be protected, or to the plant seed or seedling to be protected, an effective amount of a compound of the invention or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Septoria tritici, Cercosporidium personatum, Cercospora arachidicola, Pseudocercosporella herpotrichoides, Cercospora beticola, Botrytis cinerea, Moniliniafructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerothecafuliginea, Fusarium oxysporum, Verticillium dahliae, Pythium aphanidermatum, Phytophthora megasperma, Sclerotinia scierotiorum, Sclerotium rolfsii, Erysiphe polygoni, Pyrenophora teres, Gaeumannomyces graminis, Rynchosporium secalis, Fusarium roseum, Bremia lactucae* and other generea and species closely related to these pathogens.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamnectin, acephate, azinphos-methyl, bifenthrin, buprofezin, carbofuran, chlorpyrifos, chlorpyrifos-methyl, cyfluthrin, beta-cyfluthrin, deltamnethrin, diafenthiuron, diazinon, diflubenzuron, dimethoate, esfenvalerate, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phospharnidon, pirimicarb, profenofos, rotenone, sulprofos, tebufenozide, tefluthrin, terbufos, tetrachlorvinphos, thiodicarb, tralomethrin, trichlorfon and triflumuron; fungicides such as azoxystrobin (ICIA5504), benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxyconazole (BAS 480F), fenarimol, fenbuconazole, fenpiclonil, fenpropidin, fenpropimorph, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl (BAS 490F), mancozeb, maneb, mepronil, metalaxyl, metconazole, myclobutanil, neo-asozin (ferric methanearsonate), oxadixyl, penconazole, pencycuron, probenazole, prochloraz, propiconazole, pyrifenox, pyroquilon, sulfur, tebuconazole, tetraconazole, thiabendazole, thiophanate-methyl, thiram, triadimefon, triadimenol, tricyclazole, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

In certain instances, combinations with other fungicides having a similar spectrum of control but a different mode of action will be particularly advantageous for resistance management.

Preferred for better control of plant diseases caused by fungal plant pathogens (e.g., lower use rate or broader spectrum of plant pathogens controlled) or resistance management are mixtures of a compound of this invention with a fungicide selected from the group cyproconazole, cyprodinil (CGA 219417), epoxyconazole (BAS 480F), fenpropidin, fenpropimorph, flusilazole and tebuconazole. Specifically preferred mixtures (compound numbers refer to compounds in Index Tables A–G) are selected from the group: compound 1 and cyproconazole; compound 1 and cyprodinil (CGA 219417); compound 1 and epoxyconazole (BAS 480F); compound 1 and fenpropidin; compound 1 and fenpropimorph; compound 1 and flusilazole; compound 1 and tebuconazole; compound 2 and cyproconazole; compound 2 and cyprodinil (CGA 219417); compound 2 and epoxyconazole (BAS 480F); compound 2 and fenpropidin; compound 2 and fenpropimorph; compound 2 and flusilazole; compound 2 and tebuconazole; compound 4 and cyproconazole; compound 4 and cyprodinil (CGA 219417); compound 4 and epoxyconazole (BAS 480F); compound 4 and fenpropidin; compound 4 and fenpropimorph; compound 4 and flusilazole; compound 4 and tebuconazole; compound 6 and cyproconazole; compound 6 and cyprodinil (CGA 219417); compound 6 and epoxyconazole (BAS 480F); compound 6 and fenpropidin; compound 6 and fenpropimorph; compound 6 and flusilazole; compound 6 and tebuconazole; compound 15 and cyproconazole; compound 15 and cyprodinil (CGA 219417); compound 15 and epoxyconazole (BAS 480F); compound 15 and fenpropidin; compound 15 and fenpropimorph; compound 15 and flusilazole; compound 15 and tebuconazole; compound 17 and cyproconazole; compound 17 and cyprodinil (CGA 219417); compound 17 and epoxyconazole (BAS 480F); compound 17 and fenpropidin; compound 17 and fenpropimorph; compound 17 and flusilazole; and compound 15 and tebuconazole.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–G for compound descriptions. The following abbreviations are used in the Index Tables which follow: Ph=phenyl and PhO=phenoxy. The abbreviation "Ex." stands for "Example" and is followed by a number indicating in which example the compound is prepared.

INDEX TABLE A

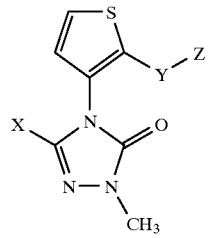

| Cmpd No. | X | Y | Z | m.p. (° C.) |
|---|---|---|---|---|
| 1 Ex. 2 | $CH_3O$ | —$CH_2O$—N=C($CH_3$)— | 3-($CH_3$)$_3$Si—Ph | oil/gum* |
| 2 Ex. 3 | $CH_3O$ | —$CH_2O$— | 2,5-di$CH_3$—Ph | 151–153 |
| 3 Ex. 1 | $CH_3O$ | direct bond | $CH_2Br$ | 117–118 |
| 4 | $CH_3O$ | —$CH_2O$—N=C($CH_3$)— | 3-$CF_3$—Ph | 91–93 |
| 5[a] Ex. 4 | $CH_3O$ | —CH=C(Cl)-C(=O)—O— | t-Bu | 105–115 |
| 6[b] Ex. 4 | $CH_3O$ | —CH=C(Cl)-C(=O)—O— | t-Bu | 104 |
| 7 | $CH_3O$ | —$CH_2O$—N=C($CH_3$)— | 4-$CF_3$-pyridin-2-yl | 101–103.5 |
| 8 | $CH_3O$ | direct bond | 3-(3-$CF_3$—Ph)-1,2,4-oxadiazol-5-yl | 158 |
| 9 | $CH_3O$ | —$CH_2O$—N=C($CH_3$)— | 3,4-diCl—Ph | 132–134 |
| 10 | $CH_3O$ | —$CH_2O$—N=C($NH_2$)— | 3-$CF_3$—Ph | 123–124 |
| 11 | $CH_3O$ | —$CH_2O$—N=C($CH_3$)— | 3,5-diBr—Ph | 150.5–151 |
| 12 | $CH_3O$ | —$CH_2O$—N=C($CH_3$)— | 3,5-diCl—Ph | 159–160 |
| 13 | $CH_3O$ | —$CH_2O$—N=C($CH_3$)— | 2-naphthalenyl | 124–125 |
| 14[c] | $CH_3O$ | —$CH_2O$—N=C($CH_2CH_3$)— | 3-$CF_3$—Ph | oil* |
| 15 | $CH_3O$ | —$CH_2O$— | 3-(4-Cl—Ph)-1,2,4-thiadiazol-5-yl | 184–185 |
| 16 | $CH_3O$ | —$CH_2O$— | 3-(3,5-diCl—Ph)-1,2,4-thiadiazol-5-yl | 185–186 |
| 17 Ex. 10 | $CH_3O$ | —$CH_2O$— | 3-(4-$CF_3$—Ph)-1,2,4-thiadiazol-5-yl | 138–139 |

*See Index Table G for $^1$H NMR data.
[a]Compound isolated in a 7:3 ratio of Z and E isomers, respectively.
[b]Compound isolated in a 5:1 ratio of Z and E isomers, respectively.
[c]Compound contains 28% by weight of 2,4-dihydro-5-methoxy-2-methyl-4-[5-methyl-2-[[[[1-[3-(trifluoromethyl)phenyl]ethylene]amino]oxy]methyl]-3-thienyl]-3H-1,2,4-triazol-3-one which is also a compound of this invention.

INDEX TABLE B

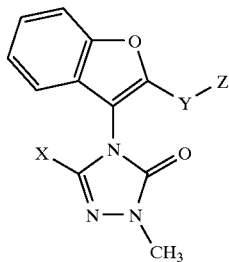

| Cmpd No. | X | Y | Z | m.p. (° C.) |
|---|---|---|---|---|
| 18 | CH$_3$O | direct bond | CH$_2$Br | 132–133 |
| 19 | CH$_3$O | —CH$_2$O—N=C(CH$_3$)— | 3,4-diCl—Ph | 143–144 |
| 20 | CH$_3$O | —CH$_2$O—N=C(CH$_3$)— | 3-(CH$_3$)$_3$Si—Ph | oil* |
| 21 | CH$_3$O | —CH$_2$O—N=C(CH$_3$)— | 4-CF$_3$-pyridin-2-yl | 123–125 |
| 22 | CH$_3$O | —CH$_2$O—N=C(CH$_3$)— | 3-CF$_3$—Ph | 87–89 |

*See Index Table G for $^1$H NMR data.

INDEX TABLE C

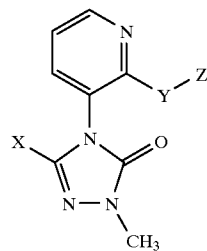

| Cmpd No. | X | Y | Z | m.p. (° C.) |
|---|---|---|---|---|
| 23 | Cl | direct bond | CH$_3$ | 99–101 |
| 24 | CH$_3$O | direct bond | CH$_3$ | 123–125 |
| 25 | CH$_3$O | —CH$_2$O—N=C(CH$_3$)— | 3-CF$_3$—Ph | oil* |
| 26 | CH$_3$O | —CH$_2$O—N=C(CH$_3$)— | 4-CF$_3$-pyridin-2-yl | 106–107 |
| 27 | CH$_3$O | —CH$_2$O—N=C(CH$_3$)— | 3,4-diCl—Ph | 102–104 |
| 28 | CH$_3$O | —CH$_2$O—N=C(CH$_3$)— | 3-(CH$_3$)$_3$Si—Ph | 135–137 |
| 29 | CH$_3$O | —CH$_2$O—N=C(CH$_3$)— | 3,5-diCl—Ph | 135–137 |
| 30 | CH$_3$O | —CH$_2$O—N=C(CH$_3$)— | 3,5-diBr—Ph | 145–147 |
| 31 | CH$_3$O | —CH$_2$O—N=C(NH$_2$)— | 3-CF$_3$—Ph | 147–148 |
| 32 | CH$_3$O | —CH$_2$S— | 5-CF$_3$-4H-1,2,4-triazol-3-yl | 178–179 |
| 33 | CH$_3$O | direct bond | 3-(3-CF$_3$—Ph)-1,2,4-oxadiazol-5-yl | 165–166 |
| 34 | CH$_3$O | —CH$_2$— | 3-CF$_3$-1H-pyrazol-1-yl | 99–100 |
| 35 | CH$_3$O | —CH$_2$O— | 2-Cl-5-CF$_3$—Ph | 106–108 |
| 36 | CH$_3$O | —CH$_2$O— | 2,5-diCH$_3$—Ph | 91–93 |
| 37 | CH$_3$O | —CH$_2$O—N=C(CH$_3$)— | 2-naphthalenyl | semisolid* |
| 38 Ex. 9 | CH$_3$O | —O— | 3-PhO—Ph | 113–114 |
| 39 Ex. 8 | Cl | —O— | 3-PhO—Ph | 72–75 |

*See Index Table G for $^1$H NMR data.

INDEX TABLE D

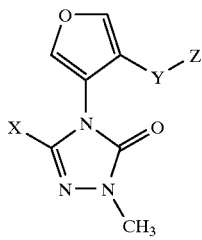

| Cmpd No. | X | Y | Z | m.p. (° C.) |
|---|---|---|---|---|
| 40 | CH$_3$O | direct bond | 3-(3-CF$_3$—Ph)-1,2,4-oxadiazol-5-yl | 149–150 |
| 41 Ex. 5 | CH$_3$O | direct bond | CH$_2$Br | 147–149 |
| 42 | CH$_3$O | —CH$_2$O—N=C(CH$_3$)— | 2-naphthalenyl | 134–136 |
| 43 | CH$_3$O | —CH$_2$O—N=C(CH$_3$)— | 3,4-diCl—Ph | 118–119 |
| 44 | CH$_3$O | —CH$_2$O—N=C(CH$_3$)— | 4-CF$_3$-pyridin-2-yl | 125–127 |
| 45 | CH$_3$O | —CH$_2$O—N=C(CH$_3$)— | 3,5-diCl—Ph | 148.5–150.5 |
| 46 Ex. 6 | CH$_3$O | —CH$_2$O—N=C(CH$_3$)— | 3-(CH$_3$)$_3$Si—Ph | oil* |
| 47 | CH$_3$O | —CH$_2$O—N=C(NH$_2$)— | 3-CF$_3$—Ph | semisolid* |
| 48 | CH$_3$O | —CH$_2$O—N=C(CH$_3$)— | 3-CF$_3$—Ph | 81–83 |
| 49 | CH$_3$O | —CH$_2$O—N=C(CH$_3$)— | 3,5-diBr—Ph | 126.5–127.5 |

*See Index Table G for $^1$H NMR data.

INDEX TABLE E

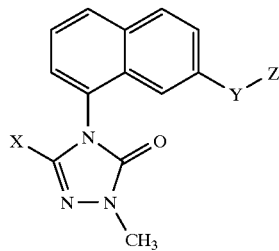

| Cmpd No. | X | Y | Z | m.p. (° C.) |
|---|---|---|---|---|
| 50 Ex. 7 | CH$_3$O | —O— | 3-(4-CF$_3$—Ph)-1,2,4-thiadiazol-5-yl | 216–217 |
| 51 | CH$_3$O | —O— | 3-(3,5-diCl—Ph)-1,2,4-thiadiazol-5-yl | 222–223 |
| 52 | CH$_3$O | —O— | 3-(4-Cl—Ph)-1,2,4-thiadiazol-5-yl | 226–227 |

INDEX TABLE F

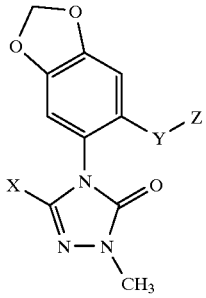

| Cmpd No. | X | Y | Z | m.p. (° C.) |
|---|---|---|---|---|
| 53 | CH$_3$O | —CH$_2$O—N=C(CH$_3$)— | 3-CF$_3$—Ph | 153–155 |

INDEX TABLE G

| Cmpd No. | $^1$H NMR Data (CDCl$_3$ solution unless indicated otherwise)$^a$ |
|---|---|
| 1 | δ 7.76 (s, 1H), 7.60 (m, 1H), 7.54 (m, 1H), 7.36 (d, 1H), 7.32 (d, 1H), 6.94 (d, 1H), 5.29 (s, 2H), 3.89 (s, 3H), 3.41 (s, 3H), 2.21 (s, 3H) 0.28 (s, 9H). |
| 14 | major component: δ 7.33 (d, 1H), 6.95 (d, 1H), 5.31 (d, 2H), 3.904 (s, 3H), 3.42 (s, 3H), 2.74 (q, 2H), 1.11 (t, 3H) plus peaks overlapping with minor component at 7.88 (d), 7.79 (m), 7.61 (d), 7.49 (t); minor component: δ 6.62 (s, 1H), 5.22 (d, 2H), 3.899 (s, 3H), 3.41 (s, 3H), 2.45 (s, 3H), 2.22 (d, 3H) plus peaks overlapping with major component at 7.88 (d), 7.79 (m), 7.61 (d), 7.49 (t). |
| 20 | δ 7.67 (s, 1H), 7.52 (m, 3H), 7.40 (d, 1H), 7.33 (m, 2H), 7.26 (m, 1H), 5.35 (br s, 2H), 3.77 (s, 3H), 3.44 (s, 3H), 2.20 (s, 3H), 0.27 (s, 9H). |
| 25 | δ 8.68 (m, 1H), 7.80 (s, 1H), 7.75 (d, 1H), 7.60 (m, 2H), 7.47–7.37 (m, 2H), 5.47 (AB pattern, 2H), 3.82 (s, 3H), 3.35 (s, 3H), 2.16 (s, 3H). |
| 37 | δ 8.69 (m, 1H), 7.94 (s, 1H), 7.85–7.73 (m, 4H), 7.61 (d, 1H), 7.59–7.45 (m, 2H), 7.38 (dd, 1H), 5.50 (AB pattern, 2H), 3.78 (s, 3H); 3.35 (s, 3H), 2.25 (s, 3H). |
| 46 | δ 7.70 (s, 1H), 7.54 (m, 4H), 7.34 (t, 1H), 5.11 (s, 2H), 3.86 (s, 3H), 3.32 (s, 3H), 2.14 (s, 3H), 0.28 (s, 9H). |
| 47 | δ 7.86 (s, 1H), 7.76 (d, 1H), 7.64 (d, 1H), 7.59 (d, 1H), 7.54 (d, 1H), 7.53–7.47 (m, 1H), 5.01 (br s, 2H), 4.96 (s, 2H), 3.89 (s, 3H), 3.33 (s, 3H). |

$^a$$^1$H NMR data are in ppm downfield from tetramethylsilane. Couplings are designated by (s)-singlet, (d)-doublet, (t)-triplet, (q)-quartet, (m)-multiplet, (dd)-doublet of doublets, (br s)-broad singlet.

BIOLOGICAL EXAMPLES OF THE INVENTION

The compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests. Spraying these 200 ppm test suspensions to the point of run-off on the test plants is the equivalent of a rate of 500 g/ha

Test A

The test suspension was sprayed to the point of run-off on wheat seedlings. The following way the seedlings were inoculated with a spore dust of *Erysiphe graminis* f. sp. *tritici*, (the causal agent of wheat powdery mildew) and incubated in a growth chamber at 20° C. for 7 days, after which disease ratings were made.

Test B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

Test C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

Test D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

Test E

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days, and then incubated in a saturated atmosphere at 20° C. for 24 h, after which disease ratings were made.

Test F

The test suspension was sprayed to the point of run-off on cucumber seedlings. The following day the seedlings were inoculated with a spore suspension of *Botrytis cinerea* (the causal agent of gray mold on many crops) and incubated in a saturated atmosphere at 20° C. for 48 h, and moved to a growth chamber at 20° C. for 5 days, after which disease ratings were made.

Results for Tests A–F are given in Table A. In the table, a rating of 100 indicates 100% disease control and a rating of 0 indicates no disease control (relative to the controls). A dash (–) indicates no test results.

TABLE A

| Cmpd No. | Test A | Test B | Test C | Test D | Test E | Test F |
|---|---|---|---|---|---|---|
| 1 | 100 | 100 | 94 | 0 | 16* | 41 |
| 2 | 100 | 93 | 0 | 24 | 0* | 41 |
| 3 | 46 | 0 | 0 | 0 | 13* | 0 |
| 4 | 100 | 100 | 97 | 0 | 17* | 66 |
| 5 | 97 | 100 | 0 | — | 0* | 0 |
| 6 | 97 | 100 | 52 | 0 | 17* | 41 |
| 7 | 97 | 100 | 86 | 0 | 8* | 42 |
| 8 | 99 | 97 | 74 | 10 | 21* | 0 |
| 9 | 91 | 99 | 53 | 86 | 49* | 0 |
| 10 | 82 | 97 | 32 | 72 | 6** | 0 |
| 11 | 100 | 99 | 53 | 91 | 100** | 82 |

TABLE A-continued

| Cmpd No. | Test A | Test B | Test C | Test D | Test E | Test F |
|---|---|---|---|---|---|---|
| 12 | 100 | 100 | 53 | 39 | 95* | 43 |
| 13 | 100 | 100 | 91 | 73 | 88* | 67 |
| 14 | 100 | 100 | 85 | 56 | 28* | 82 |
| 15 | 94 | 99 | 26 | 0 | 42* | 82 |
| 16 | 99 | 97 | 26 | 0 | 40* | 90 |
| 17 | 98 | 99 | 90 | 0 | 48* | 69 |
| 18 | 53 | 61 | 0 | 0 | 30* | 0 |
| 19 | 91 | 0 | 0 | 22 | 0* | 0 |
| 20 | 59 | 84 | 0 | 0 | 8* | 0 |
| 21 | 31 | 93 | 0 | 0 | 29* | 0 |
| 22 | 91 | 66 | 0 | 0 | 0* | 0 |
| 23 | 0 | 0 | 0 | 0 | 3* | 0 |
| 24 | 0 | 0 | 0 | 0 | 3* | 0 |
| 25 | 98 | 97 | 0 | 0 | 22* | 46 |
| 26 | 99 | 100 | 0 | 0 | 2* | 10 |
| 27 | 76 | 99 | 0 | 0 | 2* | 0 |
| 28 | 100 | 100 | 32 | 0 | 14* | 90 |
| 29 | 100 | 100 | 53 | 0 | 23* | 48 |
| 30 | 99 | 99 | 53 | 0 | 7* | 70 |
| 31 | 60 | 0 | 0 | 0 | 7* | 68 |
| 32 | 0 | 0 | 0 | 0 | 7* | 44 |
| 33 | 97 | 85 | 0 | 46 | 6* | 0 |
| 34 | 0 | 66 | 0 | 25 | 13* | 57 |
| 35 | 36 | 66 | 0 | 11 | 7* | 0 |
| 36 | 84 | 85 | 0 | 25 | 9* | 0 |
| 37 | 25 | 93 | 53 | 25 | 0* | 0 |
| 38 | 91 | 99 | 60 | 95 | 71* | 77 |
| 39 | 61 | 86 | 74 | 0 | — | 0 |
| 40 | 61 | 85 | 0 | 26 | 2* | 44 |
| 41 | 0 | 65 | 0 | 0 | — | 0 |
| 42 | 55 | 100 | 53 | 25 | 1* | 5 |
| 43 | 100 | 99 | 32 | — | 11* | 68 |
| 44 | 100 | 100 | 32 | 10 | 1* | 94 |
| 45 | 100 | 99 | 53 | 72 | 1* | 94 |
| 46 | 99 | 100 | 32 | 24 | 19* | 46 |
| 47 | 0 | 0 | 0 | 0 | 37* | 0 |
| 48 | 98 | 99 | 32 | 26 | 15* | 41 |
| 49 | 99 | 94 | 53 | 72 | 12* | 7 |
| 50 | 94 | 67 | 0 | 63 | 5* | 94 |
| 51 | 85 | 0 | 0 | 16 | — | 0 |
| 52 | 85 | 26 | 0 | 42 | — | 0 |
| 53 | 57 | 86 | 0 | 0 | 5* | 0 |

*Compound was tested at 10 ppm (equivalent to 25 g/ha).
**Compound was tested at 40 ppm (equivalent to 100 g/ha).

What is claimed is:

1. A compound selected from Formula I, N-oxides and agriculturally suitable salts thereof,

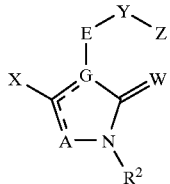

I wherein:
E is a ring system selected from
  i) 5 to 12-membered monocyclic and fused bicyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, and each fused bicyclic ring system does or does not contain one nonaromatic ring that does or does not include one or two Q as ring members and does or does not include one or two ring members independently selected from $C(=O)$ and $S(O)_2$, provided that G is attached to an aromatic ring, and when G and Y are attached to the same ring, then G and Y are attached to adjacent ring members, each aromatic heterocyclic ring system unsubstituted or substituted with one of $R^3$, $R^4$, or both $R^3$ and $R^4$;

A is O; S; N; $NR^5$; or $CR^{14}$;

G is C or N; provided that when G is C, then A is O, S or $NR^5$ and the floating double bond is attached to G; and when G is N, then A is N or $CR^{14}$ and the floating double bond is attached to A;

W is O; S; NH; $N(C_1-C_6$ alkyl); or $NO(C_1-C_6$ alkyl);

X is $OR^1$; $S(O)_mR^1$; or halogen;

$R^1$ is $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl;

$R^2$ is H; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; $C_2-C_4$ alkoxycarbonyl; hydroxy; $C_1-C_2$ alkoxy; or acetyloxy;

$R^3$ and $R^4$ are each independently halogen; cyano; nitro; hydroxy; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_1-C_6$ alkoxy; $C_1-C_6$ haloalkoxy; $C_2-C_6$ alkenyloxy; $C_2-C_6$ alkynyloxy; $C_1-C_6$ alkylthio; $C_1-C_6$ alkylsulfinyl; $C_1-C_6$ alkylsulfonyl; formyl; $C_2-C_6$ alkylcarbonyl; $C_2-C_6$ alkoxycarbonyl; $NH_2C(O)$; $(C_1-C_4$ alkyl)$NHC(O)$; $(C_1-C_4$ alkyl)$_2NC(O)$; $Si(R^{25})_3$; $Ge(R^{25})_3$; $(R^{25})_3Si-C\equiv C-$; or phenyl, phenylethynyl, benzoyl, or phenylsulfonyl each substituted with $R^8$ and unsubstituted or substituted with one or more $R^{10}$;

$R^5$ is H; $C_1-C_6$ alkyl; $C_1-C_6$ haloalkyl; $C_2-C_6$ alkenyl; $C_2-C_6$ haloalkenyl; $C_2-C_6$ alkynyl; $C_2-C_6$ haloalkynyl; $C_3-C_6$ cycloalkyl; $C_2-C_4$ alkylcarbonyl; or $C_2-C_4$ alkoxycarbonyl;

Y is $-O-$; $-S(O)_n-$; $-NR^{15}-$; $-C(=O)-$; $-CH(OR^{15})-$; $-CHR^6-$; $-CHR^6CHR^6-$; $-CR^6=CR^6-$; $-C\equiv C-$; $-CHR^{15}O-$; $-OCHR^{15}-$; $-CHR^{15}S(O)_n-$; $-S(O)_nCHR^{15}-$; $-CHR^{15}O-N=C(R^7)-$; $-(R^7)C=N-OCH(R^{15})-$; $-C(R^7)=N-O-$; $-O-N=C(R^7)-$; $-CHR^{15}OC(=O)N(R^{15})-$; $-CHR^{15}OC(=S)N(R^{15})-$; $-CHR^{15}OC(=O)O-$; $-CHR^{15}OC(=S)O-$; $-CHR^{15}OC(=O)S-$; $-CHR^{15}OC(=S)S-$; $-CHR^{15}SC(=O)N(R^{15})-$; $-CHR^{15}SC(=S)N(R^{15})-$; $-CHR^{15}SC(=O)O-$; $-CHR^{15}SC(=S)O-$; $-CHR^{15}SC(=O)S-$; $-CHR^{15}SC(=S)S-$; $-CHR^{15}SC(=NR^{15})S-$; $-CHR^{15}N(R^{15})C(=O)N(R^{15})-$; $-CHR^{15}O-N(R^{15})C(=O)N(R^{15})-$; $-CHR^{15}O-N(R^{15})C(=S)N(R^{15})-$; $-CHR^{15}O-N=C(R^7)NR^{15}-$; $-CHR^{15}O-N=C(R^7)OCH_2-$; $-CHR^{15}O-N=C(R^7)-N=N-$; $-CHR^{15}O-N=C(R^7)-C(=O)-$; $-CHR^{15}O-N=C(R^7)-C(=N-A^2-Z^1)-A^1-$; $-CHR^{15}O-N=C(R^7)-C(R^7)=N-A^2-A^3-$; $-CHR^{15}O-N=C(-C(R^7)=N-A^2-Z^1)-$; $-CHR^{15}O-N=C(R^7)-CH_2O-$; $-CHR^{15}O-N=C(R^7)-CH_2S-$; $-O-CH_2CH_2O-N=C(R^7)-$; $-CHR^{15}O-C(R^{15})=C(R^7)-$; $-CHR^{15}O-C(R^7)=N-$; $-CHR^{15}S-C(R^7)=N-$; $-C(R^7)=N-NR^{15}-$; $-CH=N-N=C(R^7)-$; $-CHR^{15}N(R^{15})-N=C(R^7)-$; $-CHR^{15}N(COCH_3)-N=C(R^7)-$; $-OC(=S)NR^{15}C(=O)-$; $-CHR^6-C(=W^1)-A^1-$; $-CHR^6CHR^6-C(=W^1)-A^1-$; $-CR^6=CR^6-C$ $(=W^1)-A^1-$; $-C\equiv C-C(=W^1)-A^1-$; $-N=CR^6-C(=W^1)-A^1-$; or a direct bond; and the directionality of the Y linkage is defined such that the moiety depicted on the left side of the linkage is bonded to E and the moiety on the right side of the linkage is bonded to Z;

$Z^1$ is H or $-A^3-Z$;

$W^1$ is O or S;

$A^1$ is O; S; $NR^{15}$; or a direct bond;

$A^2$ is O; $NR^{15}$; or a direct bond;

$A^3$ is $-C(=O)-$; $-S(O)_2-$; or a direct bond;

each $R^6$ is independently H; 1–2 $CH_3$; $C_2$–$C_3$ alkyl; $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; $NH_2C(O)NH$; $(C_1$–$C_3$ alkyl)$NHC(O)NH$; $(C_1$–$C_3$ alkyl)$_2NC(O)NH$; $N(C_1$–$C_3$ alkyl)$_2$; piperidinyl; morpholinyl; 1–2 halogen; cyano; or nitro;

each $R^7$ is independently H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; halogen; cyano; nitro; hydroxy; amino; $NH(C_1$–$C_6$ alkyl); $N(C_1$–$C_6$ alkyl)$_2$; or morpholinyl;

each Z is independently selected from
  i) $C_1$–$C_{10}$ alkyl, $C_2$–$C_{10}$ alkenyl, and $C_2$–$C_{10}$ alkynyl each substituted with $R^9$ and unsubstituted or substituted with one or more $R^{10}$;
  ii) $C_3$–$C_8$ cycloalkyl, $C_3$–$C_8$ cycloalkenyl and phenyl each substituted with $R^9$ and unsubstituted or substituted with one or more $R^{10}$;
  iii) a ring system selected from 3 to 14-membered monocyclic, fused bicyclic and fused tricyclic nonaromatic heterocyclic ring systems and 5 to 14-membered monocyclic, fused bicyclic and fused tricyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each nonaromatic or aromatic heterocyclic ring system substituted with $R^9$ and unsubstituted or substituted with one or more $R^{10}$;
  iv) a multicyclic ring system selected from 8 to 14-membered fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from $C(=O)$ and $S(O)_2$, and any remaining rings as aromatic carbocyclic rings, each multicyclic ring system substituted with $R^9$ and unsubstituted or substituted with one or more $R^{10}$; and
  v) adamantyl substituted with $R^9$ and unsubstituted or substituted with one or more $R^{10}$;

each Q is independently selected from the group $-CHR^{13}-$, $-NR^{13}-$, $-O-$, and $-S(O)_p-$;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alknyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2(C_1$–$C_6$ alkyl); $NH(C_1$–$C_6$ alkyl); $N(C_1$–$C_6$ alkyl)$_2$; cyano; nitro; $SiR^{19}R^{20}R^{21}$; or $GeR^{19}R^{20}R^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; $CO_2(C_1$–$C_6$ alkyl); $NH(C_1$–$C_6$ alkyl); $N(C_1$–$C_6$ alkyl)$_2$; $-C(R^{18})=NOR^{17}$; cyano; nitro; $SF_5$; $SiR^{22}R^{23}R^{24}$; or $GeR^{22}R^{23}R^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each unsubstituted or substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ when taken together form $-OCH_2O-$ or $-OCH_2CH_2O-$; each $CH_2$ group of said taken together $R^9$ and $R^{10}$ unsubstituted or substituted with 1–2 halogen; or when Y and an $R^{10}$ are attached to adjacent atoms on Z and Y is $-CHR^{15}O-N=C(R^7)-$, $-O-N=C(R^7)-$, $-O-CH_2CH_2O-N=C(R^7)-$, $-CHR^{15}O-C(R^{15})=C(R^7)-$, $-CH=N-N=C(R^7)-$, $-CHR^{15}N(R^{15})-N=C(R^7)-$ or $-CHR^{15}N(COCH_3)-N=C(R^7)-$, $R^7$ and said adjacently attached $R^{10}$ when taken together form $-(CH_2)_r-J-$ such that J is attached to Z;

J is $-CH_2-$; $-CH_2CH_2-$; $-OCH_2-$; $-CH_2O-$; $-SCH_2-$; $-CH_2S-$; $-N(R^{16})CH_2-$; or $-CH_2N(R^{16})-$; each $CH_2$ group of said J unsubstituted or substituted with 1 to 2 $CH_3$;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; $Si(R^{25})_3$; or $Ge(R^{25})_3$;

each $R^{13}$ is independently H; $C_1$–$C_6$ alkyl; $C_1$–$C_6$ haloalkyl; or phenyl unsubstituted or substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl;

each $R^{15}$ is independently H; $C_1$–$C_3$ alkyl; $C_3$–$C_6$ cycloalkyl; or phenyl or benzyl, each unsubstituted or substituted on the phenyl ring with halogen, $C_1$–$C_4$ alkyl, $C_1$–$C_4$ haloalkyl, $C_1$–$C_4$ alkoxy, $C_1$–$C_4$ haloalkoxy, nitro or cyano; or when Y is $-CHR^{15}N(R^{15})C(=O)N(R^5)-$, the two $R^{15}$ attached to nitrogen atoms on said group when taken together form $-(CH_2)_s-$; or when Y is $-CHR^{15}O-N=C(R^7)NR^{15}-$, $R^7$ and the adjacently attached $R^{15}$ when taken together form $-CH_2-(CH_2)_s-$; $-O-(CH_2)_s-$; $-S-(CH_2)_s-$; or $-N(C_1$–$C_3$ alkyl)$-(CH_2)_s-$; with the directionality of said linkage defined such that the moiety depicted on the left side of the linkage is bonded to the carbon and the moiety on the right side of the linkage is bonded to the nitrogen;

$R^{16}$, $R^{17}$, and $R^{18}$ are each independently H; $C_1$–$C_3$ alkyl; $C_3$–$C_6$ cycloalkyl; or phenyl unsubstituted or substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{19}$, $R^{20}$, $R^{21}$, $R^{22}$, $R^{23}$, and $R^{24}$ are each independently $C_1$–$C_6$ alkyl; $C_2$–$C_6$ alkenyl; $C_1$–$C_4$ alkoxy; or phenyl;

each $R^{25}$ is independently $C_1$–$C_4$ alkyl; $C_1$–$C_4$ haloalkyl; $C_2$–$C_4$ alkenyl; $C_1$–$C_4$ alkoxy; or phenyl;

m, n and p are each independently 0, 1 or 2;

r is 0 or 1; and s is 2 or 3.

2. A compound of claim 1, wherein

E is selected from the group 1H-pyrrole-1,2-, 2,3- and 3,4-diyl; 2,3- and 3,4-furandiyl; 2,3- and 3,4-thiophenediyl; 1H-pyrazole-1,5-, 3,4- and 4,5-diyl; 1H-imidazole-1,2-, 4,5- and 1,5-diyl; 3,4- and 4,5-isoxazolediyl; 4,5-oxazolediyl; 3,4- and 4,5-isothiazolediyl; 4,5-thiazolediyl; 1H-1,2,3-triazole-1,5- and 4,5-diyl; 2H-1,2,3-triazole-4,5-diyl; 1H-1,2,4-triazole-1,5-diyl; 4H-1,2,4-triazole-3,4-diyl; 1,2,3-oxadiazole-4,5-diyl; 1,2,5-oxadiazole-3,4-diyl; 1,2,3-thiadiazole-4,5-diyl; 1,2,5-thiadiazole-3,4-diyl; 1H-tetrazole-1,5-diyl; 2,3- and 3,4-pyridinediyl; 3,4- and 4,5-pyridazinediyl; 4,5-pyrimidinediyl; 2,3-pyrazinediyl; 1,2,3-triazine-4,5-diyl; 1,2,4-triazine-5,6-diyl; 1H-indole-1,4-, 1,5-,1,6-, 1,7-, 2,4-, 2,5-, 2,6-, 2,7-, 3,4-, 3,5-, 3,6-, 3,7-, 1,2-, 2,3-, 4,5-, 5,6- and 6,7-diyl; 2,4-, 2,5-, 2,6-, 2,7-, 3,4-, 3,5-, 3,6-, 3,7-, 2,3-, 4,5-, 5,6- and 6,7-benzofurandiyl; benzo[b]thiophene-2,4-, 2,5-, 2,6-, 2,7-, 3,4-, 3,5-, 3,6-, 3,7-, 2,3-, 4,5-, 5,6- and 6,7-diyl; 1H-indazole-1,4-, 1,5-, 1,6-, 1,7-, 3,4-, 3,5-, 3,6-, 3,7-, 4,5-, 5,6- and 6,7-diyl; 1H-benzimidazole-1,4-, 1,5-, 1,6-, 1,7-, 2,4-, 2,5-, 2,6-, 2,7-, 4,5-, 5,6- and 6,7-diyl; 1,2-benzisoxazole-3,4-, 3,5-, 3,6-, 3,7-, 4,5-, 5,6- and 6,7-diyl; 2,4-, 2,5-, 2,6-, 2,7-, 4,5-, 5,6- and 6,7-benzoxazolediyl; 1,2-benzisothiazole-3,4-, 3,5-, 3,6-, 3,7-, 4,5-, 5,6- and 6,7-diyl; 2,4-, 2,5-, 2,6-, 2,7-, 4,5-, 5,6- and 6,7-benzothiazolediyl; 2,5-, 2,6-, 2,7-, 2,8-, 3,5-, 3,6-, 3,7-, 3,8-, 4,5-, 4,6-, 4,7-, 4,8-, 2,3-, 3,4-, 5,6-, 6,7- and 7,8-quiolinediyl; 1,5-, 1,6-, 1,7-, 1,8-, 3,5-, 3,6-, 3,7-, 3,8-, 4,5-, 4,6-, 4,7-, 4,8-, 3,4-, 5,6-, 6,7- and 7,8-isoquinolinediyl; 3,5-, 3,6-, 3,7-, 3,8-, 4,5-, 4,6-, 4,7-, 4,8-, 3,4-, 5,6-, 6,7- and 7,8-cinnolinediyl; 1,5-, 1,6-, 1,7-, 1,8-, 5,6-, 6,7- and 7,8-phthalazinediyl; 2,5-, 2,6-, 2,7-, 2,8-, 4,5-, 4,6-, 4,7-, 4,8-, 5,6-, 6,7- and 7,8-quinazolinediyl; 2,5-, 2,6-, 2,7-, 2,8-, 2,3-, 5,6-, 6,7- and 7,8-quinoxalinediyl; 1,8-naphthyridine-2,5-, 2,6-, 2,7-, 3,5-, 3,6-, 4,5-, 2,3- and 3,4-diyl; 2,6-, 2,7-, 4,6-, 4,7-, 6,7-pteridinediyl; pyrazolo[5,1-b]thiazole-2,6-, 2,7-, 3,6-, 3,7-, 2,3- and 6,7-diyl; thiazolo[2,3-c]-1,2,4-triazole-2,5-, 2,6-, 5,6-diyl; 2-oxo-1,3-benzodioxole-4,5- and 5,6-diyl; 1,3-dioxo-1H-isoindole-2,4-, 2,5-, 4,5- and 5,6-diyl; 2-oxo-2H-1-benzopyran-3,5-, 3,6-, 3,7-, 3,8-, 4,5-, 4,6-, 4,7-, 4,8-, 5,6-, 6,7- and 7,8-diyl; [1,2,4]triazolo[1,5-a]pyridine-2,5-, 2,6-, 2,7-, 2,8-, 5,6-, 6,7- and 7,8-diyl; 3,4-dihydro-2,4-dioxo-2H-1,3-benzoxazine-3,5-, 3,6-, 3,7-, 3,8-, 5,6-, 6,7- and 7,8-diyl; 2,3-dihydro-2-oxo-3,4-, 3,5-, 3,6-, 3,7-, 4,5-, 5,6- and 6,7-benzofurandiyl; thieno[3,2-d]thiazole-2,5-, 2,6-, and 5,6-diyl; 5,6,7,8-tetrahydro-2,5-, 2,6-, 2,7-, 2,8-, 3,5-, 3,6-, 3,7-, 3,8-, 4,5-, 4,6-, 4,7-, 4,8-, 2,3- and 3,4-quinolinediyl; 2,3-dihydro-1,1,3-trioxo-1,2-benzisothiazole-2,4-, 2,5-, 2,6-, 2,7-, 4,5-, 5,6- and 6,7-diyl; 1,3-benzodioxole-2,4-, 2,5-, 4,5- and 5,6-diyl; 2,3-dihydro-2,4-, 2,5-, 2,6-, 2,7-, 3,4-, 3,5-, 3,6-, 3,7-, 4,5-, 5,6- and 6,7-benzofurandiyl; 2,3-dihydro-1,4-benzodioxin-2,5-, 2,6-, 2,7-, 2,8-, 5,6- and 6,7-diyl; 5,6,7,8-tetrahydro-4H-cyclohepta[b]thiophene-2,4-, 2,5-, 2,6-, 2,7-, 2,8-, 3,4-, 3,5-, 3,6-, 3,7-, 3,8-, and 2,3-diyl; each aromatic ring system unsubstituted or substituted with one of $R^3$, $R^4$, or both $R^3$ and $R^4$;

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently halogen; cyano; nitro; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfonyl; $C_2$–$C_6$ alkylcarbonyl; $C_2$–$C_6$ alkoxycarbonyl; ($C_1$–$C_4$ alkyl)NHC(O); ($C_1$–$C_4$ alkyl)$_2$NC(O); benzoyl; or phenylsulfonyl;

Y is —O—; —CH═CH—; —C≡C—; —CH$_2$O—; —OCH$_2$—; —CH$_2$S(O)$_n$—; —CH$_2$O—N═C(R$^7$)—; —(R$^7$)C═N—OCH(R$^{15}$)—; —C(R$^7$)═N—O—; —CH$_2$OC(O)NH—; —CH$_2$S—C(R$^7$)═N—; —CH═CR$^6$—C(═W$^1$)—A$^1$—; or a direct bond;

$R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ $_{C2}$–$C_6$ alkynyl; $C_3$–$C_6$ cycloalkyl; halogen; or cyano; or when Y and an $R^{10}$ are attached to adjacent atoms on Z and Y is —CH$_2$O—N═C(R$^7$)—, $R^7$ and said adjacently attached $R^{10}$ when taken together form —(CH$_2$)$_r$—J— such that J is attached to Z;

Z is selected from the group $C_1$–$C_{10}$ alkyl; $C_3$–$C_8$ cycloalkyl; phenyl; naphthalenyl; anthracenyl; phenanthrenyl; 1H-pyrrolyl; furanyl; thienyl; 1H-pyrazolyl; 1H-imidazolyl; isoxazolyl; oxazolyl; isothiazolyl; thiazolyl; 1H-1,2,3-triazolyl; 2H-1,2,3-triazolyl; 1H-1,2,4-triazolyl; 4H-1,2,4-triazolyl; 1,2,3-oxadiazolyl; 1,2,4-oxadiazolyl; 1,2,5-oxadiazolyl; 1,3,4-oxadiazolyl; 1,2,3-thiadiazolyl; 1,2,4-thiadiazolyl; 1,2,5-thiadiazolyl; 1,3,4-thiadiazolyl; 1H-tetrazolyl; 2H-tetrazolyl; pyridinyl; pyridazinyl; pyrimidinyl; pyrazinyl; 1,3,5-triazinyl; 1,2,4-triazinyl; 1,2,4,5-tetrazinyl; 1H-indolyl; benzofuranyl; benzo[b]thiophenyl; 1H-indazolyl; 1H-benzimidazolyl; benzoxazolyl; benzothiazolyl; quinolinyl; isoquinolinyl; cinnolinyl; phthalazinyl; quinazolinyl; quinoxalinyl; 1,8-naphthyridinyl; pteridinyl; 2,3-dihydro-1H-indenyl; 1,2,3,4-tetrahydronaphthalenyl; 6,7,8,9-tetrahydro-5H-benzocycloheptenyl; 5,6,7,8,9,10-hexahydrobenzocyclooctenyl; 2,3-dihydro-3-oxobenzofuranyl; 1,3-dihydro-1-oxoisobenzofuranyl; 2,3-dihydro-2-oxobenzofuranyl; 3,4-dihydro-4-oxo-2H-1-benzopyranyl; 3,4-dihydro-1-oxo-1H-2-benzopyranyl; 3,4-dihydro-3-oxo-1H-2-benzopyranyl; 3,4-dihydro-2-oxo-2H-1-benzopyranyl; 4-oxo-4H-1-benzopyranyl; 2-oxo-2H-1-benzopyranyl; 2,3,4,5-tetrahydro-5-oxo-1-benzoxepinyl; 2,3,4,5-tetrahydro-2-oxo-1-benzoxepinyl; 2,3-dihydro-1,3-dioxo-1H-isoindolyl; 1,2,3,4-tetrahydro-1,3-dioxoisoquinolinyl; 3,4-dihydro-2,4-dioxo-2H-1,3-benzoxazinyl; 2-oxo-1,3-benzodioxyl; 2,3-dihydro-1,1,3-trioxo-1,2-benzisothiazolyl; 9H-fluorenyl; azulenyl; and thiazolo[2,3-c]-1,2,4-triazolyl; each group substituted with $R^9$ and unsubstituted or substituted with one or more $R^{10}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; cyano; CO$_2$($C_1$–$C_6$ alkyl); NH($C_1$–$C_6$ alkyl); N($C_1$–$C_6$ alkyl)$_2$; SiR$^{22}$R$^{23}$R$^{24}$; or GeR$^{22}$R$^{23}$R$^{24}$; or $R^9$ is $C_3$–$C_6$ cycloalkyl, phenyl, phenoxy, pyridinyl, pyridinyloxy, pyrimidinyl, or pyrimidinyloxy, each unsubstituted or substituted with one of $R^{11}$, $R^{12}$, or both $R^{11}$ and $R^{12}$; and each $R^{15}$ is independently H; $C_1$–$C_3$ alkyl; or $C_3$–$C_6$ cycloalkyl.

3. A compound of claim 2 wherein

E is selected from the group 2,3- and 3,4-furandiyl; 2,3- and 3,4-thiophenediyl; 2,3- and 3,4-pyridinediyl; 4,5- pyrimidinediyl; 2,4-, 2,7-, 3,5-, 2,3-, 4,5-, 5,6- and 6,7-benzofurandiyl; benzo[b]thiophene-2,4-, 2,7-, 3,5-, 2,3-, 4,5-, 5,6- and 6,7-diyl; each aromatic ring system unsubstituted or substituted with one of $R^3$, $R^4$, or both $R^3$ and $R^4$;

Z is selected from the group phenyl; 1,2,4-thiadiazolyl; pyridinyl; pyrimidinyl; and naphthalenyl; each group substituted with $R^9$ and unsubstituted or substituted with one or more $R^{10}$;

$R^7$ is H; $C_1$–$C_6$ alkyl; $C_1$–$C_6$ haloalkyl; $C_1$–$C_6$ alkoxy; $C_1$–$C_6$ alkylthio; $C_2$–$C_6$ alkenyl; $C_2$–$C_6$ alkynyl; cyclopropyl; halogen; or cyano; or when Y and an $R^{10}$ are attached to adjacent atoms on Z and Y is —$CH_2$O—N═C($R^7$)—, $R^7$ and said adjacently attached $R^{10}$ when taken together form —$(CH_2)_r$—J— such that J is attached to Z;

J is —$CH_2$— or —$CH_2CH_2$—; and r is 1.

4. A compound of claim 3 wherein:

A is O; N; $NR^5$; or $CR^{14}$;

X is $OR^1$;

$R^1$ is $C_1$–$C_3$ alkyl;

$R^2$ is H or $C_1$–$C_2$ alkyl;

Y is —O—; —CH═CH—; —$CH_2$O—; —$CH_2$O—N═C($R^7$)—; —($R^7$)C═N—OCH($R^{15}$)—; —$CH_2$OC(═O)NH—; —$CH_2$S—C($R^7$)═N—; or —CH═$CR^6$—C(═$W^1$)—$A^1$—;

$R^7$ is H; $C_1$–$C_3$ alkyl; $C_1$–$C_3$ haloalkyl; $C_1$–$C_3$ alkoxy; $C_1$–$C_3$ alkylthio; or cyclopropyl; and each $R^{15}$ is independently H; $C_1$–$C_3$ alkyl; or cyclopropyl.

5. A compound of claim 4 wherein:

A is O or $NR^5$;

G is C; and

Y is —O—; —$CH_2$O—; or —$CH_2$O—N═C($R^7$)—.

6. A compound of claim 5 wherein:

$R^1$ is methyl; and $R^2$ is methyl.

7. A compound of claim 4 wherein:

A is N or $CR^{14}$;

G is N; and

Y is —O—; —$CH_2$O—; or —$CH_2$O—N═C($R^7$)—.

8. A compound of claim 7 wherein:

$R^1$ is methyl; and $R^2$ is methyl.

9. The compound of claim 4 which is selected from the group:

2,4-dihydro-5-methoxy-2-methyl-4-[2-[[[[1-[3-(trimethylsilyl)phenyl]ethylidene]amino]oxy]methyl]-3-thienyl]-3H-1,2,4-triazol-3-one;

2,4-dihydro-5-methoxy-2-methyl-4-[2-[[[[1-[3-(trifluoromethyl)phenyl]ethylidene]amino]oxy]methyl]-3-thienyl]-3H-1,2,4-triazol-3one;

4-[2-[(2,5-dimethylphenoxy)methyl]-3-thienyl]-2,4-dihydro-5-methoxy-2-methyl-3H-1,2,4-triazol-3-one;

(1,1-dimethylethyl)2-chloro-3-[3-(1,5-dihydro-3-methoxy-1-methyl-5-oxo-4H-1,2,4-triazol-4-yl)]—2-thienyl]-2-propenoate;

4-[2-[[[3-(4-chlorophenyl)-1,2,4-thiadiazol-5-yl]oxy]methyl]-3-thienyl]-2,4-dihydro-5-methoxy-2-methyl-3H-1,2,4-triazol-3-one; and 2,4-dihydro-5-methoxy-2-methyl-4-[2-[[[3-[4-(trifluoromethyl)phenyl]-1,2,4-thiadiazol-5-yl]oxy]methyl]-3-thienyl]-3H-1,2,4-triazol-3-one.

10. A fungicidal composition comprising a fungicidally effective amount of a compound of claim 1 and at least one of a surfactant, a solid diluent or a liquid diluent.

11. A method for controlling plant diseases caused by fungal plant pathogens comprising applying to the plant or portion thereof, or to the plant seed or seedling, a fungicidally effective amount of a compound of claim 1.

12. A compound selected from Formula I, N-oxides and agriculturally suitable salts thereof,

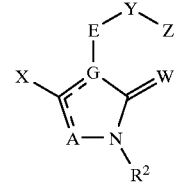

wherein:

E is a ring system selected from i) 5 to 12-membered monocyclic and fused bicyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, and each fused bicyclic ring system does or does not contain one nonaromatic ring that does or does not include one or two Q as ring members and does or does not include one or two ring members independently selected from C(═O) and S(O)$_2$, provided that G is attached to an aromatic ring, and when G and Y are attached to the same ring, then G and Y are attached to adjacent ring members, each aromatic heterocyclic ring system unsubstituted or substituted with one of $R^3$, $R^4$, or both $R^3$ and $R^4$;

A is O; S; N; $NR^5$; or $CR^{14}$;

G is C or N; provided that when G is C, then A is O, S or $NR^5$ and the floating double bond is attached to G; and when G is N, then A is N or $CR^{14}$ and the floating double bond is attached to A;

W is O; S; NH; N($C_1$–$C_6$ alkyl); or NO($C_1$–$C_6$ alkyl);

X is $OR^1$; S(O)$_m R^1$; or halogen;

$R^1$ is $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

$R^2$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

$R^3$ and $R^4$ are each independently halogen; cyano; nitro; hydroxy; $C_1C_6$ alkyl; $C_1C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1C_6$ alkoxy; $C_1C_6$ haloalkoxy; $C_2$–$C_6$ alkenyloxy; $C_2$–$C_6$ alkynyloxy; $C_1$–$C_6$ alkylthio; $C_1C_6$ alkylsulfinyl; $C_1$–$C_6$ alkylsulfonyl; formyl; $C_2$–$C_6$ alkylcarbonyl; $C_2$–$C_6$ alkoxycarbonyl; NH$_2$C(O); ($C_1$–$C_4$ alkyl)NHC(O); ($C_1$–$C_4$ alkyl)$_2$NC(O); Si($R^{25}$)$_3$; Ge($R^{25}$)$_3$; ($R^{25}$)$_3$Si—C≡C—; or phenyl, phenylethynyl, benzoyl, or phenylsulfonyl each substituted with $R^8$ and unsubstituted or substituted with one or more $R^{10}$;

$R^5$ is H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; or $C_2$–$C_4$ alkoxycarbonyl;

Y is —O—; —S(O)n—; —$NR^{15}$—; —C(=O)—; —CH($OR^{15}$)—; —$CHR^6$—; —$CHR^6CHR^6$—; —$CR^6$=$CR^6$—; —C≡C—; —$CHR^{15}$O—; —$OCHR^{15}$—; —$CHR^{15}$S(O)n—; —S(O)n$CHR^{15}$—; —$CHR^{15}$O—N=C($R^7$)—; —($R^7$)C=N—OCH($R^{15}$)—; —C($R^7$)=N—O—; —O—N=C($R^7$)—; —$CHR^{15}$OC(=O)N($R^{15}$)—; —$CHR^5$OC(=S)N($R^{15}$)—; —$CHR^{15}$O—N($R^5$)C(=O)N($R^{15}$)—; —$CHR^{15}$O—N($R^{15}$)C(=S)N($R^{15}$)—; —$CHR^{15}$O—N=C($R^7$)$NR^{15}$—; —$CHR^{15}$O—N=C($R^7$)$OCH_2$—; —$CHR^{15}$O—N=C($R^7$)—N=N—; —$CHR^{15}$O—N=C($R^7$)—C(=O)—; —$CHR^{15}$S—C($R^7$)=N—; —C($R^7$)=N—$NR^{15}$—; —CH=N—N=C($R^7$)—; —$CHR^{15}$N(COCH$_3$)—N=C($R^7$)—; —OC(=S)$NR^{15}$C(=O)—; —$CHR^6$—C(=$W^1$)—$A^1$—; —$CHR^6CHR^6$—C(=$W^1$)—$A^1$—; —$CR^6$=$CR^6$—C(=$W^1$)—$A^1$—; —C≡C—C(=$W^1$)—$A^1$—; —N=$CR^6$—C(=$W^1$)—$A^1$—; or a direct bond; and the directionality of the Y linkage is defined such that the moiety depicted on the left side of the linkage is bonded to E and the moiety on the right side of the linkage is bonded to Z;

$W^1$ is O or S;

$A^1$ is O; S; $NR^{15}$; or a direct bond;

each $R^6$ is independently H; 1–2 $CH_3$; $C_2$–$C_3$ alkyl; $C_1$–$C_3$ alkoxy; $C_3$–$C_6$ cycloalkyl; formylamino; $C_2$–$C_4$ alkylcarbonylamino; $C_2$–$C_4$ alkoxycarbonylamino; $NH_2$C(O)NH; ($C_1$–$C_3$ alkyl)NHC(O)NH; ($C_1$–$C_3$ alkyl)$_2$NC(O)NH; N($C_1$–$C_3$ alkyl)$_2$; piperidinyl; morpholinyl; 1–2 halogen; cyano; or nitro;

$R^7$ is H; $C_1$–$C_6$ alkyl; $C_1$–$C_6$ haloalkyl; $C_1$–$C_6$ alkoxy; $C_1$–$C_6$ haloalkoxy; $C_1$–$C_6$ alkylthio; $C_1$–$C_6$ alkylsulfinyl; $C_1$–$C_6$ alkylsulfonyl; $C_1$–$C_6$ haloalkylthio; $C_1$–$C_6$ haloalkylsulfinyl; $C_1$–$C_6$ haloalkylsulfonyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; halogen; cyano; or morpholinyl;

Z is selected from i) $C_1$–$C_{10}$ alkyl, $C_2$–$C_{10}$ alkenyl, and $C_2$–$C_{10}$ alkynyl each substituted with $R^9$ and unsubstituted or substituted with one or more $R^{10}$;

ii) $C_3$–$C_8$ cycloalkyl and phenyl each substituted with $R^9$ and unsubstituted or substituted with one or more $R^{10}$;

iii) a ring system selected from 3 to 14-membered monocyclic, fused bicyclic and fused tricyclic nonaromatic heterocyclic ring systems and 5 to 14-membered monocyclic, fused bicyclic and fused tricyclic aromatic heterocyclic ring systems, each heterocyclic ring system containing 1 to 6 heteroatoms independently selected from the group nitrogen, oxygen, and sulfur, provided that each heterocyclic ring system contains no more than 4 nitrogens, no more than 2 oxygens, and no more than 2 sulfurs, each nonaromatic or aromatic heterocyclic ring system substituted with $R^9$ and unsubstituted or substituted with one or more $R^{10}$; and iv) a multicyclic ring system selected from 8 to 14-membered fused-bicyclic and fused-tricyclic ring systems which are an aromatic carbocyclic ring system, a nonaromatic carbocyclic ring system, or a ring system containing one or two nonaromatic rings that each include one or two Q as ring members and one or two ring members independently selected from C(=O) and S(O)$_2$, and any remaining rings as aromatic carbocyclic rings, each multicyclic ring system substituted with $R^9$ and unsubstituted or substituted with one or more $R^{10}$;

each Q is independently selected from the group —$CHR^{13}$—, —$NR^{13}$—, —O—, and —S(O)$_p$—;

$R^8$ is H; 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$($C_1$–$C_6$ alkyl); NH($C_1$–$C_6$ alkyl); N($C_1$–$C_6$ alkyl)$_2$; cyano; nitro; Si$R^{19}R^{20}R^{21}$; or Ge$R^{19}R^{20}R^{21}$;

$R^9$ is H; 1–2 halogen; $C_1$–$C_6$ alkyl; $C_1$–$C_6$ haloalkyl; $C_1$–$C_6$ alkoxy; $C_1$–$C_6$ haloalkoxyl; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$($C_1$–$C_6$ alkyl); NH($C_1$–$C_6$ alkyl); N($C_1$–$C_6$ alkyl)$_2$; —C($R^{18}$)=$NOR^{17}$; cyano; nitro; SF$_5$; Si$R^{22}R^{23}R^{24}$; or Ge$R^{22}R^{23}R^{24}$; or $R^9$ is phenyl, benzyl, benzoyl, phenoxy, pyridinyl, pyridinyloxy, thienyl, thienyloxy, furanyl, pyrimidinyl, or pyrimidinyloxy each unsubstituted or substituted with one of $R^{11}$, $R^{12}$, or both $R^{11}$ and $R^{12}$;

each $R^{10}$ is independently halogen; $C_1$–$C_4$ alkyl; $C_1$–$C_4$ haloalkyl; $C_1$–$C_4$ alkoxy; nitro; or cyano; or when $R^9$ and an $R^{10}$ are attached to adjacent atoms on Z, $R^9$ and said adjacently attached $R^{10}$ when taken together form —$OCH_2$O— or —$OCH_2CH_2$O—; each $CH_2$ group of said taken together $R^9$ and $R^{10}$ unsubstituted or substituted with 1–2 halogen; or when Y and an $R^{10}$ are attached to adjacent atoms on Z and Y is —$CHR^{15}$O—N=C($R^7$)—, —O—N=C($R^7$)—, —CH=N—N=C($R^7$)—, or —$CHR^{15}$N(COCH$_3$)—N=C($R^7$)—, $R^7$ and said adjacently attached $R^{10}$ when taken together form —(CH$_2$)$_r$—J— such that J is attached to Z;

J is —$CH_2$—; —$CH_2CH_2$—; —$OCH_2$—; —$CH_2$O—; —$SCH_2$—; —$CH_2$S—; —N($R^{16}$)$CH_2$—; or —$CH_2$N($R^{16}$)—; each $CH_2$ group of said J unsubstituted or substituted with 1 to 2 $CH_3$;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; cyano; Si($R^{25}$)$_3$; or Ge($R^{25}$)$_3$;

each $R^{13}$ is independently H; $C_1$–$C_6$ alkyl; $C_1$–$C_6$ haloalkyl; or phenyl unsubstituted or substituted with halogen, $C_1$–$C_4$ alkyl, $C_1$–$C_4$ haloalkyl, $C_1$–$C_4$ alkoxy, $C_1$–$C_4$ haloalkoxy, nitro or cyano;

$R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; or $C_3$–$C_6$ cycloalkyl;

each $R^{15}$ is independently H; $C_1$–$C_3$ alkyl; $C_3$–$C_6$ cycloalkyl; or phenyl or benzyl, each unsubstituted or substituted on the phenyl ring with halogen, $C_1$–$C_4$ alkyl, $C_1$–$C_4$ haloalkyl, $C_1$–$C_4$ alkoxy, $C_1$–$C_4$ haloalkoxy, nitro or cyano; or when Y is —$CHR^{15}$O—N=C($R^7$)$NR^{15}$—, $R^7$ and the adjacently attached $R^{15}$ when taken together form —$CH_2$—(CH$_2$)$_s$—; —O—(CH$_2$)$_s$—; —S—(CH$_2$)$_s$—; or —N($C_1$–$C_3$ alkyl)—(CH$_2$)$_s$—; with the directionality of said linkage defined such that the moiety depicted on the left side of the linkage is bonded to the carbon and the moiety on the right side of the linkage is bonded to the nitrogen;

$R^{16}$, $R^{17}$, and $R^{18}$ are each independently H; $C_1-C_3$ alkyl; $C_3-C_6$ cycloalkyl; or phenyl unsubstituted or substituted with halogen, $C_1-C_4$ alkyl, $C_1-C_4$ haloalkyl, $C_1-C_4$ alkoxy, $C_1-C_4$ haloalkoxy, nitro or cyano;

$R^{19}$, $R^{20}$, $R^{21}$, $R^{22}$, $R^{23}$, and $R^{24}$ are each independently $C_1-C_6$ alkyl; $C_1-C_4$ alkoxyl; or phenyl;

each $R^{25}$ is independently $C_1-C_4$ alkyl or phenyl;

m, n and p are each independently 0, 1 or 2;

r is 0 or 1; and s is 2 or 3.

13. A compound of claim 1 which is selected from compounds having the formula

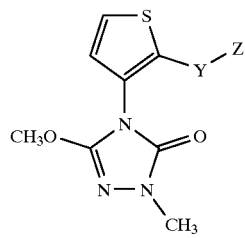

wherein

Y=—CH₂O—N=C(CH₃)— and Z=3—(CH₃)₃Si-Ph; Y=—CH₂O— and Z=2,5-diCH₃-Ph; Y=direct bond and Z=CH₂Br; Y=—CH₂O—N=C(CH₃)— and Z=3-CF₃-Ph; Y=—CH=C(Cl)—C(=O)—O— and Z=t-Bu; Y=—CH₂O—N=C(CH₃)— and Z=4- CF₃-pyridin-2-yl; Y=direct bond and Z=3-(3-CF₃-Ph)-1,2,4-oxadiazol-5-yl; Y=—CH₂O—N=C(CH₃)— and Z=3,4-diCl-Ph; Y=—CH₂O—N=C(NH₂)— and Z=3-CF₃-Ph; Y=—CH₂O—N=C(CH₃)— and Z=3,5-diBr-Ph; Y=—CH₂O—N=C(CH₃)— and Z=3,5-d.Cl-Ph; Y=—CH₂O—N=C(CH₃)— and Z=2-naphthalenyl; Y=—CH₂O—N=C(CH₂CH₃)— and Z=3-CF₃-Ph; Y=—CH₂O— and Z=3-(4-Cl-Ph)-1,2,4-thiadiazol-5-yl; Y=—CH₂O — and Z=3-(3,5-diCl-Ph)-1,2,4-thiadiazol-5-yl; or Y=—CH₂O— and Z=3-(4-CF₃-Ph)-1,2,4-thiadiazol-5-yl.

14. A compound of claim 1 which is selected compounds having the formula

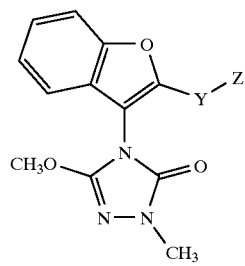

wherein

Y=direct bond and Z=CH₂Br; Y=—CH₂O—N=C(CH₃)— and Z=3,4-diCl-Ph; Y=—CH₂O—N=C(CH₃)— and Z=3-(CH₃)₃Si-Ph; Y=—CH₂O—N=C(CH₃)— and Z=4-CF₃-pyridin-2-yl; or Y=—CH₂O—N=C(CH₃)— and Z=3-CF₃-Ph.

15. A compound of claim 1 which is selected from compounds having the formula

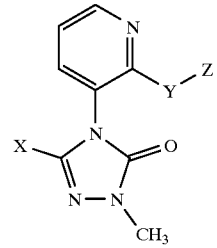

wherein

X=Cl, Y=direct bond and Z=CH₃; X=CH₃O, Y=direct bond and Z=CH₃; X=CH₃O, Y=—CH₂O—N=C(CH₃)— and Z=3-CF₃-Ph; X=CH₃O, Y=—CH₂O—N=C(CH₃)— and Z=4—CF₃-pyridin-2-yl; X=CH₃O, Y=—CH₂O—N=C(CH₃)— and Z=3,4-diCl-Ph; X=CH₃O, Y=—CH₂O—N=C(CH₃)— and Z=3-(CH₃)₃Si-Ph; X=CH₃O, Y=—CH₂O—N=C(CH₃)— and Z=3,5-diCl-Ph; X=CH₃O, Y=—CH₂O—N=C(CH₃)— and Z=3,5-diBr-Ph; X=CH₃O, Y=—CH₂O—N=C(NH₂)— and Z=3-CF₃-Ph; X=CH₃O, Y=—CH₂S— and Z=5-CF₃-4H-1,2,4-triazol-3-yl; X=CH₃O, Y=direct bond and Z=3-(3-CF₃-Ph)-1,2,4-oxadiazol-5-yl; X=CH₃O, Y=—CH₂— and Z=3-CF₃-1H-pyrazol-1-yl; X=CH₃O, Y=—CH₂O— and Z=2-Cl-5-CF₃-Ph; X=CH₃O, Y=—CH₂O— and Z=2,5-diCH₃-Ph; X=CH₃O, Y=—CH₂O—N=C(CH₃)— and Z=2-naphthalenyl; X=CH₃O, Y=—O— and Z=3-PhO-Ph; or X=Cl, Y=—O— and Z=3-PhO-Ph.

16. A compound of claim 1 which is selected from compounds having the formula

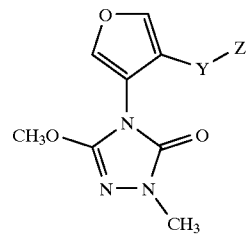

wherein

Y=direct bond and Z=3-(3-CF₃-Ph)-1,2,4-oxadiazol-5-yl; Y=direct bond and Z=CH₂Br; Y=—CH₂O—N=C(CH₃)— and Z=2-naphthalenyl; Y=—CH₂O—N=C(CH₃)— and Z=3,4-diCl-Ph; Y=—CH₂O—N=C(CH₃)— and Z=4-CF₃-pyridin-2-yl; Y=—CH₂O—N=C(CH₃)— and Z=3,5-diCl-Ph; Y=—CH₂O—N=C(CH₃)— and Z=3-(CH₃)₃Si-Ph; Y=—CH₂O—N=C(NH₂)— and Z=3-CF₃-Ph; Y=—CH₂O—N=C(CH₃)— and Z=3-CF₃-Ph; or Y=—CH₂O—N=C(CH₃)— and Z=3,5-diBr-Ph.

17. A compound of claim 1 having the formula
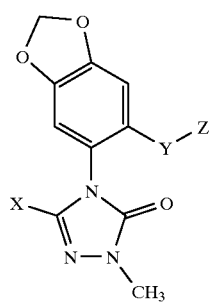
wherein X=CH₃O, Y=—CH₂O—N=C(CH₃)— and Z=3-CF₃-Ph.
18. A compound of claim 1 which is selected from compounds having the formula
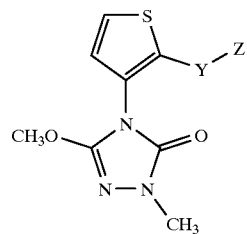
wherein
Y=—CH₂O—N=C(CH₃)— and Z=3-(CH₃)₃Si-Ph; Y=—CH₂O— and Z=2,5-diCH₃-Ph; Y=direct bond and Z=CH₂Br; Y=—CH₂O—N=C(CH₃)— and Z=3-CF₃-Ph; Y=—CH=C(Cl)—C(=O)—O— and Z=t-Bu; or Y=—CH₂O—N=C(CH₃)— and Z=4-CF₃-pyridin-2-yl.
* * * * *